US012702587B2

(12) United States Patent
Betser

(10) Patent No.: US 12,702,587 B2
(45) Date of Patent: Aug. 11, 2026

(54) OPHTHALMIC DEVICE

(71) Applicant: aVISI Ltd., Tel-Aviv (IL)

(72) Inventor: Nir Betser, Tel-Aviv (IL)

(73) Assignee: aVISI Ltd., Tel-Aviv (IL)

( * ) Notice: Subject to any disclaimer, the term of this patent is extended or adjusted under 35 U.S.C. 154(b) by 389 days.

(21) Appl. No.: 17/919,814

(22) PCT Filed: Apr. 20, 2021

(86) PCT No.: PCT/IL2021/050449
§ 371 (c)(1),
(2) Date: Oct. 19, 2022

(87) PCT Pub. No.: WO2021/214761
PCT Pub. Date: Oct. 28, 2021

(65) Prior Publication Data

US 2023/0346596 A1 Nov. 2, 2023

Related U.S. Application Data

(60) Provisional application No. 63/012,388, filed on Apr. 20, 2020.

(51) Int. Cl.
*A61F 9/00* (2006.01)
*A61K 9/00* (2006.01)
(Continued)

(52) U.S. Cl.
CPC .......... *A61F 9/0017* (2013.01); *A61K 9/0051* (2013.01); *A61K 31/192* (2013.01);
(Continued)

(58) Field of Classification Search
CPC ........... A61F 9/0017; A61F 2210/0004; A61F 2230/0006; A61F 2250/0067; A61F 2/14; A61F 2210/0076; A61F 2230/0008; A61F 9/0008; A61K 9/0051; A61P 27/02; A61M 31/002; B29D 11/00096
See application file for complete search history.

(56) References Cited

U.S. PATENT DOCUMENTS

| | | | |
|---|---|---|---|
| 3,416,530 | A | 12/1968 | Ness |
| 3,618,604 | A | 11/1971 | Ness |

(Continued)

FOREIGN PATENT DOCUMENTS

| | | |
|---|---|---|
| CN | 109195556 | 1/2019 |
| EP | 1189595 | 5/2003 |

(Continued)

OTHER PUBLICATIONS

Baker, M. I., Walsh, 8. P., Schwartz, Z., & Boyan, B. D. (2012). A review of polyvinyl alcohol and its uses in cartilage and orthopedic applications. Journal of Biomedical Materials Research Part B: Applied Biomaterials, 100(5), 1451-1457.*

(Continued)

*Primary Examiner* — Adam Marcetich

(57) ABSTRACT

An ophthalmic device including: a body having: a posterior surface; an anterior surface; wherein a size of the body, a shape of the posterior surface, and a shape of the anterior surface configures the device to reside on a bulbar conjunctiva of an eye.

27 Claims, 22 Drawing Sheets

(51) Int. Cl.
*A61K 31/192* (2006.01)
*A61K 31/196* (2006.01)
*A61K 31/496* (2006.01)
*A61K 31/567* (2006.01)
*A61K 47/10* (2017.01)
*A61K 47/14* (2017.01)
*A61K 47/38* (2006.01)

(52) U.S. Cl.
CPC .......... *A61K 31/196* (2013.01); *A61K 31/496* (2013.01); *A61K 31/567* (2013.01); *A61K 47/10* (2013.01); *A61K 47/14* (2013.01); *A61K 47/38* (2013.01); *A61F 2250/0067* (2013.01)

(56) References Cited

U.S. PATENT DOCUMENTS 3,828,777 A 8/1974 Ness
3,854,480 A 12/1974 Zaffaroni
3,867,519 A 2/1975 Michaels
3,868,445 A 2/1975 Ryde et al.
3,960,150 A 6/1976 Hussain et al.
3,986,510 A * 10/1976 Higuchi ............... A61K 9/0051 424/428
3,993,071 A * 11/1976 Higuchi ............... A61K 9/0051 424/428
3,995,635 A * 12/1976 Higuchi ................ A61F 9/0017 604/294
4,014,335 A 3/1977 Arnold
4,343,787 A 8/1982 Katz
4,484,922 A 11/1984 Rosenwald
4,540,408 A 9/1985 Lloyd
4,571,039 A 2/1986 Poler
4,592,752 A 6/1986 Neefe
5,104,213 A * 4/1992 Wolfson ................. G02B 1/043 351/159.02
5,137,728 A 8/1992 Bawa
5,395,618 A 3/1995 Darougar et al.
5,773,021 A 6/1998 Gurtler et al.
5,912,719 A 6/1999 Baude et al.
6,217,896 B1 4/2001 Benjamin
6,264,971 B1 * 7/2001 Darougar .............. A61F 9/0017 424/428
6,413,540 B1 * 7/2002 Yaacobi ............... A61K 9/0051 424/423
7,579,019 B2 8/2009 Tapolsky et al.
8,679,078 B2 3/2014 Leahy et al.
9,724,230 B2 8/2017 Badawi
10,010,502 B2 7/2018 Leahy et al.
2004/0121014 A1 * 6/2004 Guo ..................... A61K 31/573 424/471
2005/0010010 A1 1/2005 Kitamura et al.
2005/0118231 A1 * 6/2005 El Meski ............... A61K 47/38 514/57
2005/0171604 A1 * 8/2005 Michalow ............... A61L 27/04 623/20.28
2007/0112318 A1 * 5/2007 Leahy ................... A61F 9/0017 604/303
2007/0154522 A1 7/2007 Chow et al.
2008/0033351 A1 * 2/2008 Trogden ............... A61K 9/0051 604/57
2008/0243095 A1 10/2008 Kaiser et al.
2009/0093780 A1 * 4/2009 Tuitupou ................. A61N 1/30 514/789
2009/0104243 A1 * 4/2009 Utkhede ............... A61F 9/0017 424/423
2010/0036488 A1 * 2/2010 de Juan, Jr. ............. A61P 31/00 623/5.11
2012/0136322 A1 5/2012 Alster et al.
2013/0062809 A1 * 3/2013 Ellis ........................ A61P 27/02 264/250
2013/0090612 A1 4/2013 De Juan, Jr. et al.
2013/0172829 A1 7/2013 Badawi
2014/0074230 A1 3/2014 Blum
2016/0081920 A1 * 3/2016 Csaky ................... A61F 9/0017 514/514
2016/0338947 A1 * 11/2016 Leahy .................... A61K 47/32
2018/0085254 A1 3/2018 Rubin et al.
2019/0046434 A1 * 2/2019 Mota Leite Machado Mariz ....... A61K 31/4709
2021/0128351 A1 5/2021 Alster et al.

FOREIGN PATENT DOCUMENTS

EP 3187158 7/2017
JP 2010-537777 12/2010
JP 2011-516154 5/2011
JP 2014-530044 11/2014
JP 2016-049137 4/2016
KR 10-2022-0110912 8/2022
WO WO 2009/035571 3/2009
WO WO 2009/145842 12/2009
WO WO 2013/040426 3/2013
WO WO 2017/137934 8/2017
WO WO 2019/046714 3/2019
WO WO 2021/116907 6/2021
WO 2021/144820 7/2021
WO WO 2021/214761 10/2021
WO WO 2024/224394 10/2024

OTHER PUBLICATIONS

Convert Megapascal to Newton/square Meter. Accessed Oct. 2025 https://www.unitconverters.net/pressure/megapascal-to-newton-square-meter.htm (Year: 2025).*

The European Pharmacopoeia 10.0, 2.9.8 Resistance to crushing of tablets. 2020. https://www.pharmaceutical-networking.com/wp-content/uploads/2020/06/European-Pharmacopoeia-10.0.pdf (Year: 2020)*

International Search Report and the Written Opinion Dated Sep. 16, 2021 From the International Searching Authority Re. Application No. PCT/IL2021/050449. (15 Pages).

Invitation to Pay Additional Fees Dated Jun. 17, 2021 From the International Searching Authority Re. Application No. PCT/IL2021/050449. (2 Pages).

Addo et al. "Formulation and Characterization of Atropine Sulfate in Albumin-Chitosan Microparticles for In Vivo Ocular Drug Delivery", Journal of Pharmaceutical Sciences, 104(5):1677-1690, May 2015.

Agnihotri et al. "Chitosan Nanoparticles for Prolonged Delivery of Timolol Maleate", Drug Development and Industrial Pharmacy, 33(11): 1254-1262, Sep. 25, 2008.

Bertram et al. "Sustained Delivery of Timolol Malcate from Poly(lactic-Co- Glycolic Acid)/Poly(Lactic Acid) Microspheres for over 3 Months", Journal of Microencapsulation Micro and Nano Carriers,26(1): 18-26, Oct. 20, 2008.

He et al. "Development of Water-Compatible Molecularly Imprinted Polymers Based on Functionalized ß-Cyclodextrin for Controlled Release of Atropine", Polymers 2020, 12(1), 130: 1-14, Jan. 6, 2020.

Hearne et al. "Eye Care in The Intensive Care Unit", Journal of the Intensive Care Society, 19(4): 345-350, Mar. 22, 2008.

Lang "Ocular Drug Delivery Conventional Ocular Formulations", Advanced Drug Delivery Reviews, 16(1): 39-43, Aug. 1995.

Le Bourlais et al. "Ophthalmic Drug Delivery Systems—Recent Advances", Progress in Retinal and Eye Research, 17(1): 33-58, Jan. 1998.

Segal "Patches, Pumps and Timed Release", FDAConsumer,25(8): 13-15, 1991.

Valeant Pharmaceuticals International "TIMOPTIC® 0.25% and 0.5% (Timolol Maleate Ophthalmic Solution", Product Description, Valeant Pharmaceuticals International, Basuch & Lomb Inc., NDA 18086/S-076, 10 P., Revised Apr. 2016.

International Preliminary Report on Patentability Dated May 10, 2024 From the International Bureau of WIPO Re. Application No. PCT/IL2022/051137 (8 Pages).

(56) References Cited

OTHER PUBLICATIONS

Supplementary European Search Report and the European Search Opinion Dated Apr. 30, 2024 From the European Patent Office Re. Application No. 21792388.7. (8 Pages).
Baranowski et al. "Ophthalmic Drug Dosage Forms: Characterisation and Research Methods", The Scientific World Journal, 2014: 861904-1-861904-14, Mar. 18, 2014.
Kumar et al. "Ocular Inserts: A Novel Controlled Drug Delivery System", The Pharma Innovation Journal, 1(12 Part A): 1-16, Feb. 2013.
Patel et al. "Ocular Drug Delivery Systems: An Overview", World Journal of Pharmacology, 2(2): 47-64, Published Online Jun. 9, 2013.
International Search Report and the Written Opinion Dated Feb. 20, 2023 From the International Searching Authority Re. Application No. PCT/IL2022/051137 (14 Pages).
International Preliminary Report on Patentability Dated Nov. 3, 2022 From the International Bureau of WIPO Re. Application No. PCT/IL2021/050449. (11 Pages).
Notice of Reason(s) for Rejection Dated Jan. 7, 2025 From the Japan Patent Office Re. Application No. 2022-564297 and Its Translation Into English. (15 Pages).
Mirzaeei et al. "Design and Evaluation of Soluble Ocular Insert For Controlled Release of Chloramphenicol", Journal of Reports in Pharmaceutical Sciences, 6(2): 123-133, Jul. 3, 2017.
Notice of Reason(s) for Rejection Dated Aug. 5, 2025 From the Japan Patent Office Re. Application No. 2022-564297 and Its Translation Into English. (14 Pages).
Mali et al. "Polyvinyl Alcohol Films With Different Degrees of Hydrolysis and Polymerization", Semina Ciencias Exatas e Tecnologicas, 40(2): 169-178, XP093180190, Dec. 18, 2019.
Maria et al. "The Effect of the Degree of Hydrolysis of the PVA and the Plasticizer Concentration on the Color, Opacity, and Thermal and Mechanical Properties of Films Based on PVA and Gelatin Blends", Journal of Food Engineering, 87(2): 191-199, XP022496969, Jul. 2008.
Communication Pursuant to Article 94(3) EPC Dated Sep. 18, 2025 From the European Patent Office Re. Application No. 21792388.7 (8 Pages).
Communication Pursuant to Article 94(3) EPC Dated Dec. 9, 2025 From the European Patent Office Re. Application No. 22817399.3 (7 Pages).
Supplementary European Search Report and the European Search Opinion Dated Feb. 4, 2026 From the European Patent Office Re. Application No. 25216421.5. (9 Pages).
Examination Report Dated Mar. 4, 2026 From the Australian Government, IP Australia Re. Application No. 2021258583. (6 Pages).
Official Action Dated May 15, 2026 from the U.S. Appl. No. 19/385,242. (29 Pages).
Restriction Official Action Dated Mar. 27, 2026 from the U.S. Appl. No. 19/385,242. (6 pages).
Summons to Attend Oral Proceedings Pursuant to Rule 115(1) EPC Dated Mar. 30, 2026 From the European Patent Office Re. Application No. 21792388.7. (7 Pages).
Notification of Office Action and Search Report Dated May 20, 2026 From the State Intellectual Property Office of the People's Republic of China Re. Application No. 202180043714.9 and Its Machine Translation Into English. (15 Pages).

* cited by examiner

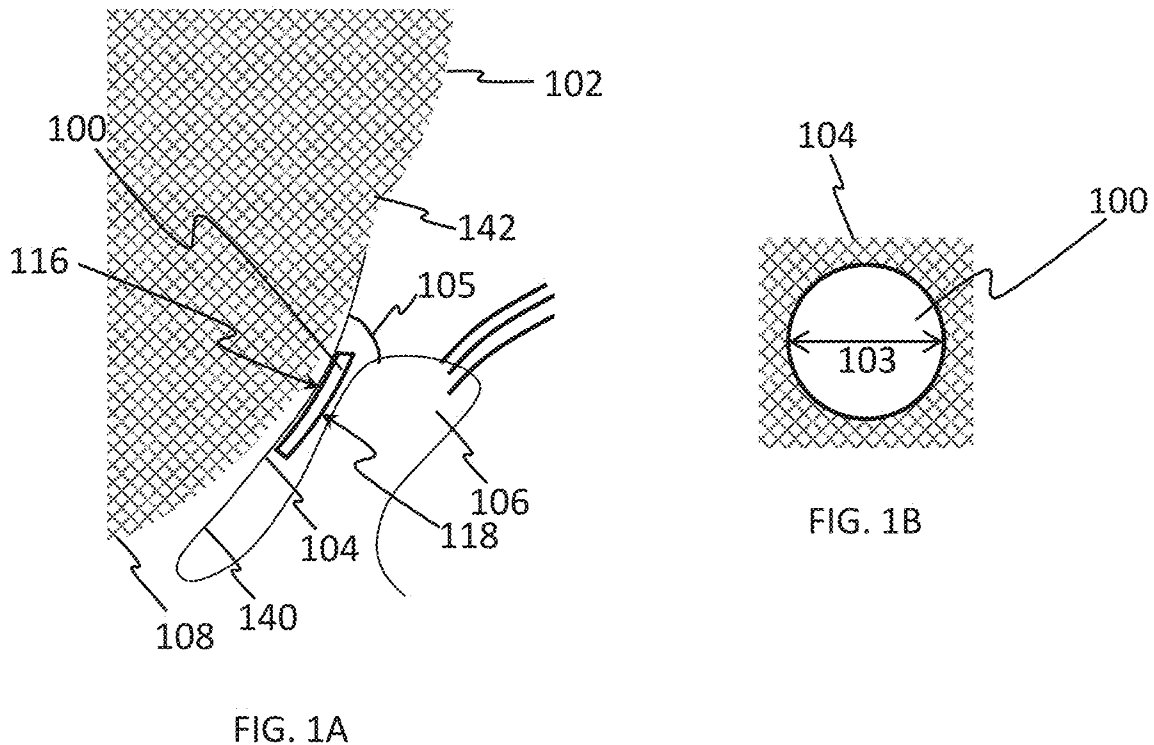
FIG. 1A
FIG. 1B
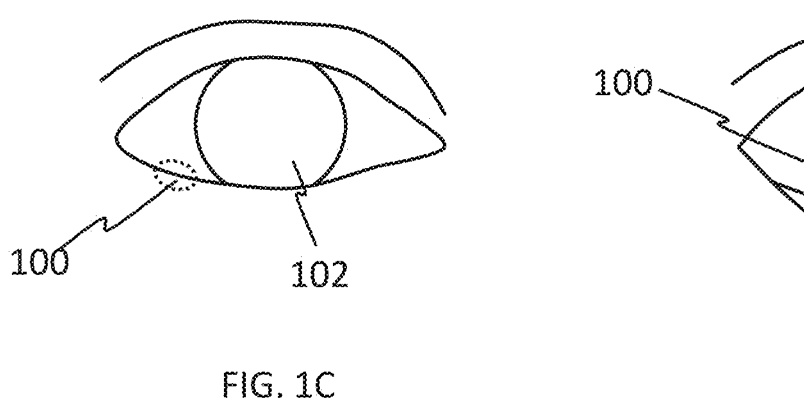
FIG. 1C
FIG. 1D

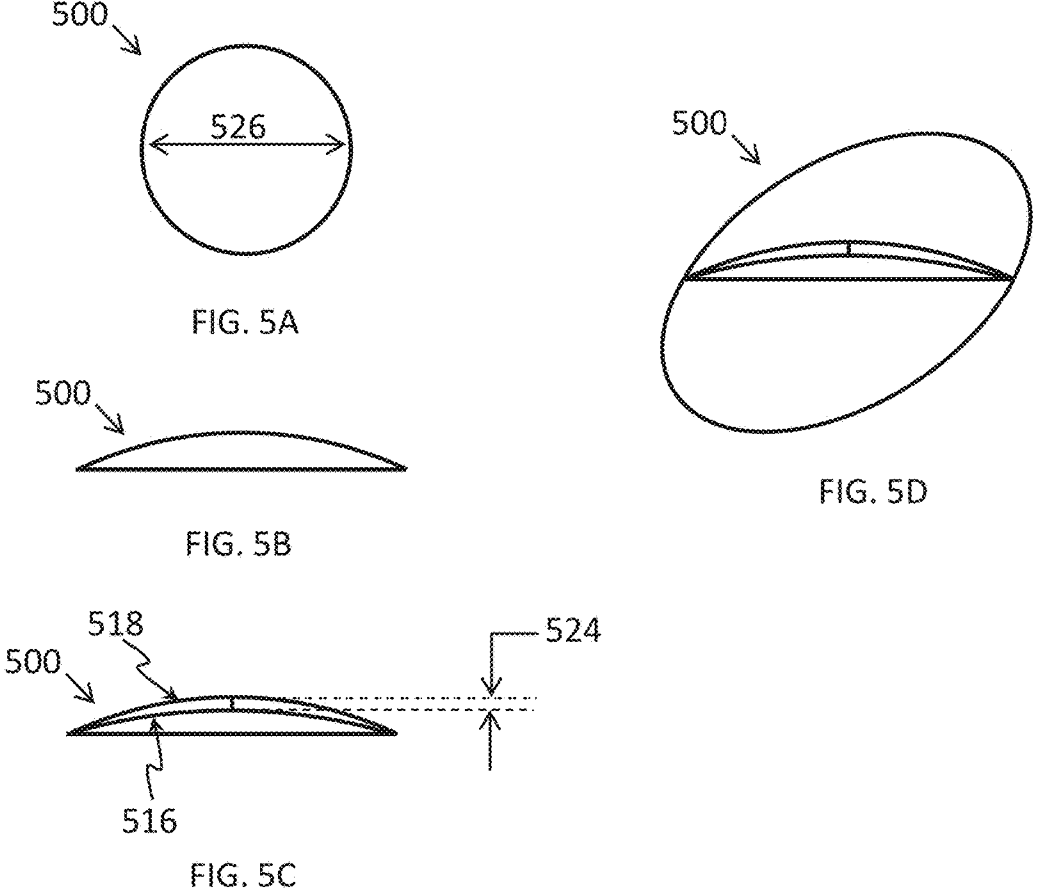
FIG. 5A
FIG. 5B
FIG. 5C
FIG. 5D
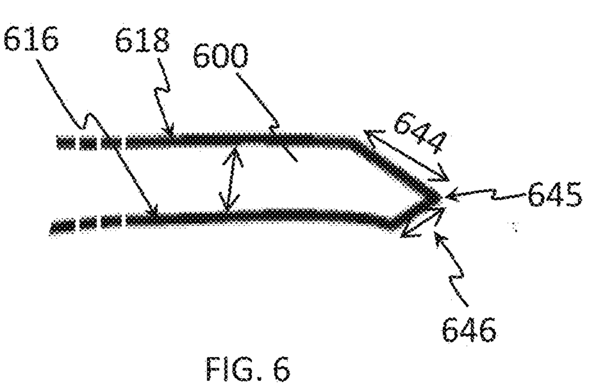
FIG. 6
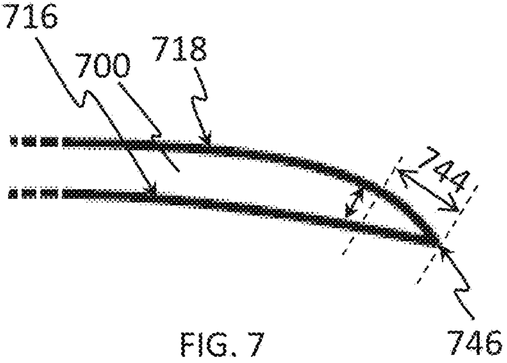
FIG. 7

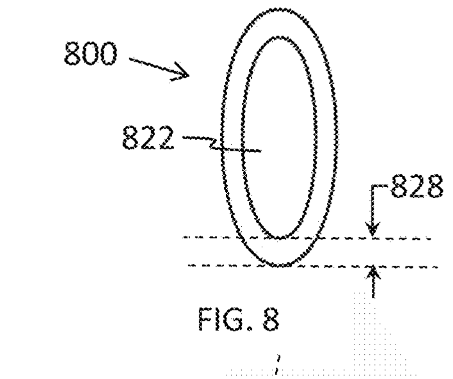
FIG. 8
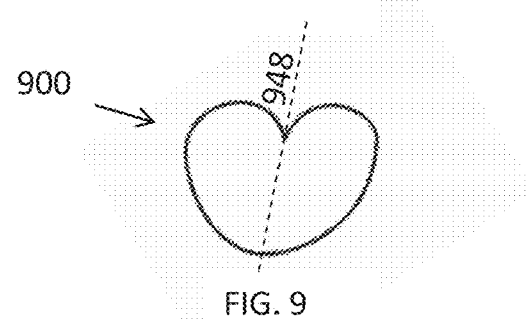
FIG. 9
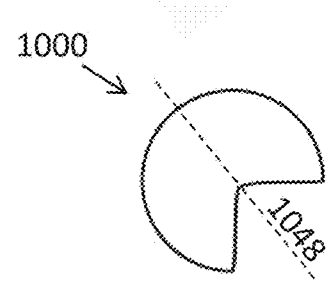
FIG. 10
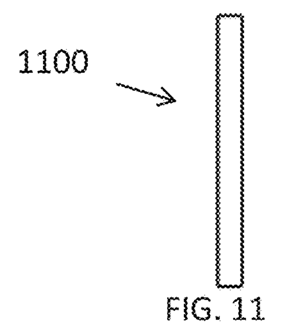
FIG. 11
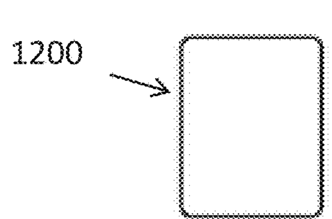
FIG. 12
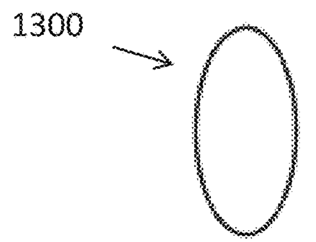
FIG. 13
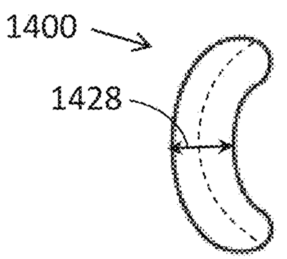
FIG. 14
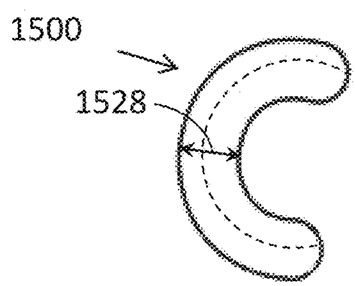
FIG. 15
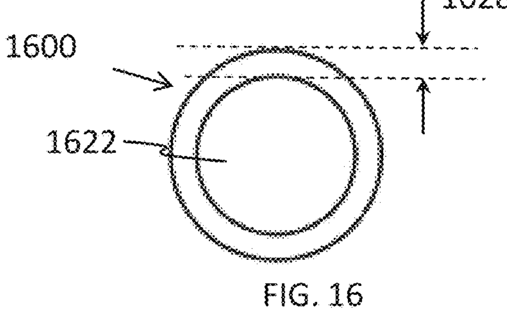
FIG. 16
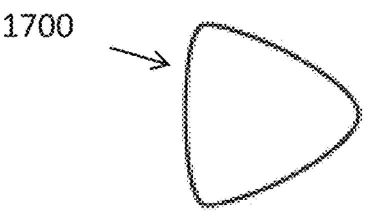
FIG. 17

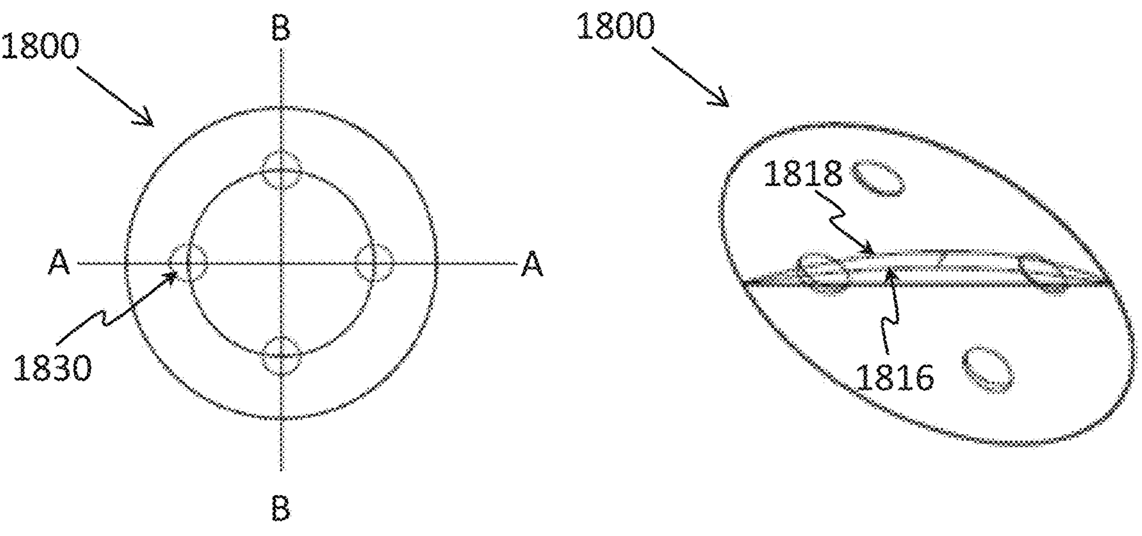
FIG. 18A
FIG. 18B
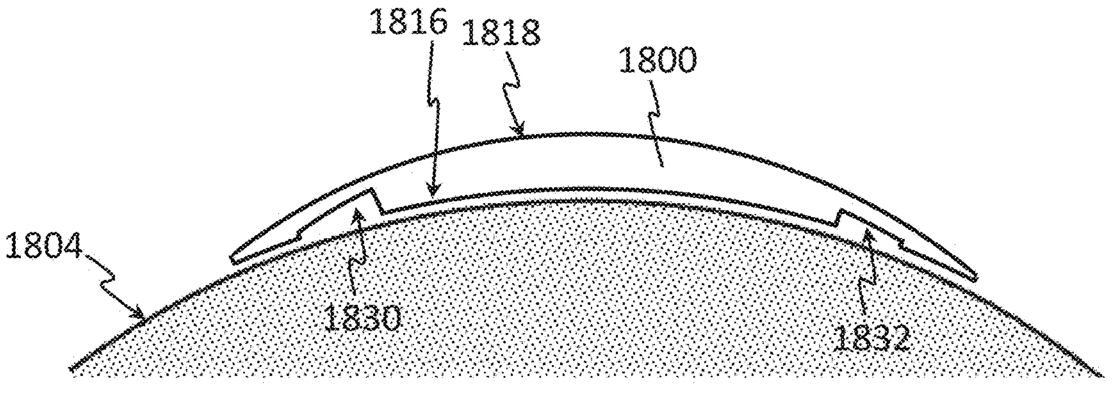
FIG. 18C
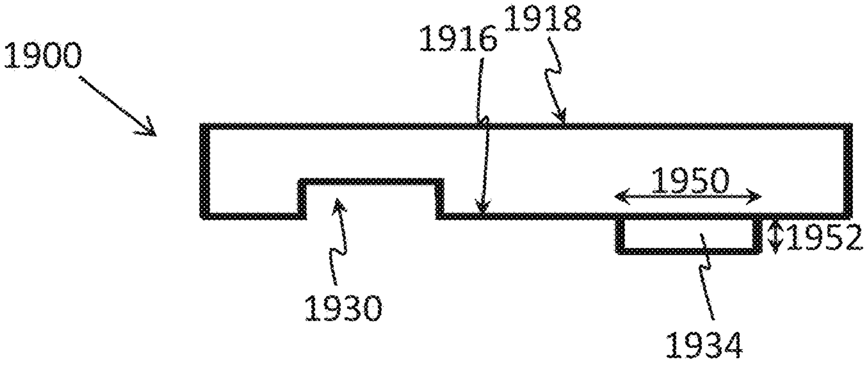
FIG. 19

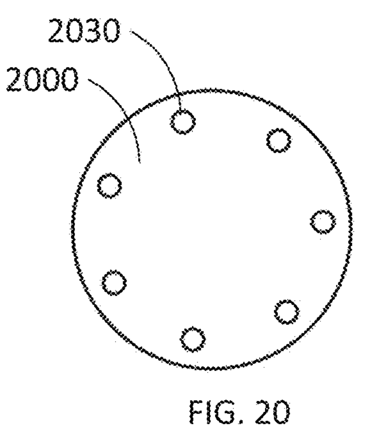
FIG. 20
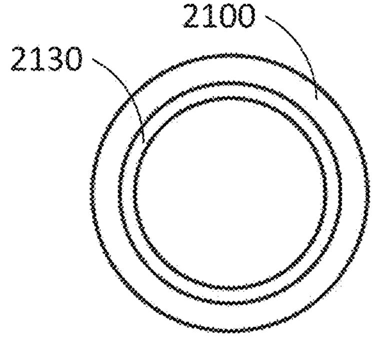
FIG. 21
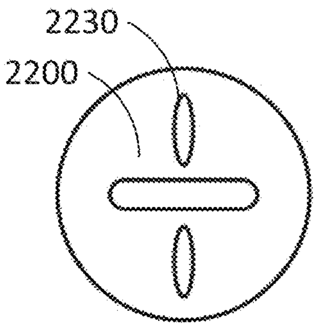
FIG. 22
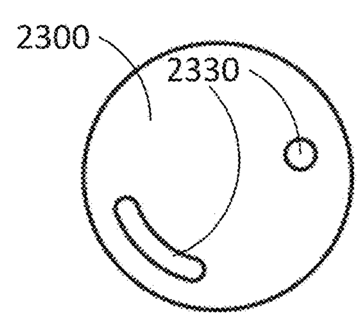
FIG. 23
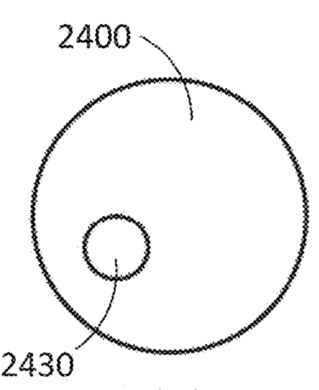
FIG. 24
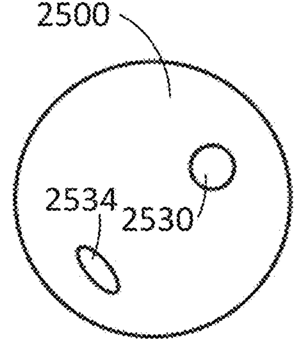
FIG. 25
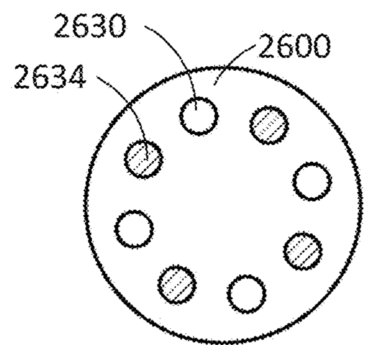
FIG. 26
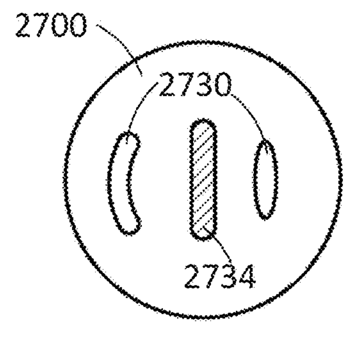
FIG. 27
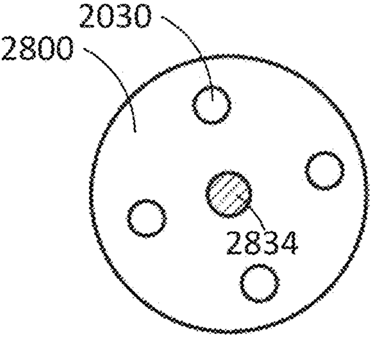
FIG. 28

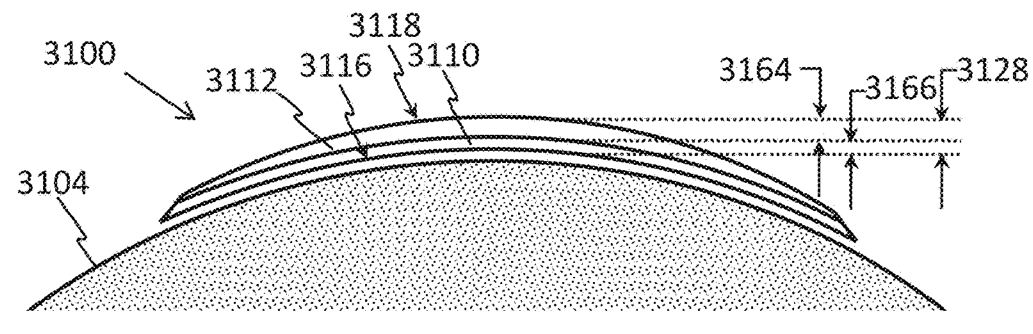
FIG. 31A
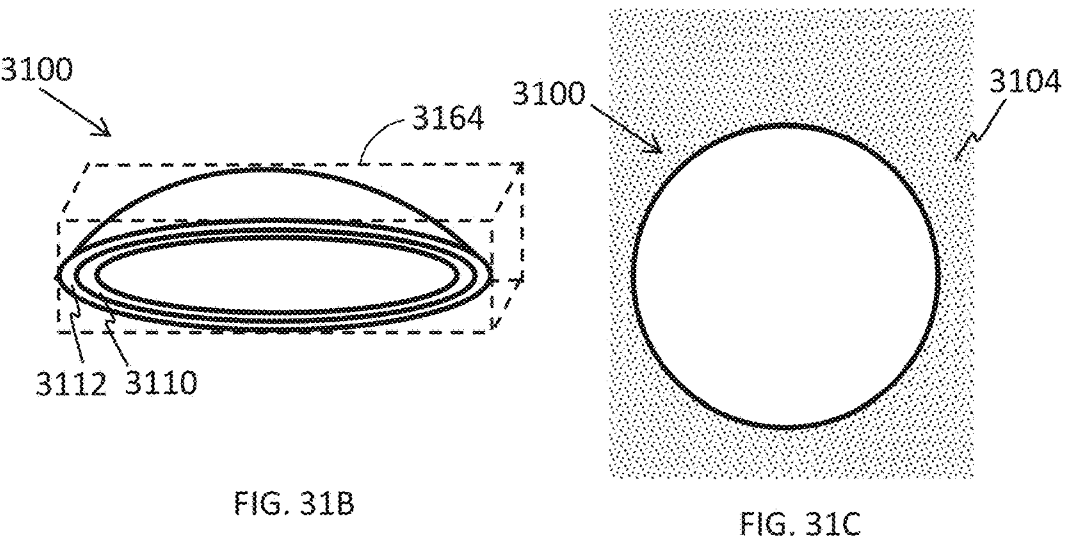
FIG. 31B
FIG. 31C
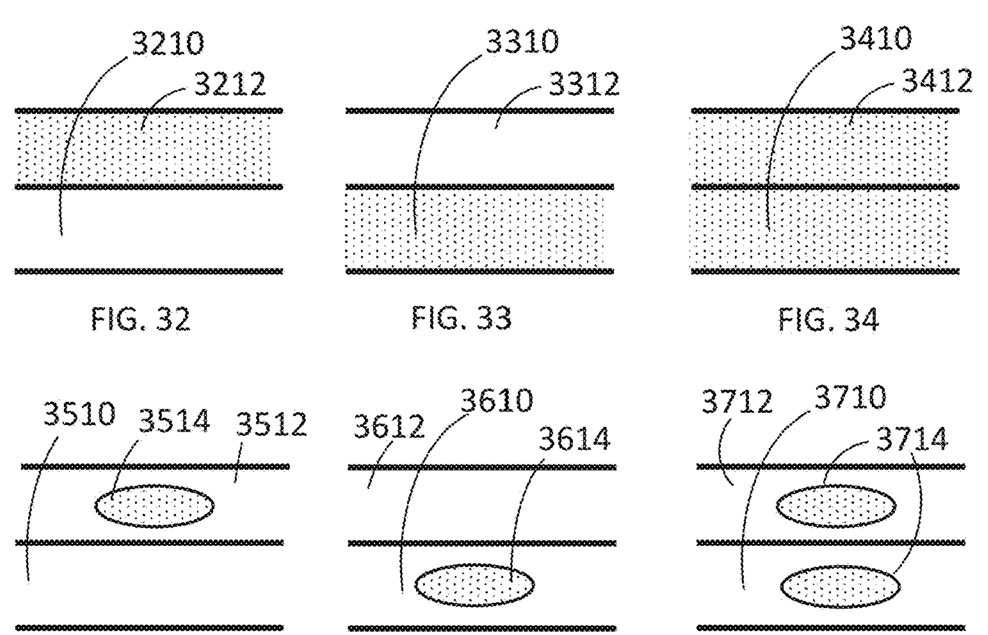
FIG. 32
FIG. 33
FIG. 34
FIG. 35
FIG. 36
FIG. 37

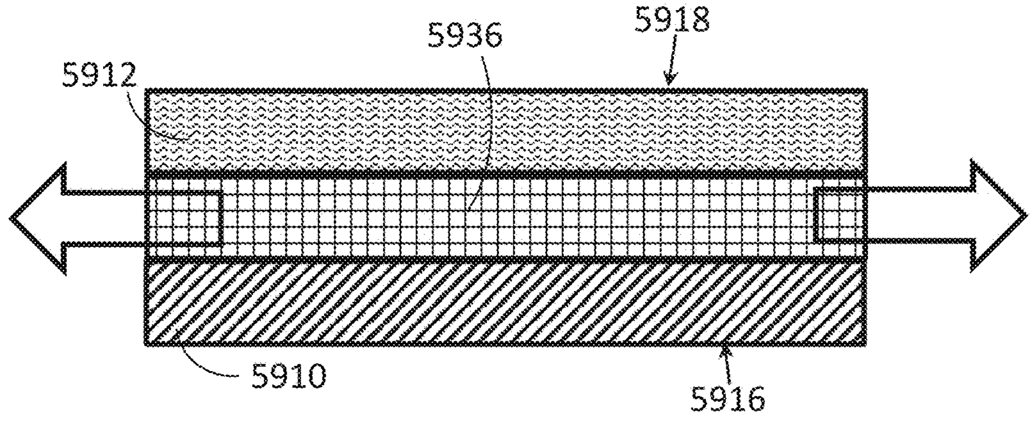
FIG. 59
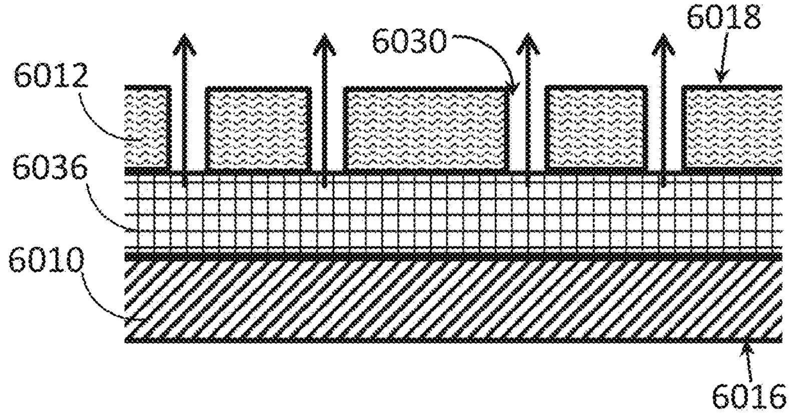
FIG. 60
6118
6112
6136
6110
6130
6116
FIG. 61

7190
7174

7190
7174
7176

7190
7178
7174

7190
7180
7178
7174

Make cavity/s in substrate
7200
Load cavity/ies
7202
Optionally, apply additional layer/s
7204

7190
7374

7190
7374

7190
7378
7374

7190
7378
7374

7300
7378
7374

7300
7378
7382
7374

OPHTHALMIC DEVICE

RELATED APPLICATIONS

This application is a National Phase of PCT Patent Application No. PCT/IL2021/050449 having International filing date of Apr. 20, 2021, which claims the benefit of priority under 35 USC § 119 (e) of U.S. Provisional Patent Application No. 63/012,388 filed on Apr. 20, 2020. The contents of the above applications are all incorporated by reference as if fully set forth herein in their entirety.

FIELD AND BACKGROUND OF THE INVENTION

The present invention, in some embodiments thereof, relates to an ophthalmic device and, more particularly, but not exclusively, to a drug eluting ophthalmic device.

"Ocular drug delivery conventional ocular formulations". Adv. Drug Delivery, 1995, 16: 39-43, to Lang, J. C. describes, apparently, that: Only about 5% of the drug applied as drops penetrate through the cornea and reaches the ocular tissue, while the rest is lost due to tear drainage. The drug mixes with the fluid present in the tear film upon instillation and has a short residence time of about 2-5 minutes in the film. About 5% of the drug gets absorbed and the remaining flows through the upper and the lower canaliculi into the lachrymal sac. The drug containing tear fluid is carried from the lachrymal sac into the nasolacrimal duct where the drug is absorbed reaching the bloodstream. This absorption leads to drug wastage and, the presence of certain drugs in the bloodstream leads to undesirable side effects. For example, as apparently described in TIMPOTIC® prescribing information, supplied by MERCK, beta-blockers such as Timolol that are used in the treatment of wide-angle glaucoma have a deleterious effect on heart.

Furthermore, for example as apparently described in "Patches, pumps and timed release", FDA Consumers magazine, October 1991 by Segal, M.: Application of ophthalmic drugs as drops results in a rapid variation in drug delivery rates to the cornea that limits the efficacy of therapeutic systems.

"Eye care in the intensive care unit", Journal of the Intensive Care Society 2018 to Benjamin J Hearne apparently describes that: Ocular surface disease is common in the intensive care population with 20-42% of patients developing corneal epithelial defects. Despite the scale of the problem, eye-care protocols are commonly not instigated, and documentation of eye care is often poor. Adherence to a correctly performed eye-care prevents the majority of corneal problems encountered in the intensive care unit. For example, management of conjunctivitis should be done by Chloramphenicol ointment that is applied in the eye four times a day for 5-7 days.

The use of ocular inserts of various shapes for treating eye disorders is apparently known.

U.S. Pat. No. 4,343,787 to Katz apparently describes the use of a water-soluble polymer to make a device which is inserted under the lower lid of the eye for treating dry eye syndrome.

U.S. Pat. No. 3,618,604 to Ness apparently describes: A generally crescent-shaped small article which fits under the lower lid and is used for dispersing drugs to the eye.

U.S. Pat. No. 5,137,728, to Bawa apparently describes: An insert with base curve that is steeper the eyeball radius of curvature, and more precisely less than 0.8 times the eyeball radius.

U.S. Pat. No. 7,579,019 to Tapolsky apparently describes: An insert having mucoadhesive layer. The mucoadhesive layer helps with attaching the device. Apparently, in the described design, the mucoadhesive layer tends to erode fast and apparently affecting the residence time of the device.

Additional background art includes U.S. Pat. Nos. 3,995, 635, 3,867,519; 3,828,777; 3,854,480; 4,571,039; 4,484, 922; 4,592,752;

Bourlais, C. L., Acar, L., Zia H., Sado, P. A., Needham, T., Leverge, R., "Ophthalmic drug delivery systems", Progress in retinal and eye research, 1998, 17, 1: 33-58;

"Formulation and characterization of atropine sulfate in albumin-chitosan microparticles for in vivo ocular drug delivery" to Richard T Addo et al, J Pharm Sci. 2015 May; 104(5):1677-90;

"Development of Water-Compatible Molecularly Imprinted Polymers Based on Functionalized β-Cyclodextrin for Controlled Release of Atropine" by Yahui He et al, Polymers 2020, 12(1), 130;

"Chitosan nanoparticles for prolonged delivery of timolol maleate" by Sunil A Agnihotri 1, Tejraj M Aminabhavi, Drug Dev Ind Pharm. 2007 November; 33(11):1254-62; and "Sustained delivery of timolol maleate from poly(lactic-co-glycolic acid)/poly(lactic acid) microspheres for over 3 months" by James P Bertram 1, Sandeep S Saluja, Jodi McKain, Erin B Lavik, J Microencapsul. 2009 February; 26(1):26,

SUMMARY OF THE INVENTION

Following is a non-exclusive list including some examples of embodiments of the invention. The invention also includes embodiments which include fewer than all the features in an example and embodiments using features from multiple examples, also if not expressly listed below.

Example 1. An ophthalmic device comprising:

a body having:

a posterior surface;

an anterior surface;

wherein a size of said body, a shape of said posterior surface, and a shape of said anterior surface configures said device to reside on a bulbar conjunctiva of an eye.

Example 2. The device according to example 1, wherein, when in residence on said bulbar conjunctiva, said posterior surface is adjacent to said bulbar conjunctiva and said anterior surface is adjacent to an inner eyelid surface, at least periodically.

Example 3. The device according to any one of examples 1-2, wherein said body comprises therapeutic material and is configured to elute the therapeutic material into said eye when residing on said bulbar conjunctiva.

Example 4. The device according to any one of examples 1-3, wherein an extent of said body is 2-8 mm.

Example 5. The device according to any one of examples 1-4, wherein a thickness of said body is less than 400 microns.

Example 6. The device according to any one of examples 1-5, wherein an edge region of said body, at less than 0.5 mm from an edge of said body, has a thickness of less than 50 microns.

Example 7. The device according to any one of examples 1-6, wherein said posterior surface is concave.

Example 8. The device according to any one of examples 1-7, wherein a ratio of a radius of curvature of said posterior surface to a radius of curvature of a sclera of said eye is larger than 0.8.

Example 9. The device according to any one of examples 1-8, wherein a radius of curvature of said posterior surface is 9-11 mm.

Example 10. The device according to any one of examples 1-9, wherein a softness of said device is 0.3-1.5 Mpa.

Example 11. The device according to any one of examples 1-10, wherein said anterior surface is convex.

Example 12. The device according to any one of examples 1-11, wherein a radius of curvature of said anterior surface is smaller than a radius of curvature of said posterior surface.

Example 13. The device according to any one of examples 1-12, wherein said device is configured to reside on said bulbar surface for at least 15 minutes.

Example 14. The device according to any one of examples 1-13, wherein said bulbar conjunctiva is a portion of conjunctiva between the cornea and the conjunctiva of a fornix.

Example 15. The device according to any one of examples 1-14, wherein said bulbar conjunctiva is a portion of conjunctiva which coincides with a tear meniscus.

Example 16. The device according to any one of examples 1-15, wherein said posterior surface comprises mucoadhesive material.

Example 17. The device according to any one of examples 1-16, wherein said anterior surface has a smooth surface and/or comprises lubricious material.

Example 18. The device according to any one of examples 1-17, wherein said body comprises material which disintegrates within an eye.

Example 19. The device according to any one of examples 1-18, wherein said body comprises one or both of biodegradable and bioerodable material.

Example 20. The device according to any one of examples 1-19, wherein said posterior surface comprises one or more cavity.

Example 21. The device according to any one of examples 1-20, wherein said posterior surface comprises on or more protrusion.

Example 22. The device according to any one of examples 1-21, wherein said device comprises one or more electronic element.

Example 23. The device according to any one of examples 1-22, wherein said device is supplied in dry or semi-hydrated form.

Example 24. The device according to any one of examples 1-23, wherein said device hydrates on said bulbar surface.

Example 25. The device according to any one of examples 1-24, wherein said body comprises more than one layer with different material characteristics.

Example 26. The device according to any one of examples 1-25, wherein said body comprises one or more of:

Hydroxy Propyl Cellulose (HPC); Hydroxy Propyl Methyl Cellulose (HPMC); Carboxymethyl cellulose (CMC); PolyVinyl Alcohol (PVOH); PolyEthylene Glycol (PEG); Cellulose Acetate (CA); Polyvinyl alcohol-polyethylene glycol graft-copolymer (Kollicoat); Poly Acrylic Acid (Carbopol or Carbomer for example); Hyaluronic Acid; Ethyl cellulose; Tri Ethyl Citrate (TEC); Glycerol; Dextran; and combinations thereof.

Example 27. The device according to any one of examples 1-26, where said device comprises one or more anchor configured to hold said device on said bulbar conjunctiva.

Example 28. The device according to example 27, wherein said anchor comprises sharp edges of said body.

Example 29. The device according to example 28, wherein a radius of curvature of said edges is less than 100 microns.

Example 30. The device according to any one of examples 1-29, wherein said posterior surface is rough.

Example 31. An ophthalmic device comprising:

a body configured to reside on a bulbar conjunctiva having:

a concave posterior surface having a posterior surface radius of curvature where a ratio of said radius of curvature of said posterior surface is to a curvature of a sclera of an eye is greater than 0.8.

Example 32. An ophthalmic device comprising:

a body configured to reside on a bulbar conjunctiva having:

an extent of 2-8 mm; and an edge region, at less than 0.5 mm from an edge of said body, with a thickness of less than 50 microns.

Example 33. A method comprising:

applying an ophthalmic device to a bulbar conjunctiva of an eye;

performing daily activities for a time period during which said ophthalmic device remains in residence on said bulbar conjunctiva of said eye.

Example 34. The method according to example 33, wherein said performing comprises without experiencing ocular discomfort.

Example 35. The method according to any one of examples 33-34, wherein said device remains in position during blinking and tearing.

Example 36. The method according to any one of examples 33-35, wherein, during blinking, a step between an edge of said device and said bulbar conjunctiva deflects an eyelid outwards from the bulbar conjunctiva surface, by at most 400 microns.

Example 37. The method according to any one of examples 33-36, wherein said device moves by at most 0.5 mm from a residence position on said bulbar conjunctiva.

Example 38. The method according to any one of examples 33-37, wherein said applying comprises applying pressure to said device when said device in in contact with said bulbar conjunctiva.

Example 39. The method according to any one of examples 33-38, comprising removing said device from said eye after said residence time period.

Example 40. The method according to any one of examples 33-39, comprising expelling said device.

Example 41. The method according to any one of examples 33-40, comprising applying an additional ophthalmic device.

Example 42. The method according to example 41, wherein said applying is during or after said residence time.

Example 43. A method of treatment comprising:

covering a portion of a bulbar conjunctiva with an ophthalmic device, for a residence time period.

Example 44. The method according to example 43, wherein said residence time period is 1 hour to 1 week.

Example 45. The method according to any one of examples 43-44, comprising eluting medication from a body of said ophthalmic device into one or both of tear fluid and eye tissue.

Example 46. The method according to any one of examples 43-45, comprising adhering said ophthalmic device to said bulbar conjunctiva.

Example 47. The method according to example 46, wherein said adhering includes mucoadhesive adhering between a posterior surface of said device and said bulbar conjunctiva.

Example 48. The method according to any one of examples 46-47, wherein said adhering comprises suction provided by surface tension forces generated by a difference in curvature between a posterior surface of said device and said bulbar conjunctiva.

Example 49. The method according to any one of examples 46-48, wherein said adhering comprises anchoring said device by recessing edges of said device into said bulbar conjunctival.

Example 50. The method according to any one of examples 46-49, wherein said adhering comprises suction, under surface tension forces, of one or more portion of said bulbar conjunctiva towards and/or into one or more cavity of a posterior surface of said device.

Example 51. The method according to any one of examples 46-50, wherein said adhering comprises anchoring said device by recessing one or more portion of said bulbar conjunctiva away from one or more protrusion disposed on a posterior surface of said device.

Example 52. The method according to any one of examples 43-51, comprising degrading said device during said residence period by exposing said device to tear fluid and movement of eyeball and eyelids.

Example 53. The method according to example 52, wherein said degrading reduces adherence of said device to said bulbar conjunctiva.

Example 54. The method according to any one of examples 52-53, wherein said degrading comprises said device disintegrating into parts smaller than an initial extent of said device.

Example 55. A method comprising:

applying an ophthalmic device in a dry or partially hydrated form to an eye surface;

hydrating said device within said eye.

Example 56. The method according to example 55, wherein said hydrating is by one or more of: eye tear fluid, and applying hydrating fluid to said eye.

Example A. An ocular device having a posterior surface and an anterior surface and having one or more cavities open to the posterior surface.

Example B. An ocular device according to Example A, for protection or for treatment purposes.

Example C. An ocular device of any one of Examples A-B, which contains therapeutic agent or other compounds.

Example D. An ocular device of any one of Examples A-C, having a mucoadhesive posterior surface.

Example E. An ocular device of any one of Examples A-D, having a lubricious anterior surface.

Example F. An ocular device of any one of Examples A-E, having an edge design for comfort or for tightness.

Example G. An ocular device of any one of Examples A-F, having one or more protrusions on the posterior surface.

Example H. An ocular device of any one of Examples A-G, intended to be inserted to the eye.

Example I. An ocular device of any one of Examples A-H, is biodegradable or bioerodible.

Example J. An ocular device of any one of Examples A-I, with a thickness not greater than 200 microns.

Example K. An ocular device of any one of Examples A-J, in dry form

Example L. An ocular device of any one of Examples A-K, configured for the release of drugs while in the eye/on the cornea without interfering the patient vision.

Example M. An ocular device of any one of Examples A-L, designed to adhere to the sclera, cornea, limbus or the conjunctiva Unless otherwise defined, all technical and/or scientific terms used herein have the same meaning as commonly understood by one of ordinary skill in the art to which the invention pertains. Although methods and materials similar or equivalent to those described herein, in some embodiments is used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1A is a simplified schematic cross sectional view of an ophthalmic device in position on an eye, according to some embodiments of the invention;

FIG. 1B is a simplified schematic top view of an ophthalmic device in position on an eye, according to some embodiments of the invention;

Figures 2, 3:
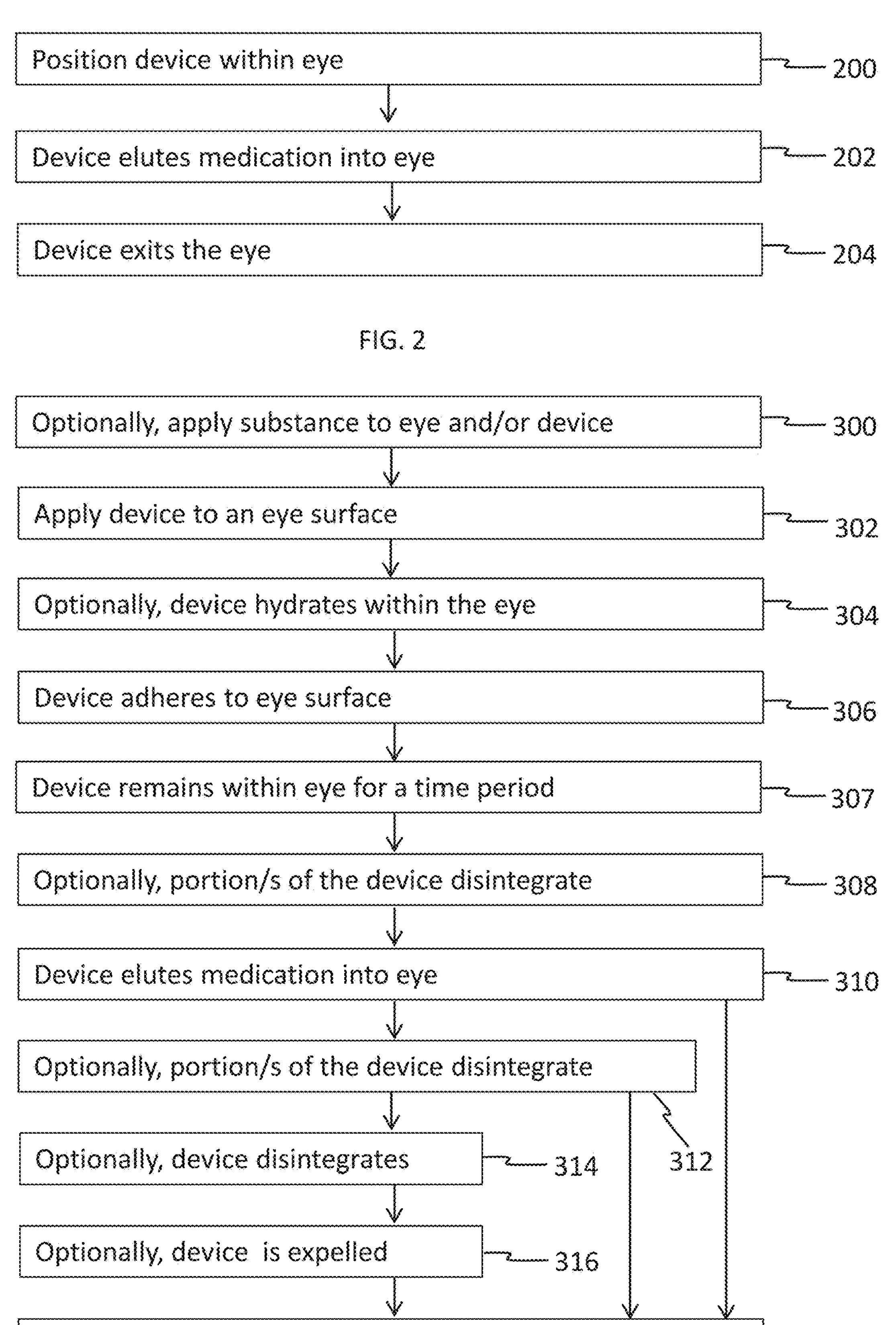
Figure 4:
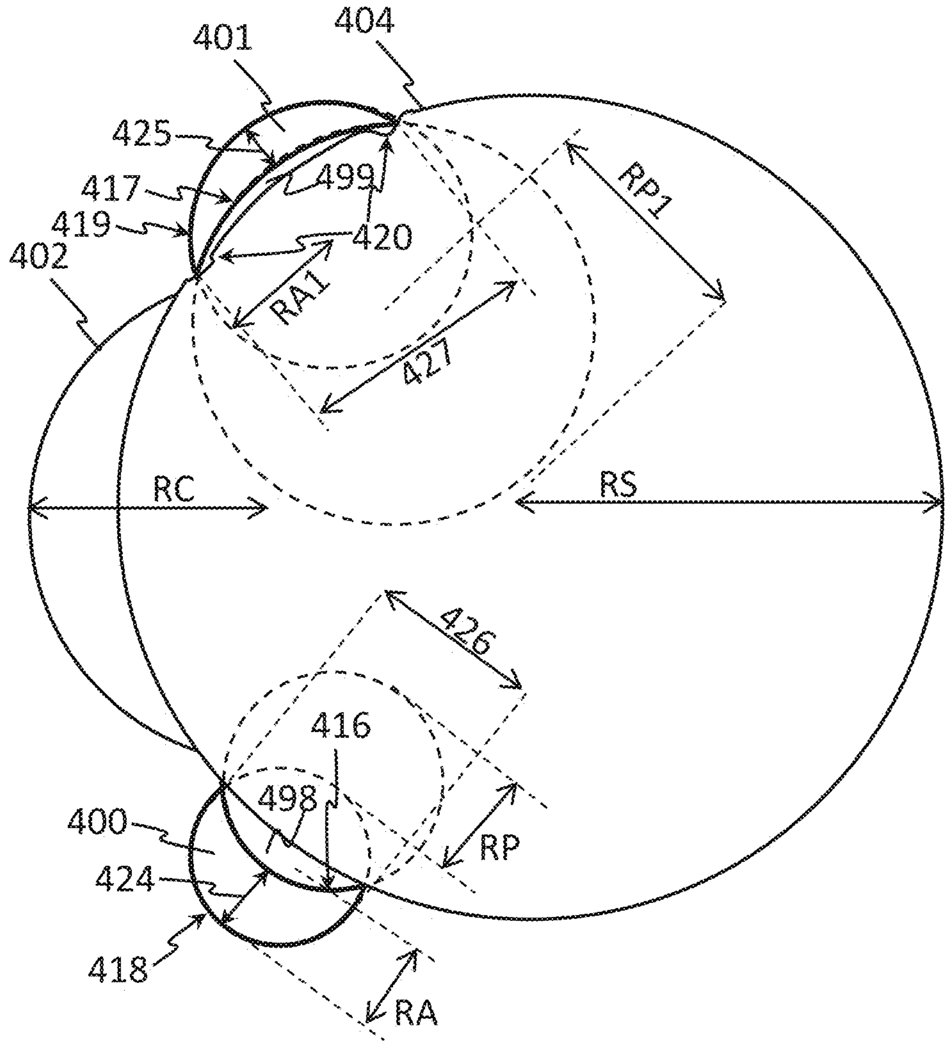
Figure 29A:
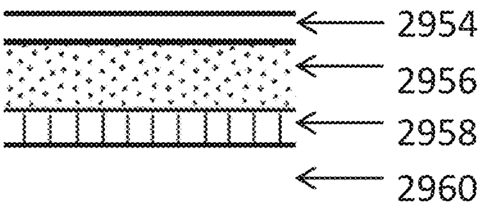
Figure 29B:
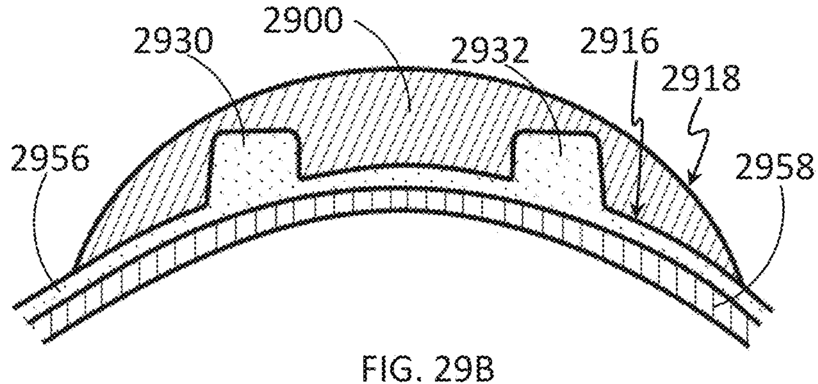
Figure 29C:
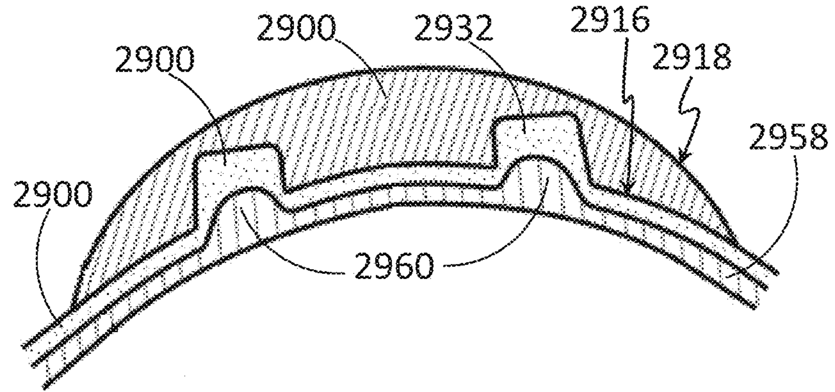
Figure 30A:
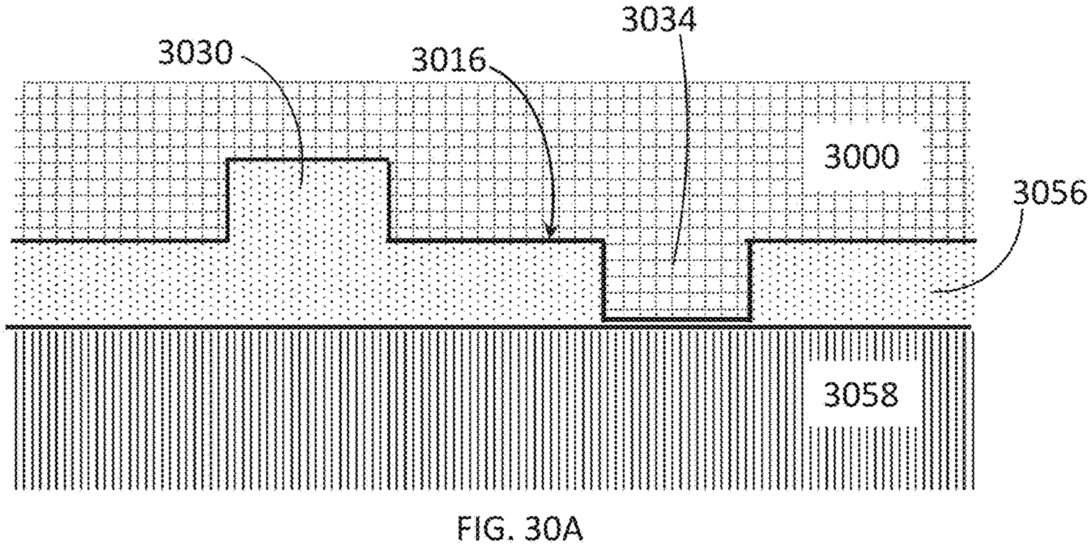
Figure 30B:
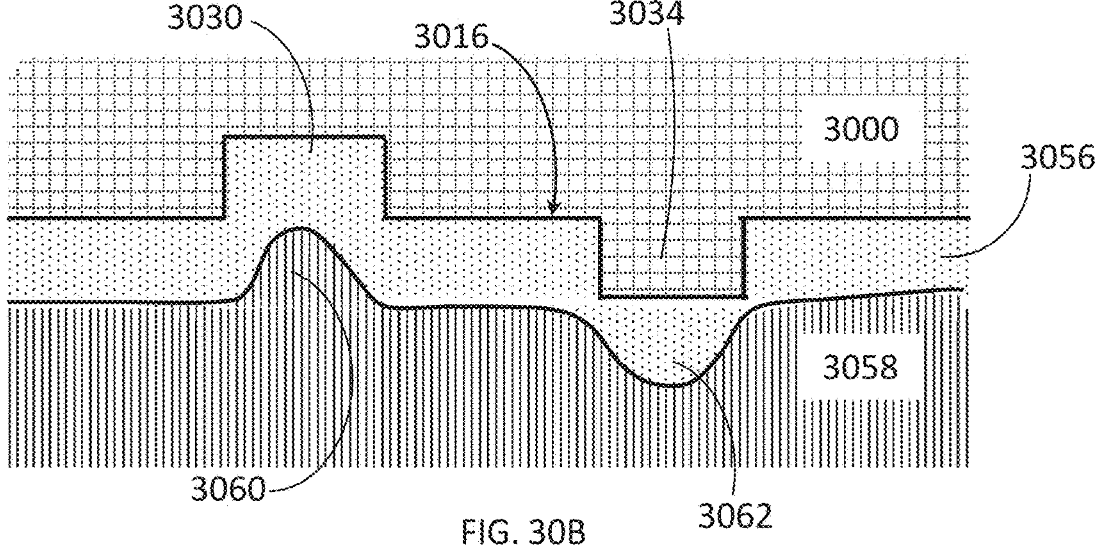
Figure 30C:
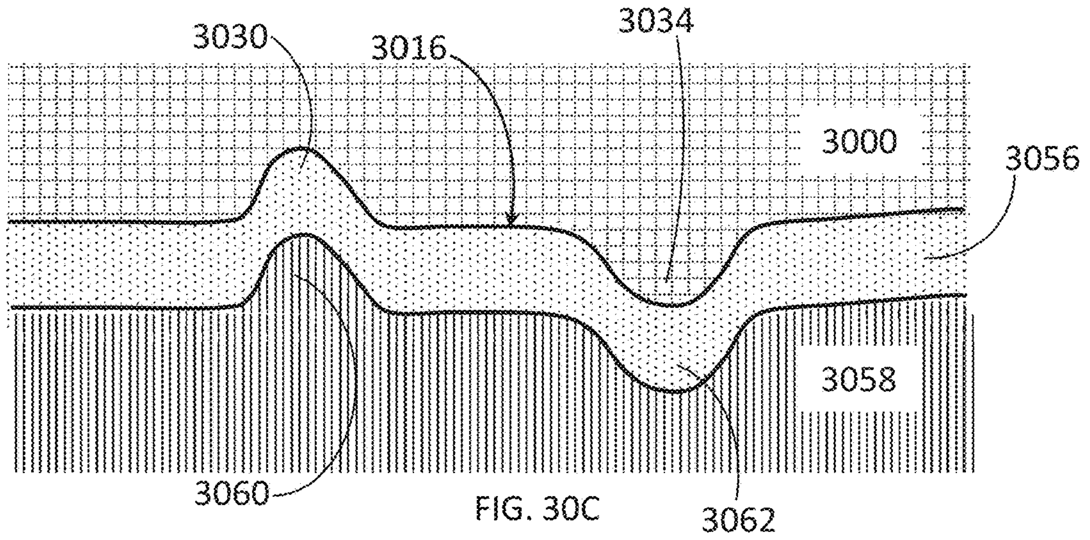
Figure 63:
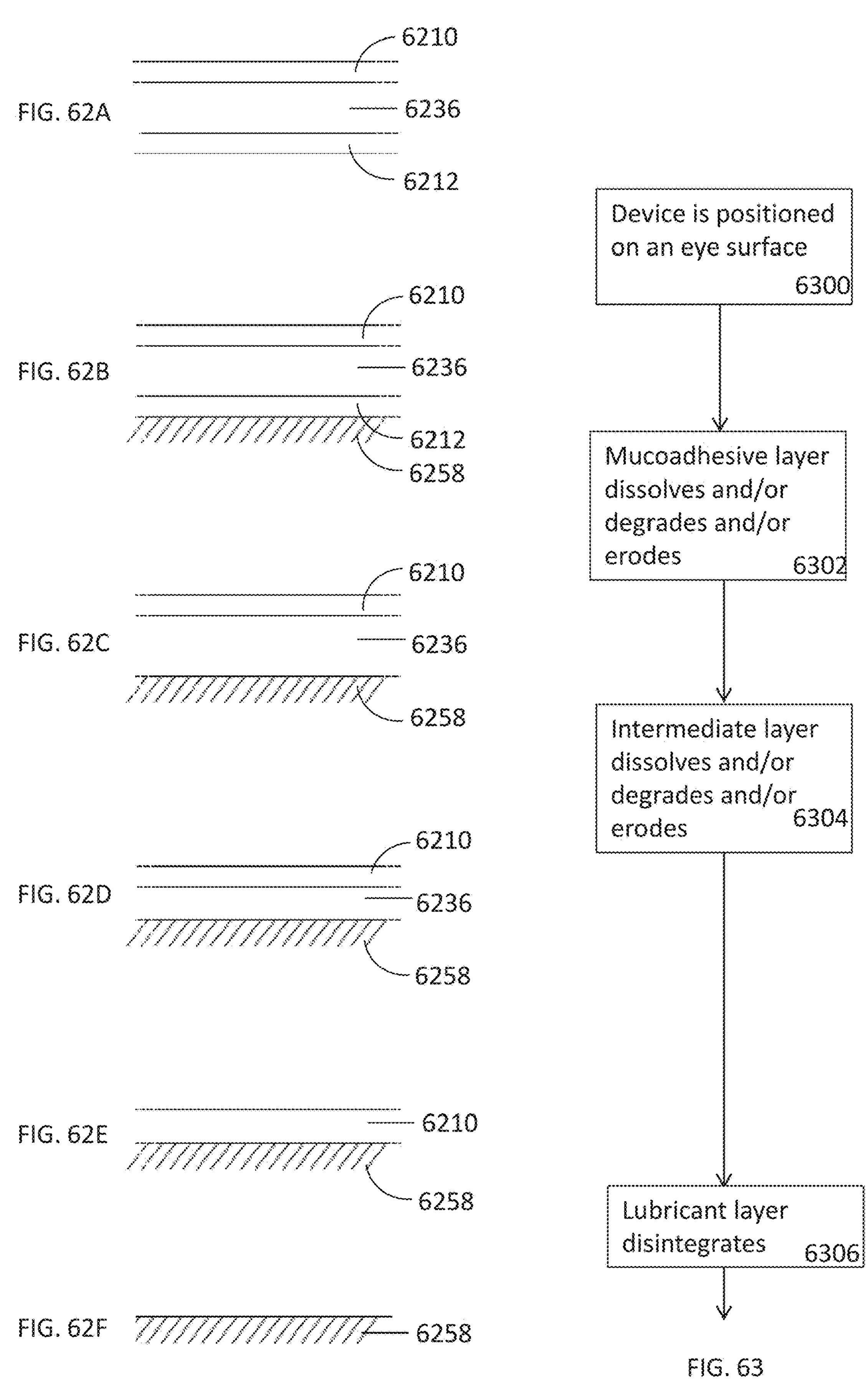
Figures 64A, 64B, 64C, 65A, 65B, 65C, 65D, 66, 67:
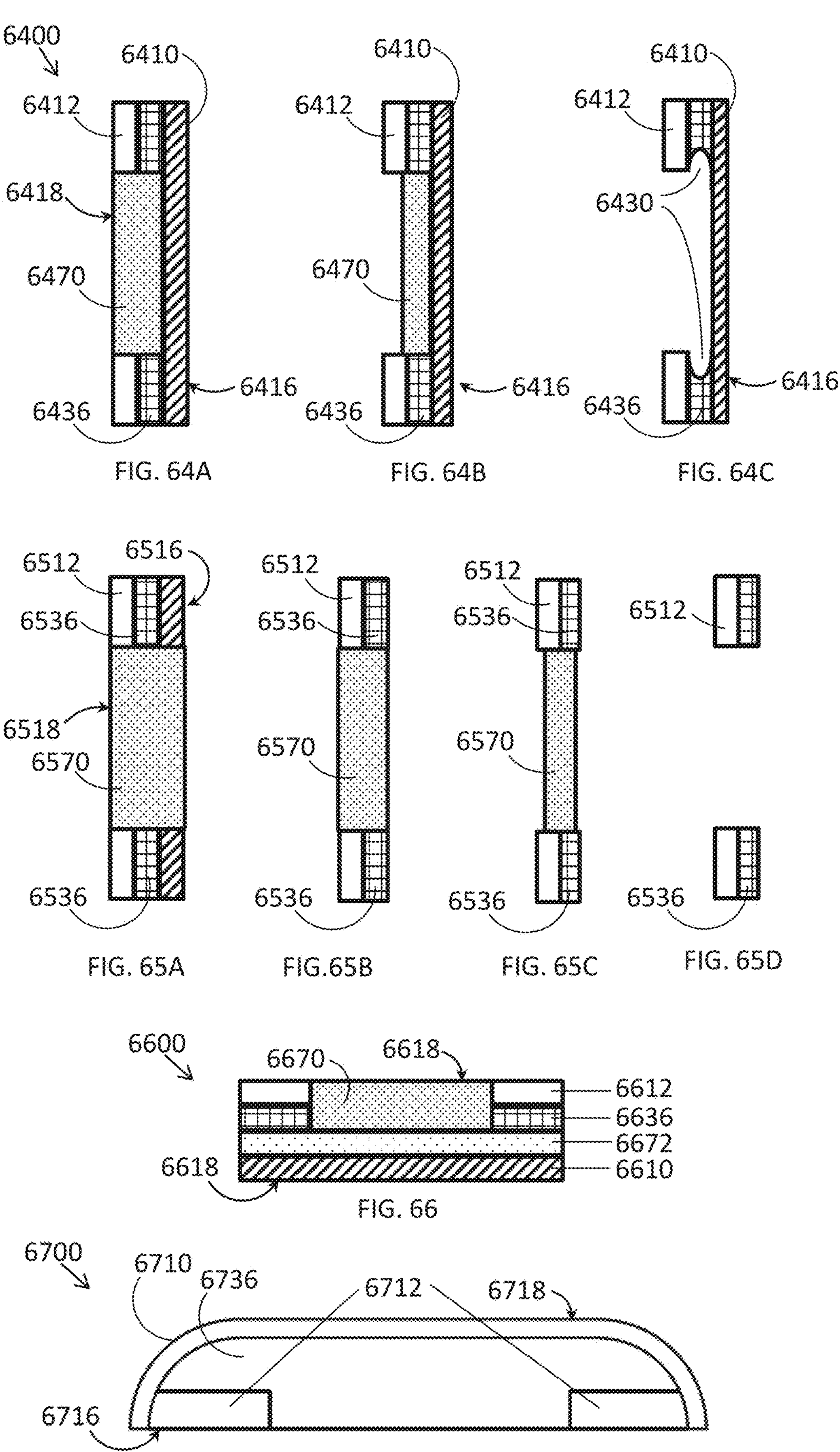
Figure 68A:
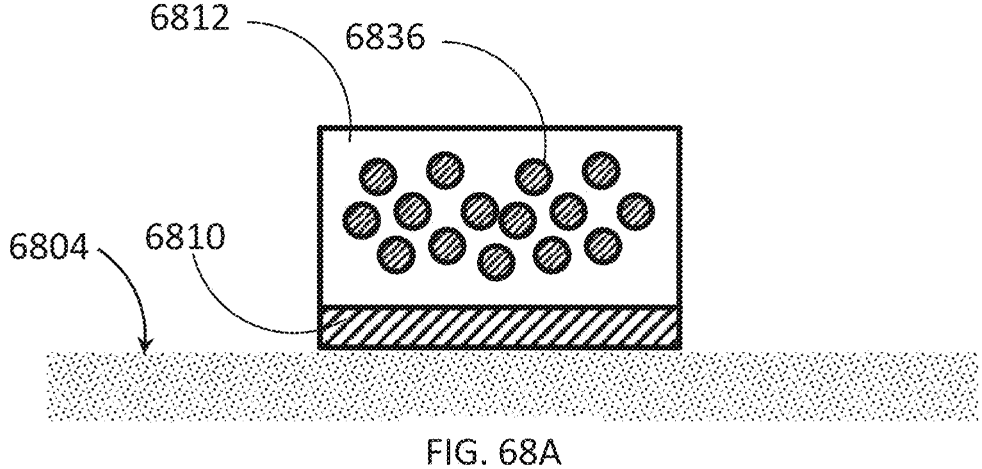
Figure 68B:
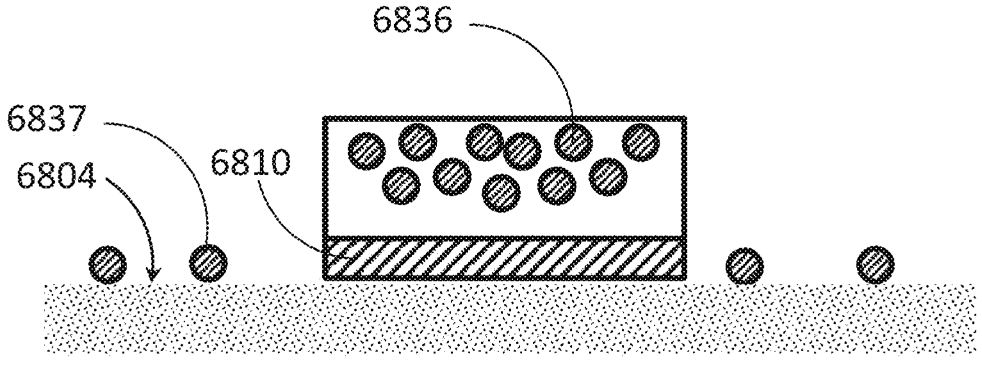
Figure 69:
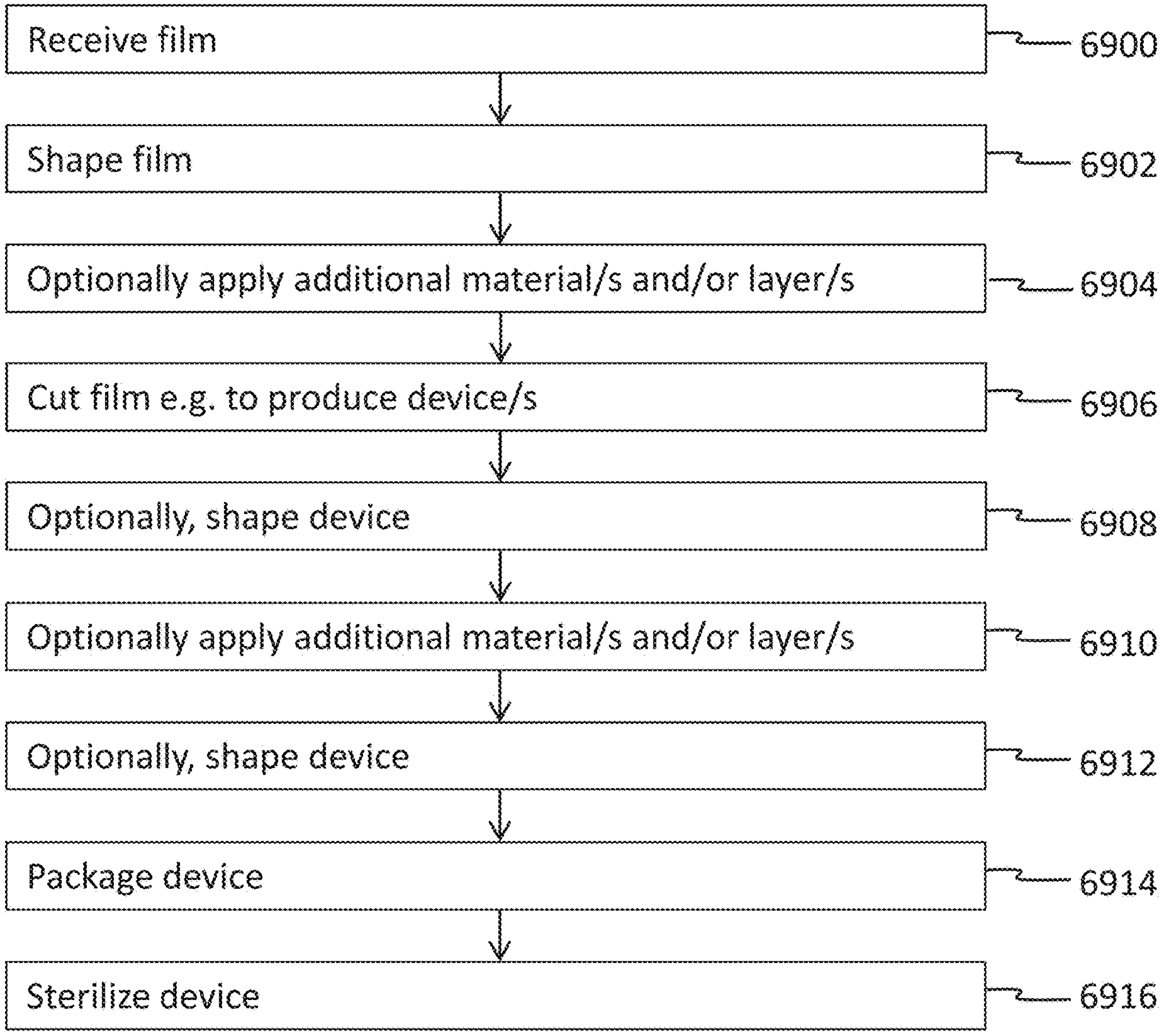
Figure 70:
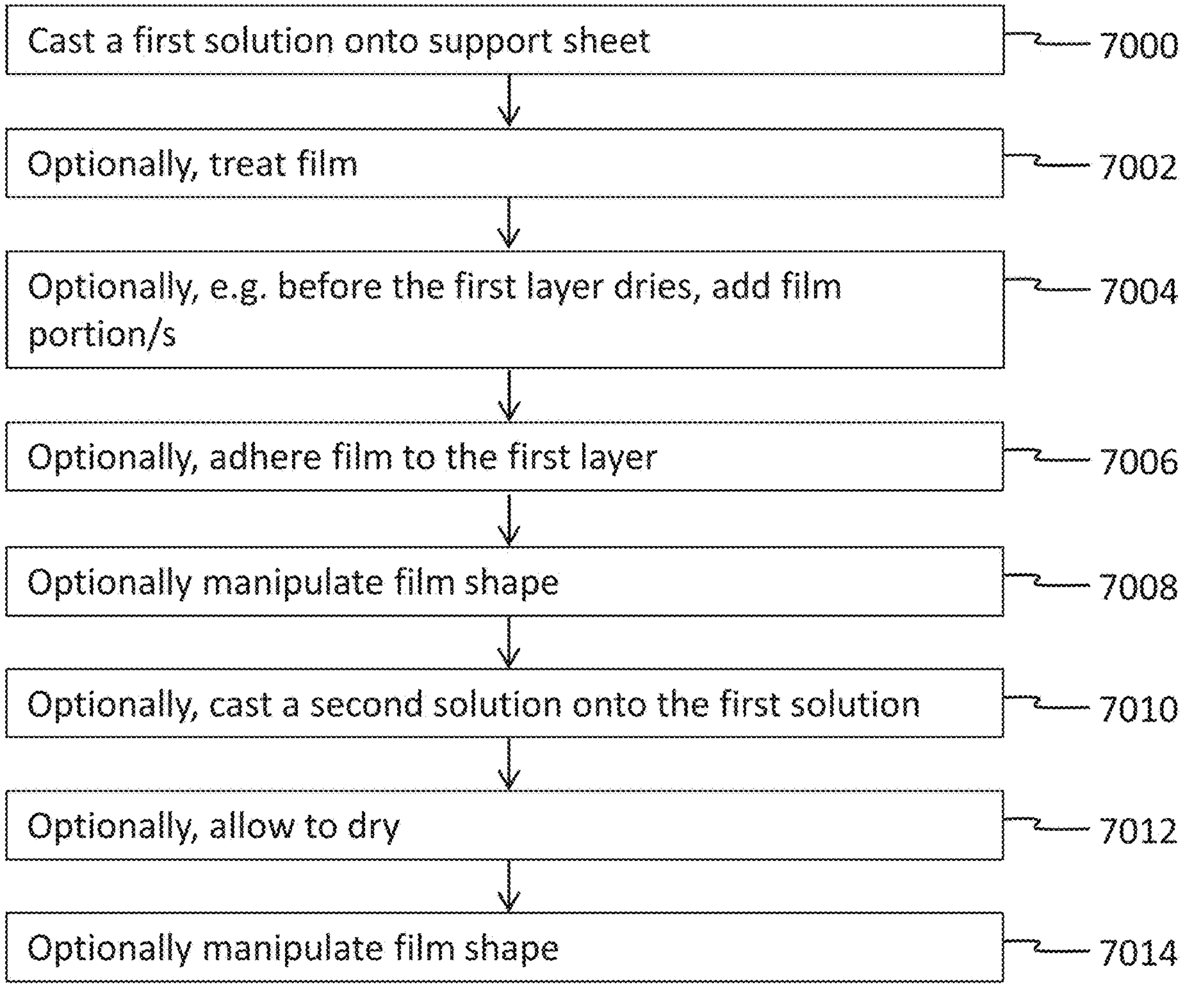
Figures 71A, 71B, 71C, 71D, 72:
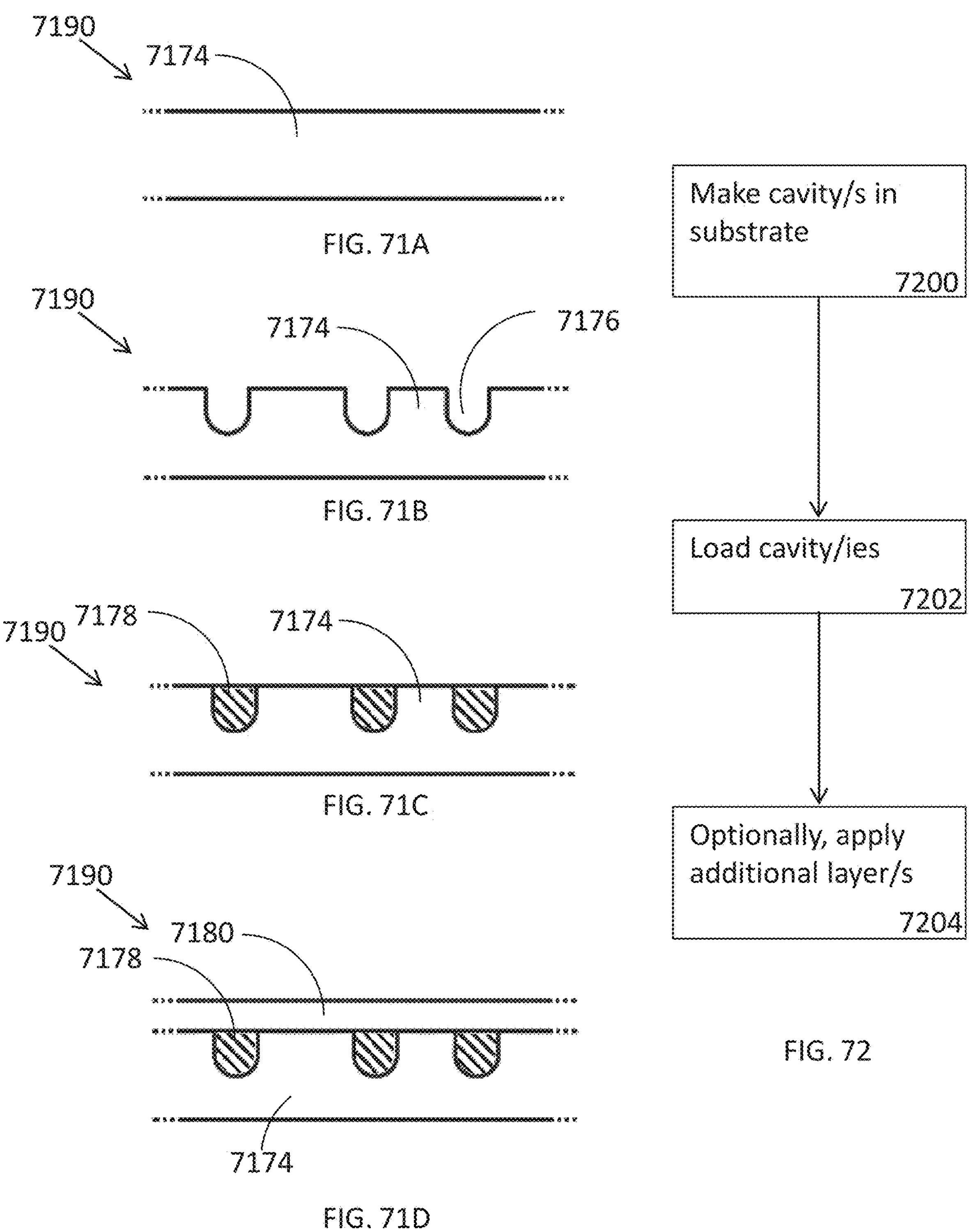
Figures 73A, 73B, 73C, 73D, 73E, 73F:
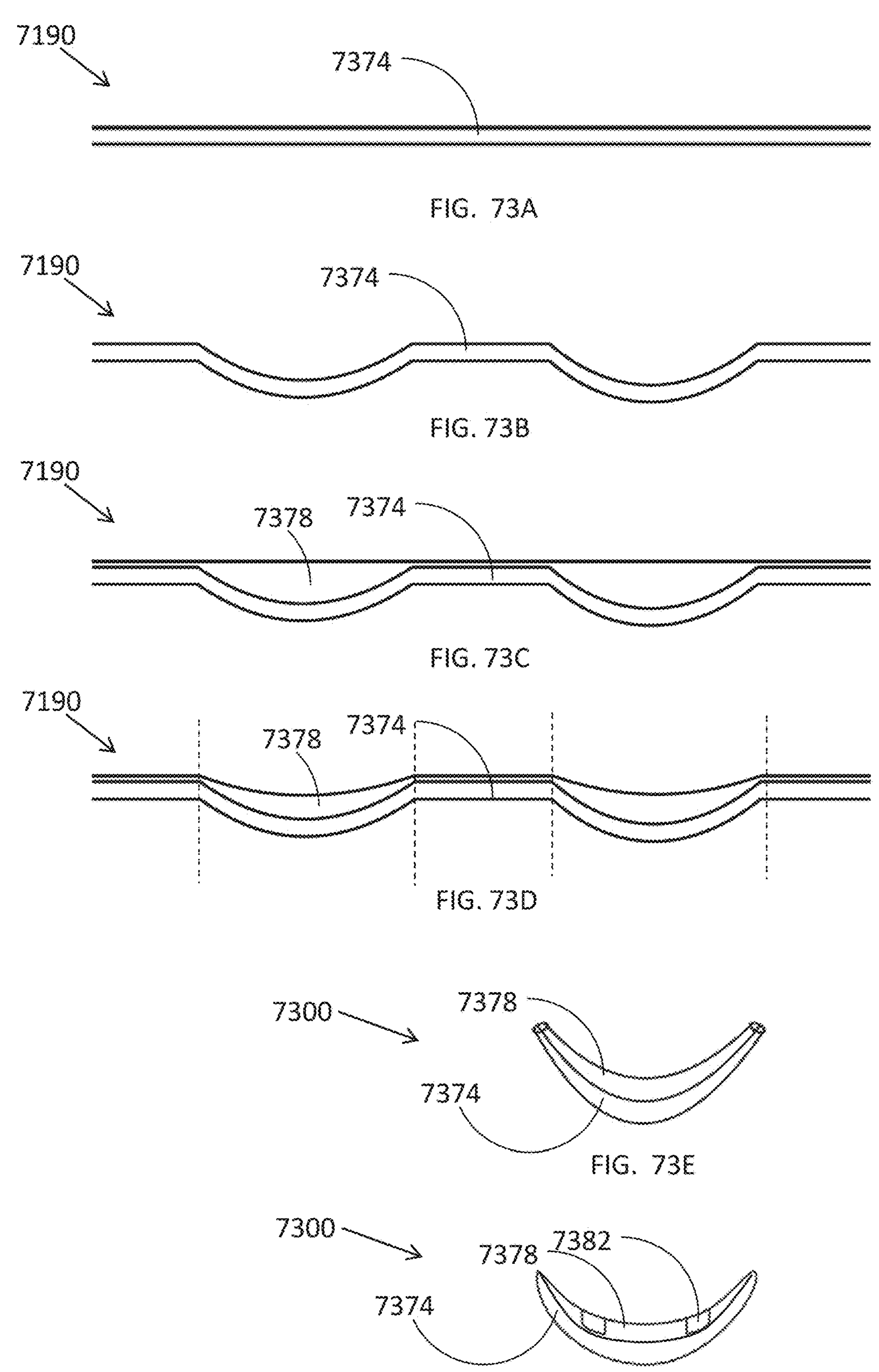
Figure 74A:
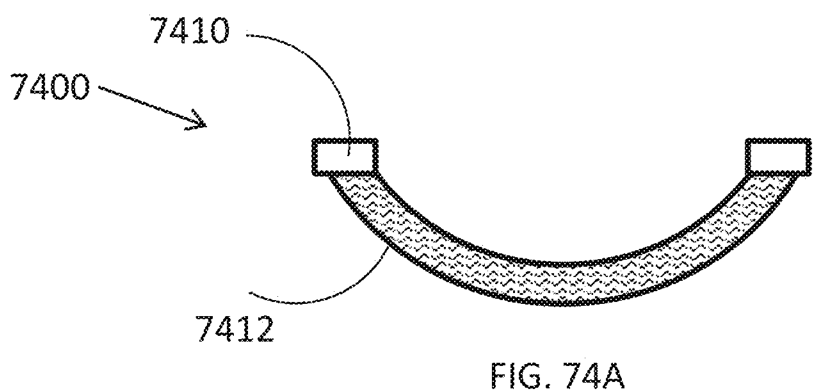
Figure 74B:
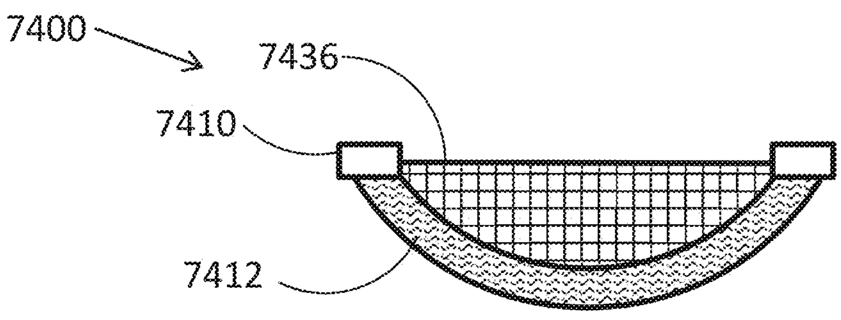
Figure 74C:
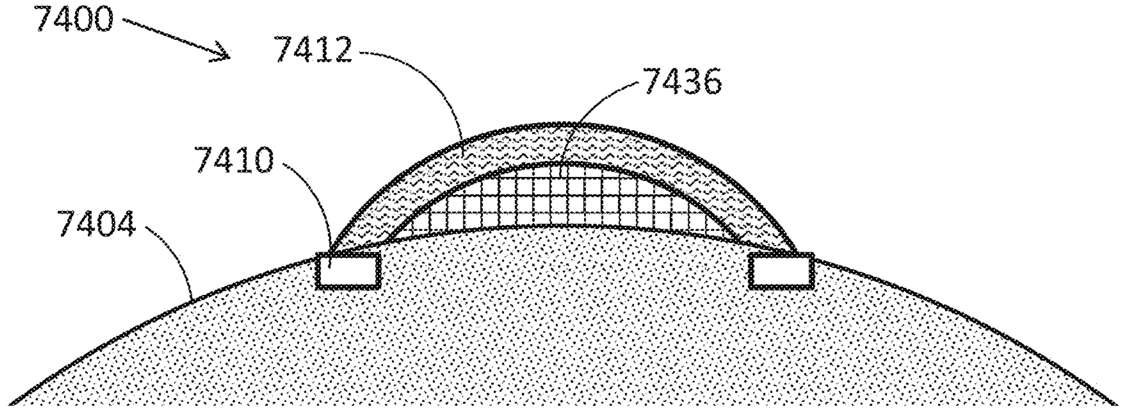

FIGS. 1C-D are simplified views of an ophthalmic device in position on an eye, according to some embodiments of the invention;

FIG. 2 is a method of use of an ophthalmic device, according to some embodiments of the invention;

FIG. 3 is a method of use of an ophthalmic device, according to some embodiments of the invention;

FIG. 4 is a simplified schematic cross section of ophthalmic devices, on an eye surface, according to some embodiments of the invention;

FIG. 5A is a simplified schematic top view of an ophthalmic device, according to some embodiments of the invention;

FIG. 5B is a simplified schematic side view of an ophthalmic device, according to some embodiments of the invention;

FIG. 5C is a simplified schematic sectional view of an ophthalmic device, according to some embodiments of the invention;

FIG. 5D is a simplified schematic of an ophthalmic device, according to some embodiments of the invention;

FIG. 6 is a simplified schematic cross section of an edge portion of an ophthalmic device, according to some embodiments of the invention;

FIG. 7 is a simplified schematic cross section of an edge portion of an ophthalmic device, according to some embodiments of the invention;

FIGS. 8, 9, 10, 11, 12, 13, 14, 15 16 and 17 are simplified schematic top views of ophthalmic devices, according to some embodiments of the invention;

FIG. 18A is a simplified schematic top view of an ophthalmic device, according to some embodiments of the invention;

FIG. 18B is a simplified schematic of an ophthalmic device, according to some embodiments of the invention;

FIG. 18C is a simplified schematic cross sectional view of an ophthalmic device, according to some embodiments of the invention;

FIG. 19 is a simplified schematic cross sectional view of an ophthalmic device, according to some embodiments of the invention;

FIGS. 20, 21, 22, 23, 24, 25, 26, 27 and 28 are simplified schematic base views of ophthalmic devices, according to some embodiments of the invention;

FIG. 29A is a simplified schematic cross sectional view of a portion of an eye surface, according to some embodiments of the invention;

FIG. 29B is a simplified schematic cross section view of an ophthalmic device on an eye surface, according to some embodiments of the invention;

FIG. 29C is a simplified schematic cross section view of an ophthalmic device on an eye surface, according to some embodiments of the invention;

FIGS. 30A-C are simplified schematic cross sectional views of a portion of a device on an eye surface, according to some embodiments of the invention;

FIG. 31A is a simplified schematic cross section view of an ophthalmic device on an eye surface, according to some embodiments of the invention;

FIG. 31B is a simplified schematic view of an ophthalmic device, according to some embodiments of the invention;

FIG. 31C is a simplified schematic to view of an ophthalmic device, according to some embodiments of the invention;

FIGS. 32, 33, 34, 35, 36 and 37 are simplified schematic cross section views of portions of ophthalmic devices, according to some embodiments of the invention;

FIGS. 38, 39, 40, 41, 42, 43 and 44 are simplified schematic cross sectional views of devices, according to some embodiments of the invention;

FIGS. 45, 46, 47, 48, 49 and 50 are simplified schematic cross sectional views of double layer devices according to some embodiments of the invention;

FIGS. 51, 52, 53, 54, 55, 56, 57 and 58 are simplified schematic cross sectional views of multi-layer devices, according to some embodiments of the invention;

FIGS. 59, 60 and 61 are simplified schematic cross sectional views of multi-layer devices, according to some embodiments of the invention;

FIGS. 62A-F are simplified schematic cross sections of a portion of a device as residence time of the device progresses, according to some embodiments of the invention;

FIG. 63 is a flowchart of a disintegration progression of a device, according to some embodiments of the invention;

FIGS. 64A-C are simplified schematic cross sections of a device as residence time of the device progresses, according to some embodiments of the invention;

FIGS. 65A-D are simplified schematic cross sections of a device as residence time of the device progresses, according to some embodiments of the invention;

FIG. 66 is a simplified schematic cross section of a device, according to some embodiments of the invention;

FIG. 67 is a simplified schematic cross section of a device, according to some embodiments of the invention;

FIGS. 68A-B are simplified schematic cross sectional views of a device on an eye surface, according to some embodiments of the invention;

FIG. 69 is a method of ophthalmic device manufacture, according to some embodiments of the invention;

FIG. 70 is a method of film manufacture, according to some embodiments of the invention;

FIGS. 71A-D are simplified schematic cross sectional views of a portion of a device, according to some embodiments of the invention;

FIG. 72 is a method of manufacture, according to some embodiments of the invention;

FIGS. 73A-D are simplified schematic cross sectional views of films, according to some embodiments of the invention;

FIGS. 73E-F are simplified schematic cross sectional views of devices, according to some embodiments of the invention; and FIGS. 74A-C are simplified schematic cross sectional views of a device, according to some embodiments of the invention.

DESCRIPTION OF SPECIFIC EMBODIMENTS OF THE INVENTION

The present invention, in some embodiments thereof, relates to an ophthalmic device and, more particularly, but not exclusively, to a drug eluting ophthalmic device.

Overview

A broad aspect of some embodiments relates to an ophthalmic device for treatment and/or protection of the eye which, when applied to an eye surface (e.g. sclera) remains on the eye. For example, without moving from a region of the eye surface to which it has been applied and/or without being ejected from the eye during a treatment time period. Whilst, in some embodiments, the device remains comfortable for a user to wear.

In some embodiments, the ophthalmic device remains in position, for example, moving by at most 0.5-5 mm, or 0.5-1 mm, or lower or higher or intermediate ranges or distances on the eye surface from a position of application and/or a position of residence after initial migration, e.g. during a residence time.

In some embodiments, the device is in residence on the eye and/or remains in position during regular activities of a subject, for example, one or more of, blinking, tearing, crying, sweating, washing (e.g. showering), walking, exercising, sleeping. In some embodiments, the device is in residence on the eye and/or remains in position while the eyes are mainly closed e.g. during sleeping and/or for a semi-conscious or unconscious patient.

An aspect of some embodiments of the invention relates to an ophthalmic device provided in a dry form, where the device containing one or more therapeutic agent. In some embodiments, the device is provided in a semi-hydrated (e.g. including partially hydrated and or humidified) form.

A potential benefit of lack of and/or low hydration of the device being low degradation of therapeutic agent/s during storage of the ophthalmic device e.g. after manufacture and before use, for example, in some embodiments, extending shelf life. In some embodiments, the device is soft in dry form, softness, in some embodiments, enabling application of the device to the eye without prior hydration and/or softening.

In some embodiments, as the device hydrates it increases in size and/or changes shape.

In some embodiments, the ophthalmic device includes one or more therapeutic agent and/or other compound/s which are released while the device resides on the eyeball. In some embodiments, the therapeutic agent/s elute from the device when it is on the eye surface. In some embodiments, upon application, the device attaches to the eyeball onto a top the eye mucosal surface, providing protection and/or localized drug delivery to the eye. In some embodiments, the ophthalmic device includes one or more therapeutic agents in a modified release form.

In some embodiments, the ophthalmic device is positioned on the sclera, superior or inferior to the cornea. In some embodiments, the ophthalmic device is placed on a bulbar conjunctiva portion of the sclera which is the eye surface located between the cornea and the conjunctival fornix. In some embodiments, the device is positioned outside the cul-de-sac of the eye or at most partially within the cul-de-sac of the eye. In some embodiments, the device is positioned sufficiently near to the cornea that it experiences movement of an eyelid during blinking/or eyeball movement. In some embodiments, the device is visible when the eyes are in a relaxed open positon. In some embodiments, the device adheres sufficiently to the surface of the eye to be positioned in a region of the eye not and/or not fully within the cul-de-sac of the eye.

In some embodiments, the device is positioned at a region of a tear meniscus of the eye and/or a region where the meniscus is located for a larger portion of the time e.g. at least 50% of the time. Where, position of the meniscus layer is in some embodiments, defined by a position of a lower eyelid. In some embodiments, the device is positioned such that, when the eye is wide open, the device is not covered by the eyelid, for example, even partially.

In some embodiments, the device is positioned outside area/s described in the above two paragraph and migrates to the area/s, for example, in less than 1 minute to one hour. Where, in some embodiments, the device then remains in situ moving, for example, by at most 0.5-5 mm, or 0.5-1 mm during a residence time of the device.

A potential advantage of device positioning is contact with high fluid levels (e.g. tear fluid) and/or high fluid transfer. For example, associated with short therapeutic material delivery time and/or optionally disintegration time and/or optionally residence time of the device.

A potential advantage of positioning the device on the bulbar conjunctiva associated with the tighter surface of the bulbar conjunctiva e.g. as compared to wrinkled and/or sliding fornix conjunctiva. Potentially, the smooth and/or tight surface of the bulbar conjunctiva requires less force to keep the device tightly in position on the sclera e.g. as compared to, for example, the fornix conjunctiva and/or conjunctiva within a cul de sac of the eye. Potentially, this allows use of flatter devices (e.g. a radii of curvature ratio of a device posterior surface to conjunctiva is, in some embodiments, less than 0.8). A potential advantage of positioning the device on the bulbar conjunctiva e.g. as opposed to the cul de sac of the eye is ease of application of the device. For example, without one or more of tilting of the eye and/or withdrawal of the eyelid and/or without use of an applicator.

In some embodiments, the device (e.g. curvature of one or more portion of the device e.g. to generate sufficient suction to hold the device in position) conforms to an eye surface which is sufficiently tight and/or smooth e.g. the bulbar conjunctiva but not the fornix conjunctiva.

A potential advantage of described device positioning is limited or lack of interference of the device with patient vision.

Generally, there is a change in the radii of curvature between the sclera at the bulbar conjunctiva region and the cornea where the change in curvature occurs in the limbus region. A device adhering to the sclera (e.g. including one or more feature as described herein) where the device has thin edges potentially prevent the device from climbing from the sclera and/or limbus to the cornea. Potentially fixing the device into position and/or avoiding obstruction of sight of the patient by the device.

In some embodiments, a device with extent (e.g. a diameter of) 2-8 mm and adhering to the sclera (e.g. as described herein) and/or having a low profile about the eye surface (e.g. at the device edge) potentially has low likelihood of being ejected from the eye. Where, in some embodiments, a profile of a device over the eye surface (e.g. at device edges) is associated with one or both of thin edges of the device and/or edges being recessed into a surface of the eye. In some embodiments, a step formed between an edge of said device and the eye surface is 1-100 microns, or 10-50 microns, or lower or higher or intermediate ranges or steps. In some embodiments, a patient blinking deflects an eyelid (or both eyelids e.g. in a case of a ring and/or partial ring-shaped device covering the bulbar conjunctiva) by this step.

In some embodiments, edge characteristics (e.g. shape and/or thickness) as described in this document are for all of or a portion of an edge region of the device. For example, a portion of a circumferential edge of the device. For example, for 20-99%, or 80-90%, or lower or higher or intermediate ranges or percentages, of a circumference of the device. In some embodiments, different portions of a circumferential edge of a device have different properties e.g. shape and/or thickness.

In some embodiments, adherence to the sclera is associated with adherence of edges of the device to the sclera, for example influenced by an extent of conforming of the device to the sclera and/or of the sclera to the device. In some embodiments, a device includes one or more feature to increase adherence between the device and the sclera. For example, roughness and/or anchors (e.g. cavity/ies, protrusion/s and/or hook/s) for example, located at a posterior surface and/or at edges of the device.

For example, associated with the edge of eyelid failing to grasp and/or to push the ophthalmic device and/or to move it to the eye corners (commissures) and/or to manipulate the device for expulsion.

An aspect of some embodiments relates to an ophthalmic device which adheres to an eye surface. In some embodiments, the device includes one or more feature which increases adherence of the device to the eye surface. Additionally or alternatively, in some embodiments, the device includes one or more feature which reduces dislodgement forces experienced by the device. Forces, for example, associated with the subject blinking and/or tearing and/or rubbing of the eyes.

A potential advantage of adherence of the ophthalmic device is reduction and/or elimination of mobility of device. For example, enabling selection of a fixed position for residence of the device and/or enabling treatment of a selected portion of the eye by the device.

A potential advantage of adherence of the ophthalmic device is increased residence time of the device on the eye surface. Without wanting to be bounded by theory it is hypothesized that increased adherence of the device to the eye surface reduces fluid flow between the device and the eye. Potentially, reduced fluid flow extends the residence time of the device.

In some embodiments, a body of an ophthalmic device has a concave posterior surface. In some embodiments, the body has a convex anterior surface.

In some embodiments, concavity of a posterior surface in contact with the eye surface (e.g. sclera), increases adhesion of the device to the eye surface. The concavity, for example, providing suction force between the device and eye surface, adhering the device to the eye surface.

Optionally, in some embodiments, a radius of curvature of one or more portion of the posterior surface of the device is smaller than that of the portion of the eye to which the device is to be adhered to. For example, the sclera.

In some embodiments the posterior surface is smooth for example, potentially reducing irritation associated with contact between the eye surface and the device. In some embodiments, the posterior surface includes rough portion/s and or anchor/s potentially increasing adhesion by friction between the posterior surface and the eye surface. In some embodiments, edge regions (e.g. and optionally, in some embodiments, not a central region which is smooth) of the posterior surface are rough and/or include anchor/s and/or protrusions and/or cavities.

In some embodiments, the device remains in position despite having a posterior surface with low radius of curvature. For example, where a ratio between the radius of curvature of the posterior surface to the radius of curvature of the of the eye is 0.6-0.95, or 0.8-0.95, or 0.8-1, or larger than about 0.8, or lower or higher or intermediate ranges or ratios. For example, where the radius of curvature of the posterior surface is the same as or larger than that of the portion of the eye to which the device is to be adhered e.g. the sclera. For example, in some embodiments, despite having a posterior surface which is flat or convex. For example, where one or more of mucoadhesive property/ies and/or anchoring feature/s enable the device to adhere to the eye surface.

In some embodiments, a device flips from having a flat or concave anterior surface and a flat or having a flat or convex posterior surface to the reverse e.g. upon positioning of the device on the eye. For example, in some embodiments, a user places a device on their finger and/or an applicator (and/or where the device is provided on an applicator) where a posterior surface is convex and an anterior surface is concave. In application a force being applied (e.g. by the user and/or applicator) to flip the device into a configuration where the posterior surface is concave and the anterior surface is convex e.g. prior to and/or during contacting of the device to the eye surface. In some embodiments the device is provided pre-formed to a desired shape (e.g. including desired curvatures) of the intended location of insertion. In some embodiments, the device has (e.g. is provided with) a curvature of the intended location of insertion (e.g. the posterior surface of the device has the curvature of the intended location of insertion). In some embodiments, the device changes shape (e.g. curvature/s) during and/or after positioning on the eye surface. For example, in some embodiments, the device changes shape during hydration and/or adhesion e.g. on the eye surface.

In some embodiments, the ophthalmic device is one or more of flexible, elastic, and supple e.g. to conform with a shape of the eyeball. In some embodiments, the ophthalmic device elasticity and/or softness is similar to the elasticity and/or softness of soft contact lenses. In some embodiments, the ophthalmic device has elasticity or softness, in one or more direction, with a Young's modulus of 0.3-1.5 MPa or 0.3-1.5 MPa, or lower or higher or intermediate elasticities/ softness or ranges. In some embodiments, the ophthalmic device has elasticity, in one or more direction, with a Young's modulus of 0.1-200 MPa. In some embodiments, the ophthalmic device has elasticity, in one or more direction, (e.g. Young's modulus 0.1-200 MPa, or 0.4-1.4 MPa or 0.3-1.5 MPa, or lower or higher or intermediate elasticities or ranges) in a dry form. In some embodiments, the ophthalmic device has elasticity, in one or more direction, (e.g. Young's modulus 0.1-200 MPa, or 0.3-1.5 MPa, or 0.4-1.4 MPa, or lower or higher or intermediate elasticities or ranges) in a wet form while in the eye. In some embodiments, the ophthalmic device has elasticity allowing elongation of 10% to 500% or more (in dry form and/or in wet form).

In some embodiments, the ophthalmic device is one or more of rigid, and shaped e.g. shaped to conform with a shape of the eyeball. In some embodiments, the ophthalmic device elasticity and/or hardness, in one or more direction, similar to the elasticity and/or hardness of hard or rigid contact lenses. In some embodiments, the ophthalmic device has elasticity, in one or more direction, with a Young's modulus of 100-5000 MPa, or lower or higher or intermediate ranges or elasticities. In some embodiments, the ophthalmic device has this elasticity, in one or more direction, when in a dry form. In some embodiments, the ophthalmic device has this elasticity in the wet form e.g. while in the eye.

In some embodiments, the ophthalmic device has layers with different material properties e.g. elasticity and/or flexibility. In some embodiments, the ophthalmic device has regions having different material properties e.g. elasticity and/or flexibility.

In some embodiments, the device is flexible, potentially enabling the device to shape to a surface of the eye e.g. potentially increasing user comfort (e.g. allowing the eyelid to move smoothly above the device with little or no interference and/or discomfort) and/or reducing dislodgement forces experienced by the device. In some embodiments, a flexible device has a concave posterior surface, where suction (e.g. associated with interaction between concavity of the posterior surface and the eye surface) between the device and the eye surface then flattens the device onto the eye surface. Potential advantages of a flatter (e.g. lower profile) device include reduced likelihood of dislodgement e.g. associated with blinking and/or eyeball movement and/or increased comfort of wear for the subject.

In some embodiments, elasticity of the device increases suction force between the device and the eye surface to adhere the device to the eye. Where, for example, in some embodiments, elasticity compensates for low concavity curvature of the posterior surface of the device.

In some embodiments, flexibility and/or elasticity of the device increases sealing between the device edge and the eye surface.

In some embodiments, the posterior surface includes one or more mucoadhesive part. Where mucoadhesive material/s in some embodiments, increase adhesion of the device to the eye surface.

Optionally, in some embodiments, the posterior surface includes a mucoadhesive layer. Where, in some embodiments, the layer covers the posterior surface. Alternatively, in some embodiments, the mucoadhesive layer is a non-continuous surface, where hole/s, for example, allow water penetration and/or drug transportation e.g. to a layer underneath the mucoadhesive layer. In some embodiments, the mucoadhesive layer has a ring-shape including an aperture in the center e.g. enabling water penetration and/or drug transportation.

The mucoadhesive layer in the device, in some embodiments, is provided dry and/or semi-hydrated. Where, in some embodiments, upon application of the device to the eyeball, the mucoadhesive layer hydrates and becomes sticky, for example, in less than 10 seconds, or in less than 30 seconds, or in less than 1 minute.

In some embodiments, the material/compound/polymer in a mucoadhesive layer has an adherence force of 80-200%, or of 100-200%, or of over 100%. Where, for example, pectin is defined as having an adherence force of 100%.

In some embodiments, mucoadhesive portions include at least one mucoadhesive compound, which in some embodiments, is selected from the group consisting of gelatin, alginates, chitosan, amylose, collagen, sodium poly-acrylate, modified starch, elastin, polyacrylic acid and combinations thereof.

In some embodiments, the posterior surface includes one or more cavity or protrusion, for example, on the posterior surface of the device.

Without wanting to be limited by theory, it is hypothesized that, in some embodiments, a cavity increases suction between the device and the eye surface e.g. localized suction at the cavity. In some embodiments, eye tissue enters the cavity (e.g. under suction forces of the cavity), potentially increasing adherence between the device and the eye. A potential advantage of cavity/ies on the posterior surface is extended residence time of the device on the eye.

In some embodiments, the device has a plurality of cavities, where in some embodiments, two or more of the cavities are about the same size and/or shape. Where, in some embodiments, two or more of the cavities are different from each other, for example, in size and/or shape.

In some embodiments, an opening size of a cavity, is between 0.005 mm and 20 mm, or 0.005-2 mm, or 0.005-1 mm, or 0.005-0.5 mm, or 1-2 mm, or lower or higher or intermediate ranges or dimensions. In some embodiments, a cavity has a large opening, for example, extending over at least half of an area of the surface (e.g. posterior surface) and/or having an extent of 1-10 mm, or 1-8 mm, or 1-5 mm. In some embodiments, an aperture of a cavity is macroscopic or microscopic in size. In some embodiments, a depth of a cavity is 5 microns-1 mm, or 5-400 microns, or 5-200 microns, or lower or higher or intermediate depths or ranges. In some embodiments, a cavity extends through most of a thickness of the device, for example, through at least 50-90%, or 80-99%, or 90-99%, or lower or higher or intermediate ranges or percentages of a thickness of the device in a region of the cavity.

In some embodiments, protrusion/s have a rounded and/or blunt shape.

In some embodiments, the device has a plurality of protrusions, where in some embodiments, two or more of the protrusions are about the same size and/or shape. Where, in some embodiments, two or more of the protrusions are different from each other, for example, in size and/or shape.

In some embodiments, a size of a protrusion, above a surface of the device is 5-400 microns, or 20-200 microns, or lower or higher or intermediate ranges or sizes. In some embodiments, an extent of a footprint of a protrusion on the surface of the device is 5 microns to 3 mm, or 5 microns to 1 mm, or 5-700 microns, or 5-400 microns or lower or higher or intermediate extents or ranges.

A potential benefit of protrusion/s is increased adherence of the ophthalmic device to the eye surface. In some embodiments, protrusion/s increase friction between the eye surface and the eye surface. In some embodiments, protrusion/s increase (e.g. between the protrusions) increase the suction force between the device and the eye surface.

In some embodiments, the device presents a low friction surface to the eyelid (e.g. is smooth). A potential advantage of which is reduced likelihood of dislodgement of the device.

Optionally, in some embodiments, one or more of portion of an anterior surface of the device is smooth and/or includes lubricious material. Where the anterior surface of the device is a surface which is in contact with the inner surface of the eyelid, at least part of the time. Potentially, in some embodiments, smooth and/or lubricous material reduces friction between the eyelid and the surface. Potentially, in some embodiments, the smooth and/or lubricous material minimizes irritation of the eye, e.g. the eyelid, e.g. associated with the ophthalmic device.

In some embodiments, a lubricious material layer covers the anterior surface where, in some embodiments, the layer is continuous. In some embodiments, the lubricious layer is a non-continuous surface, (e.g. including one or more hole) for example to allowing water penetration and/or drug transportation. For example, in some embodiments, a lubricious material layer includes holes. In some embodiments, the anterior surface hosts one or more lubricious material portion where, in some embodiments, one or more of the portions is connected to other portion/s and/or one or more of the portions is not connected to other portions. Optionally, in some embodiments, the lubricous surface is temporary, where, in some embodiments, one or more portion of lubricous material degrades and/or disappears (e.g. is absorbed and/or expelled by the eye), for example, before other portion/s of the device degrade.

In some embodiments, a material layer has variable thickness and/or variable material properties e.g. a lubricious layer and/or a mucoadhesive layer. Where, for example, upon attachment to the eye, a material has a larger extent on the anterior surface than after a time period of residence on the eye, where, in some embodiments, more rapidly degraded portion/s (e.g. thinner portions and/or portions having more a rapidly degraded composition) of the layer dissolve prior to other portion/s e.g. to reveal lower layers which in some embodiments comprise therapeutic agent/s.

In some embodiments, the device has an edge designed for user comfort and/or to increase adherence to the eyeball. In some embodiments, the ophthalmic device has a thin edge. In some embodiments, an edge (e.g. circumferential edge) of the device has average thickness of about 15 microns, or about 20 microns, or about 30 microns or about 50 microns. In some embodiments, the ophthalmic device has a thin edge of about 15 microns, or about 20 microns. In some embodiments, the ophthalmic device has an edge thickness of about 5-200 microns, or 5-200 microns, or lower or higher or intermediate thicknesses or ranges. In some embodiments, the edge of the device is blunt and/or curved and/or rounded for example, increasing comfort of wear for a user. In some embodiments, the edge of the device is sharp e.g. chisel shaped and/or knife edged. In some embodiments, the edge of the ophthalmic device is defined as a 0.1-1 mm edge region, or 0.5-1 mm of the device. In some embodiments, an edge thickness is measured at 0.5 mm, or 1 mm from a circumference of the device.

In some embodiments, a thin edged device presents less surface area to interact with the eyelid as is moves over the area of the ophthalmic device, the thin edge potentially reducing likelihood of dislodgement of the device e.g. during blinking and/or eyeball movement.

In some embodiments, a thin edged device provides improved sealing between edges of the device and the eye surface. A potential advantage of sealing between the device edges and the eye surface is increased suction between the device and the eye surface. A potential advantage of sealing between the device edges and the eye surface is reduced accumulation of debris (e.g. one or more protein, mucus, oil, and skin cells) of between the device and the eye surface potentially minimizing risk of infection associated with use of the ophthalmic device.

In some embodiments, a thin edged device conforms to a shape of the eye surface at the device edges.

In some embodiments, an edges of the device provide anchoring of the device into the eye surface e.g. soft tissue of the conjunctiva e.g. the soft and thick scleral conjunctiva which is apparently, about 25-40 microns thick and is apparently even thicker in the fornix. In some embodiments, the device recesses into the eye surface at edges of the device and/or makes an indentation in the eye surface, for example, the recessing associated with one or more of pressure between edges of the device and/or softness of the eye surface.

In some embodiments, edges (and/or edge region/s) of a device conform to a shape of the eye surface. For example, in some embodiments, edge region/s are flexible and/or elastic and/or sufficiently thin to conform to the eye surface. Potentially, edges conforming to the eye surface reduces risk of dislodgement of the device. In some embodiments, the ophthalmic device is thin and/or has a low profile, for example, where a maximum thickness of the device and/or a thickness of the device is 40-200 microns, or 120-300 microns, or 200-1000 microns, or 300-500 microns, or about 400 microns, or at most 400 microns or at most 300 microns, or about 200 microns, or at most 200 microns, or at most 150 microns, or at most 100 microns, or at most 80 microns or at most 60 microns, or lower or higher or intermediate ranges or thicknesses. Potential advantages of a thin device include one or more of; increased flexibility of the device, and low irritation of the eye, low likelihood of movement and/or expulsion from the eye.

In some embodiments, the ophthalmic device has a thickness of less than 100 microns, or not greater than 200 microns, or not greater than 60 microns, or not greater than 40 microns, or between 80 and 100 microns, or between 60 and 80 microns, or between 40 and 60 microns, or between 20 and 40 microns, or between 10 and 20 microns, or between 5 and 10 microns, or not greater than 10 microns, or not greater than 5 microns.

In some embodiments, pressure between the eye and the device is increased by increasing a thickness of the device and/or a thickness of an edge region of the device. Where, increased pressure (and/or sealing between the eye and the device e.g. associated with pressure and/or contouring of the eye to the device or the device to the eye) in some embodiments, reduces tear fluid penetrations between the device and the eye surface.

In some embodiments, the device is small. In some embodiments, a maximum and/or average extent of a device is about 1-8 mm, or 4-6 mm, or lower or higher or intermediate ranges or sizes. In some embodiments, the ophthalmic device has a size (e.g. maximum and/or average extent) of about 4 mm. In other embodiments, the device has dimensions of between about 0.5 to about 20 mm in maximum size. A potential advantage a small dimensioned device is lower likelihood of dislodgement of the device during movement of an eyelid over the device.

In some embodiments, an ophthalmic device is elongated. Where, for example, in some embodiments, a dimension of the device measured along an axis of the elongation is about 0.5 mm, or about 1 mm, or about 2 mm, or about 3 mm, or about 4 mm, or about 5 mm, or about 6 mm, or about 7 mm, or about 8 mm, or about 9 mm, or about 10 mm, or about 11 mm, or about 12 mm, or about 13 mm, or about 14 mm, or about 15 mm, or about 16 mm, or about 17 mm, or about 18 mm, or about 19 mm, or about 20 mm.

Where, in some embodiments, an extent of the device is measured as a maximum dimension of a smallest cuboid shape into which the device fits. In some embodiments, for example, associated with low curvatures of the device surfaces, the cuboid bounding shape is thinner in one dimension, (e.g. associated with a direction into the eye when the device is on the eye) than in the other two dimensions.

An aspect of some embodiments of the invention relates to an ophthalmic device which degrades and/or disintegrates within the eye.

In some embodiments, the ophthalmic device is a biocompatible device which is designed to be partially or completely biodegradable and/or bioerodible.

For example, in some embodiments, a portion of a device degrades e.g. once the device is adhered to the eye surface. For example one or more mucoadhesive portion and/or one or more lubricous portion. For example, in some embodiments, one or more portion of the device is selected to degrade within the eye, in about 1 minute to 30 minutes or 15 minutes to 1 hour or about 0.5 hour to 8 hours or 4 to 24 hours, or 12 hours to 3 days, or 1 day to 7 days or 3 days to 2 weeks or 1 week to 1 month. In some embodiments, one or more portion degrades to enable eluting of therapeutic material. For example, in some embodiments, as a portion comprising therapeutic material degrades, it elutes the therapeutic material into eye tissue and/or eye fluid. For example, in some embodiments, a portion degrades to reveal a portion comprising therapeutic material. Where, in some embodiments, the degrading portion initially covers at least a portion of the portion comprising therapeutic material.

In some embodiments, the device includes biodegradable and/or bioerodible material and/or the device body is biodegradable and/or bioerodible. For example, in some embodiments, the material and/or device is degraded and/or its properties are deteriorated when exposed to a biological environment, for example, a biological system e.g. the eye, and/or to a similar in vitro environment simulating conditions of a biological system. In some embodiments, degradation and/or deterioration of the device is manifested by change (e.g. reduction) in one or more of device's physical properties, for example one or more of; device integrity, tensile strength and elasticity of the device body (e.g. of film of the device body).

An aspect of some embodiments of the invention relates to a multi-layer ophthalmic device. In some embodiments, the device includes one or more of a lubricous layer, a mucoadhesive layer and an additional layer. In some embodiments, one or more layer includes therapeutic material. In some embodiments, the additional layer is disposed between the mucoadhesive and lubricous layers forming an intermediate layer. In some embodiments, a device includes more than 2, or more than 3 layers, for example, 1-10 layers, or lower or higher or intermediate numbers or ranges. In some embodiments, one or more layer extends over a surface of the device. In some embodiments, one or more layer does not cover a surface of the device for example, covering a portion of an area of a device surface, for example, having holes. In some embodiments, an intermediate layer covers a portion (e.g. half) of the device where, in some embodiments, the portion of the device including the intermediate layer is positioned inferiorally on the eye surface.

In some embodiments of the invention, the device is made from a film comprising at least two layers. In some embodiments, films are made of biodegradable material and/or a combination of materials forming the raw material for the device of the invention, for example, where films, in some embodiments, are manufactured into devices by one or more processing steps.

In some embodiments, therapeutic agent/s are released from the device (e.g. from an internal surface and/or portion of the device) through pores, or holes and/or apertures and/or channels. In some embodiments, therapeutic agent/s are released from the device through one or more of a posterior surface (or portion thereof), an anterior surface (or portion thereof), a perimeter and/or edge of the device (or portion thereof). For example, through one or more of pores, holes, apertures, and channels. Where, in some embodiments, pores and/or holes and/or apertures and/or channels are millimetric, or submilimetric or nanomilimetric in size.

A potential advantage of the ophthalmic device is convenience of use where, in some embodiments, the device is applied by the user once to cover a time period longer than of topically applied preparations, for example, a time period of longer than 10 minutes or longer than an hour or longer than a day. Where, in some embodiments, the device serves as controlled release vehicle for one or more therapeutic ingredient.

A potential benefit of an ophthalmic device configured to reside on an eye surface is potentially increased residence time of a treatment drug in the eye. For example, as compared to periodically applied topical (e.g. eye drops, ointment).

A potential benefit of an ophthalmic device which elutes medication while residing on an eye surface is the ability to provide and/or maintain adequate concentration of drugs in the pre-corneal/pre-scleral tear film e.g. for extended periods of time.

A potential benefit of an ophthalmic device which elutes medication while residing on an eye surface e.g. maintaining a position on the eye surface is the potential ability for medication to diffuse through eye tissue. For example, penetrating into the sclera and/or into the cornea and/or into the eyeball, and/or reaching more internal portion/s of the eye. Potentially enabling, in some embodiments, topical medication of those areas which are usually treated by injection e.g. into the eyeball.

A potential benefit of an ophthalmic device (e.g. with extended residence and/or elution times is) is the ability to provide and/or maintaining adequate concentration of drugs to intranasal region/s (e.g. as delivered by tear fluid) and/or to the brain and/or to the head and/or to another target organ and/or as systemic drug delivery.

In some embodiments, the ophthalmic device being in residence for a period of time enables steady elution of treatment materials into the eye potentially reducing effects of periodic dosing such as, for example, a transient period of systemic and/or local overdose (potentially associated with high risk of side effects) e.g. followed by an extended period of sub-therapeutic levels before the administration of next dose. Where the rate of tissue drug uptake is high at early times after dosing, but declines rapidly. A long residence time, for example, as compared to, eye drops applied to the eye e.g. the surface of the eyeball, where blinking and natural tear flow combine to limit time that liquid medicament will remain effective e.g. to a few minutes. Potentially, less therapeutic ingredient per treatment is used in treatment of a subject using an ophthalmic device e.g. as opposed to topical preparations where therapeutic ingredients may be washed out before they are effective requiring higher quantities of therapeutic ingredient and/or where high patient compliance is more likely to be lower as application is frequent potentially resulting in more discarded un-used therapeutic ingredients.

In some embodiments, the ophthalmic device includes large amounts of therapeutic ingredient/s (e.g. about 1 mg to about 20 mg or more than 1 mg, or more than 20 mg, or lower or higher or intermediate doses or ranges) and/or is able to elute such ingredient/s to a surface of the eye. A potential advantage of the ophthalmic device is the ability to dispense therapeutic ingredient, (e.g. a larger amount than that of topically applied preparation/s), to the surface of the eye and/or into the eyeball (potentially replacing eyeball injections). Where for example, a topically applied preparation having up to 1% concentration of therapeutic ingredients applied as eye drops, for example, 30 microliter is, 0.3 mg where a significant portion of the therapeutic ingredient is expected to be flushed naturally out of the eye within a few minutes.

A potential benefit of an ophthalmic device which elutes large amount of medication while residing on an eye surface is the ability to provide and/or maintain adequate concentration of drugs in intranasal regions and/or to the brain and/or to the head and/or to another target organ and/or the ability to provide systemic drug delivery (for example for dosing e.g. "micro dosing" of cannabinoids and/or opioids). In some embodiments the device is used for recreational drug use.

An aspect of some embodiments of the invention relates to a kit comprising an ophthalmic device (e.g. as described in this document) and instructions for use thereof. In some embodiments, the kit of the comprises means for delivering the device into the eye of a patient. For example, an applicator. In some embodiments, the ophthalmic device is packaged together with the applicator.

Optionally, in some embodiments, the kit includes a degradation formulation which, when contacted with the device when the device is on an eye surface of a patient, structurally degrades the device and/or accelerates degradation of the device.

In some embodiments, devices are provided in multi-device packs. Where, in some embodiments, two or more devices are interconnected to one another, or separated.

In some embodiments, the ophthalmic device protects a portion of the eye. For example, from external impact/s and/or chemical changes. For example, to ameliorate and/or reduce ocular damage upon orbisculation (citrus fruit squirting juice into the eye). In some embodiments, the ophthalmic device protects a portion of the eye, enabling the portion to heal. For example, in some embodiments, an incision and/or wound in the eye is closed and/or covered by placing the ophthalmic device over the incision. Where, suction forces in between the eye surface and the device, potentially assisting in closing and/or maintaining closure of the incision and/or wound potentially hastening healing.

In some embodiments, a device is designed to provide one or more therapeutic treatment requirement. Where, for example, in some embodiments, for one or more intended location on the eye surface, biodegradability feature/s, residence time, drug release time are selected to meet the therapeutic treatment requirement/s.

In some embodiments, a device is tailored to an individual subject, where, for example, in some embodiments, one or more of size, shape, curvature of surface/s, type of therapeutics, release time, residence time are selected for the individual and/or according to an individual treatment plan.

Although throughout this document, ophthalmic use of the device is described, it should be understood that one or more embodiments and/or combinations of embodiments of the device as described within this document, in some embodiments, are used in treatment of other portions of a human or animal body. For example, for portions of the eye of the than the sclera, e.g. the cornea, the cul de sac of the eye. For example, other mucosal surface/s e.g. the inner mouth e.g. the intranasal surface. For example, other tissue types and/or organs.

Although throughout this document, ophthalmic use of the device is described, it should be understood that one or more embodiments and/or combinations of embodiments of the device as described within this document, in some embodiments, are used for other applications such as: to host e.g. contain, have attached to and/or provide a support for one or more type of electronics e.g. on the eye. For example, one or more active electronic element and/or passive modules and/or components e.g. an antenna, RFID. For example, one or more capacitor and/or resistor and/or, shape memory element, or may act as a support for other element or elements in the ocular region etc.) Where, for example, in some embodiments, electronics include on or more of sensor/s (e.g. temperature sensitive element, pressure sensitive element, humidity sensitive element), imager/s (e.g. camera), a user interface, a processor, transmitter, receiver, illumination element, led screen, power source. In some embodiments, electronics (e.g. using sensor/s) are used for therapeutics (e.g. Electroconvulsive therapy (ECT) treatment) and/or diagnostics. In some embodiments, one or more electronic part is used for entertainment (e.g. VR) and/or aesthetic enhancement. In some embodiments, the device is used for entertainment and/or for aesthetic enhancement.

In some embodiments, more than one device as described in this document is used to treat a subject, for example, where multiple devices are in situ on an eye surface at the same time, for example, each device providing a particular dose, where to provide a higher dose more than one device is applied. Where, in some embodiments, multiple devices as described in this document are provided packaged together and/or where the multiple devices are provided connected.

In some embodiments, the device includes and/or is constructed from non-toxic and/or biocompatible materials. In some embodiments, where therapeutic material is toxic in high concentrations, the entire device, in some embodiments, contains less than a toxic dose and/or the device elutes the therapeutic material at sub-toxic levels.

In some embodiments one or more portion of the device include dye and/or pigment e.g. for ease of identification while in the eye, and/or during insertion and/or extraction, and/or during production. In some embodiments, dye and/or color is printed into one or more identifying shape and/or letter and/or numeral and/or barcode. In some embodiments, one or more identifier is embossed or stamped on the device. In some embodiments, the device includes one or more electronic identifier e.g. RFID on or within a body of the device. In some embodiments, device dye and/or pigment includes one or more of blue, red, fluorescent yellow, and/or any other color.

An aspect of some embodiments of the invention relates to manufacturing an ophthalmic device. Where, in some embodiments the device is manufactured from a film, for example, a multi-layer film. Where, in some embodiments, the film is cut into shape to form individual devices. In some embodiments, the film and/or individual devices are shaped for example, to form desired curvatures of surfaces. Where, in some embodiments, shaping is by casting of a solution onto a shaped support surface. Where, in some embodiments, shaping is by application of mechanical and/or chemical treatment e.g. pressure and/or heat. In some embodiments, therapeutic ingredients are incorporated into one or more solution each of which is successively cast onto a support surface to provide a multi-layer film. In some embodiments, separately cast layers have one or more different properties (e.g. thickness, mucoadhesive, lubricious, containing therapeutic agent/s). In some embodiments, one or more surface is treated to provide it with different properties e.g. a surface is treated to become more adhesive and/or more lubricious.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Ophthalmic Device

FIG. 1A is a simplified schematic cross sectional view of an ophthalmic device 100 in position on an eye surface 104, according to some embodiments of the invention.

Where, in some embodiments, eye surface 104 is a portion of a surface of conjunctiva around an eyeball 108.

In some embodiments, ophthalmic device 100 resides on a bulbar conjunctiva 104 portion of a sclera, a region of conjunctiva proximal to the cornea and in between the fornix conjunctiva 140 and cornea 102.

In some embodiments, at least a portion of device 100 is on a limbus 142.

In some embodiments, at least a portion of device 100 is located adjacent to the meniscus 105 (the valley between the eyelid edge and the eyeball where the lacrimal/tear fluid accumulates and creates a reservoir of fluid).

In some embodiments, at least a portion of device 100 or all of the device 100 resides on a different portion of the conjunctiva e.g. as described in and/or regarding step 302 FIG. 3 and/or including one or more feature as described in the "overview" section of this document.

In some embodiments FIG. 1A illustrates device 100 with respect to a lower eyelid 106. In some embodiments, FIG. 1A illustrates device 100 with respect to an upper eyelid 106.

In some embodiments, device 100 has a body including a posterior surface 116, and an anterior surface 118. In some embodiments, posterior surface 116 is concave and/or anterior surface 118 is convex. In some embodiments posterior surface 116 and/or anterior surface 118 include one or more feature as described and/or illustrated regarding one or more of surfaces 416, 417, 418, 419 FIG. 4 and/or regarding one or more of posterior and/or anterior surfaces as illustrated and/or described in one or more of FIGS. 5C, 18B, 18C, 29B, 29C, 31A, 38, 39, 41, 42, 43, 44, 47, 48, 49 and 50-58 and/or other exemplary devices as described elsewhere within this document.

FIG. 1B is a simplified schematic top view of an ophthalmic device 100 in position on an eye surface 104, according to some embodiments of the invention.

In some embodiments, device 100 is symmetrical in shape. In some embodiments, device 100 has a circular footprint e.g. when residing on eye surface 104. In some embodiments, an extent 103 of device 100 is a diameter 103 of device 100. In some embodiments, device 100 has an alternative shape and/or footprint, for example, including one or more feature as described and/or illustrated regarding one or more of devices 800, 900, 1000, 1100, 1200, 1300, 1400, 1500, 1600, 1700, FIGS. 8-17.

FIGS. 1C-D are simplified views of an ophthalmic device 100 in position on an eye, according to some embodiments of the invention.

FIG. 1C, in some embodiments, illustrates that when device 100 is in position on an eye sclera surface, in some embodiments, when the eye is in a relaxed open position, the device is partially and/or entirely revealed by the eyelid. FIG. 1D, in some embodiments, shows manual retraction of a lower eyelid to reveal device 100.

Although in FIGS. 1C-D device 100 is illustrated in position on an inferior portion of the sclera, it should be understood that, in some embodiments, device 100 is positioned on and/or resides on a superior portion of the sclera.

Exemplary Method

FIG. 2 is a method of use of an ophthalmic device, according to some embodiments of the invention.

At 200, in some embodiments, the ophthalmic device is positioned within an eye. For example, place on an eye surface, for example, onto a portion of the sclera.

At 202, in some embodiments, the ophthalmic device elutes medication into the eye.

At 204, in some embodiments, the ophthalmic device exits the eye.

FIG. 3 is a method of use of an ophthalmic device, according to some embodiments of the invention.

At 300, in some embodiments, optionally, a substance is applied to an eye and/or to the ophthalmic device.

For example, in some embodiments, the device is stored in a dry or partially hydrated form and is hydrated before use (e.g. insertion into the eye). For example, by applying water and/or a hydrating solution to the device prior to positioning the device on an eye surface. In some embodiments, the device is soaked in a hydrating solution before applying to the eye e.g. for 5 seconds-20 mins. In some embodiments, the device is humidified by exposing to humid air and/or gas before applying to the eye e.g. for 1 minute-2 hours.

In some embodiments, one or more therapeutic material is applied to the device. For example, including one or more feature as illustrated in and/or described regarding FIGS. 74A-C.

In some embodiments, mucoadhesive material and/or lubricious material is applied to the device e.g. one or more portion of the device.

At 302, in some embodiments, the ophthalmic device is applied to an eye surface. The device before application, in some embodiments, is in dry form or wet form or in partially hydrated form (humid form). In some embodiments, applying includes bring the device into contact with the eye surface e.g. the sclera.

In some embodiments, the ophthalmic device is applied on the eye surface e.g. sclera, e.g. bulbar conjunctiva by contacting the device to the surface. In some embodiments, pressure is applied to the device during application, for example, enough pressure to deform one or both of the conjunctiva and the device. Where, for example, in some embodiments, pressure applied deforms the conjunctiva in contact with edges of the device and/or deforms a central region of the device e.g. changing curvature of one or more surface at a central region of the device.

In some embodiments, the ophthalmic device is applied to a position in which it remains for a time period (the time period as described in step 307). In some embodiments, the ophthalmic device is applied to an eye surface and then migrates to the position in which it remains for a time period. Where, in some embodiments, time of migration is shorter than the residence time. Where, for example, migration time is less than 1 second-1 minute, or less than 30 minutes, or lower or higher or intermediate ranges or durations.

In some embodiments, shape and/or curvature of surface's (e.g. with respect to the eyeball) of the device lead to migration of the device to a desired position. For example, when the device is applied to the eyeball outside a desired area, and/or where the device migrates to a most stable position on the eye surface. For example, curvature of the posterior surface of the device.

The device, in some embodiments, is inserted into the eye. The device in some embodiments, is positioned on the cornea, and/or partially on the cornea, and/or partially on the sclera, and/or on the sclera, and/or at least partially below the upper eyelid, and/or at least partially below the lower eyelid, and/or on the limbus, and/or on the fornix (e.g. in the cul-de-sac), and/or at the eye corner/s, and/or on the conjunctiva.

In some embodiments, the device is directly and/or manually applied to the eye surface. For example, by the patient themselves. In some embodiments, a caregiver applies the device. Optionally, in some embodiments, the device is applied using an applicator.

In some embodiments, the ophthalmic device flips from convex to concave configuration when applied to the eye surface e.g. as described elsewhere in this document.

At 304, optionally, in some embodiments, the device hydrates within the eye.

In some embodiments, the device applied in a dry (or semi-hydrated) form and, during a time period the device hydrates, for example, changing shape and/or interaction between the device and the eye surface (e.g. increasing suction between the device and the eye surface).

In some embodiment, the device stored in dry (or semi-hydrated) form and, upon insertion to the eye, the device wetted by the tear fluid, and/or adheres to the eye surface.

In some embodiments, hydration of the device as described regarding steps 300 and/or 304 enlarges and/or expands the device in one or more dimension from dry (and/or semi-hydrated) dimensions, for example, by hydration e.g. in step 304 by tear fluid in situ on an eye surface. For example by 10%-50%, or more than 50% (e.g. from 100% to more than 150% of a pre hydrated dimension), or lower or higher or intermediate ranges and percentages.

In some embodiments, one or more of the layer of a multi-layer device has different expansion upon wetting. Where, hydration, in some embodiments, changes curvature and/or a thickness profile of one or more layer and/or of the device body.

At 306, in some embodiments, the device adheres to the eyeball. For example, where adherence of the device is sufficiently robust that the device does not move significantly (e.g. moves at most by 0.01-5 mm, or 0.1-0.2 mm, or 0.2-1 mm) and/or is not expelled from the eye, for a residence time period (residence time period, for example, as described in step 307).

Where, in some embodiments, when the device is applied to the eye surface (i.e. is in situ), material properties of a mucoadhesive layer of the device upon application and/or after the mucoadhesive layer properties change in situ (e.g. hydrate) adheres the device to the eye surface.

At 307, in some embodiments, the device remains on the eyeball for a time period.

In some embodiments, the device is maintained in situ (in the eye) for a period of at least 0.5 hours. In other embodiments, the device is maintained in situ for a period of 0.1 hours to 2 hours or between 2 hours to 8 hours. In further embodiments, the device is maintained in situ for a period over 8 hrs. In further embodiments, the device is maintained in situ for a period between 8 hours and 24 hours, 1 day to 7 days, 7 days to 1 month, 1 month to 3 months, 3 months to 1 year. In some embodiments, the device is maintained in situ between about 1 to about 30 days or between 1 month and 1 year.

In some embodiments, the device remains and/or is maintained in situ (residence time) and is expelled and/or removed from the eye after less than about 24 hours from administration. Where expelling and/or removal, in some embodiments, leaves the eye clean from the device (e.g. without leaving behind debris), for example, the eye being ready for an additional administration e.g. of an additional device.

At 308, optionally, in some embodiments, one or more portion of the device degrades and/or disintegrates. For example, where degrading and/or disintegrating includes one or more feature as illustrated in and/or regarding one or more of FIGS. 62A-E, FIG. 63, FIGS. 64A-C, FIGS. 65A-D, FIG. 66.

In some embodiments the device has one or more area and/or portion that quickly (e.g. in less than 1 minute, or in less than 10 minutes, or in less than 1 hour) dissolved after insertion. These area/s, in some embodiments, ease of insertion or location of the device in the eye. For example, a handle and/or protrusion used to manipulate the eye during application and/or insertion. These area/s, in some embodiments, cover the pupil area (e.g. area/s cover the line of sight of a patient).

In some embodiments, degradation of the device occurs by one or more of mechanical degradation (such as eyeball or eyelid movement), chemical degradation (such as tear fluid) or biological degradation (such as enzymatic activity).

At 310, in some embodiments, the device performs treatment, for example, eluting medication into the eye. In some embodiments, elution is associated with degradation of an eluting portion of the device.

At 312, optionally, in some embodiments, one or more portion of the device disintegrates. For example, a portion of the device disintegrating to reveal therapeutic material and/or to reveal additional therapeutic material. In some embodiments, portion/s of the device associated with device adhesion disintegrate. For example, a mucoadhesive layer. For example, portions which contribute to mechanical adhesion e.g. portion/s of a device edge and/or portion/s to change curvature of one or more surface of the device.

At 314, optionally, in some embodiments, the device disintegrates. For example, where disintegration of the device mechanically reduces adhesion of the device to the eye and/or reduces size of the device and/or breaks the device into pieces. In some embodiments, the entire device degrades after residence on the eye surface for a time period of between about 0.1 hours to 1 year.

At 316, in some embodiments, the device expelled from the eye naturally e.g. expelling by movement of the eyelid and/or eyeball and/or blinking and/or tearing. In some embodiments, expelling is by rubbing of the eyelids e.g. by the fingers. In some embodiments, portions of the device are expelled (e.g. when step 314 has occurred). In some embodiments, the device e.g. where the device remains in one portion, is expelled naturally. For example, upon degradation of adhesive related portion/s of the device e.g. as described in step 312.

At 318, optionally, in some embodiments, portion/s of the device are removed e.g. manually. For example, by application of mechanical force e.g. pinching and/or applying suction and/or use of a removal device (e.g. suction cup, tweezers) and/or by flushing of the eye. For example, removing the device using one or more feature of the device e.g. slit, protrusion.

In some embodiments, concurrent to one or more step and/or in between steps of the method described steps 300-318, one or more additional treatment method is administered concomitantly, sequentially or simultaneously. For example, in some embodiments, topical medication is applied e.g. during residence time of the device on the eye surface.

Exemplary Ophthalmic Device Characteristics

FIG. 4 is a simplified schematic cross section of ophthalmic devices 400, 401, on an eye surface 404, according to some embodiments of the invention.

In some embodiments, the eye surface 404 is a sclera of the eye (e.g. including the conjunctiva).

Illustrated on FIG. 4 are radius of curvature RS of sclera 404, a radius of curvature RC of a cornea 402.

In some embodiments, devices 400, 401 are not illustrated to scale with respect to eye anatomy. Where, in some embodiments, device 400 has an anterior surface 418 and a posterior surface 416. Where, in some embodiments, device 401 has an anterior surface 419 and a posterior surface 417.

In some embodiments, device 400 is a device immediately after application of the device to sclera 404. In some embodiments, device 401, is the same device as device 400, a time period after application of the device to eye surface 404.

In some embodiments, device 400 illustrates a device before application, and device 401 illustrates the same device after application, where application of the device includes applying pressure to the device. For example, sufficient pressure to deform the device and/or eye tissue.

In some embodiments, after an initial deformation of one or both of tissue and the device under application pressure, the device, in some embodiments, undeforms e.g. at least partially, to arrive at a balance between elasticity of the device and/or of the eye surface. Where deformation of the device and/or tissue surface, in some embodiments is additionally affected by surface tension forces.

In some embodiments, deformation of the device after application of the device (e.g. without application of pressure or enough pressure to deform the device or tissue) is due to (e.g. only) surface tension force/s.

In some embodiments, pressure at edge/s of device 400, 401 recesses device edges into tissue of the eye 420 and/or makes an indentation in the tissue 420. Where, in some embodiments, pressure at the device edge/s is associated with one or more of; suction between device 401 and sclera 404, and force of movement of the eyelid on anterior surface 418.

In some embodiments, device 400 illustrates shape of a device (e.g. including radii of curvature of an anterior and a posterior surface of the device) before contact the eyeball. In some embodiments device 401 illustrates a shape of the device after contacting the eyeball.

In some embodiments, force (e.g. suction and/or externally applied force/s by a user and/or applicator) between device 400 and sclera 404 (and/or force applied) flattens device e.g. transferring between device 400 and device 401. Where, in some embodiments, the force acts to increase one or more of; radius of curvature of the posterior surface (e.g. radius RP<RP1), radius of curvature of the anterior surface (e.g. RA<RA1), and an extent of the device.

Anterior surface 418, in some embodiments, has higher radius of curvature RA than the posterior surface RP. For example, where, in some embodiments, RA is 1.2-5 times RP, or lower or higher or intermediate multiples or ranges.

In some embodiments, dimensions and/or ratios thereof (e.g. curvatures) as described in this document relate to average adult human eye curvatures. Where, for example, in some embodiments RS is about 12 mm and RC is about 8 mm. In some embodiments, dimensions are selected for different anatomies, for example for a child's eye, for example for an animal eye, for example for a different surface (e.g. mucosal surface).

In some embodiments, flattening of the device increases an extent of the device. Where, in some embodiments, an extent of the device is defined as a largest and/or average dimension of a smallest cuboid shape containing the device.

device 404 and/or a curvature of an eye surface adjacent the proximal surface. In some embodiments, dimension/s of the space depend on softness of the device and/or strength of suction between the device and the eye surface.

In some embodiments, before the device is placed and/or adhered to eye surface 404 e.g. as illustrated by device 400, exemplary maximal space dimensions for different device extents is illustrated by the below table. Where, these dimensions, in some embodiments, are for a posterior surface radius of curvature of about 9.6 mm and an eye surface radius of curvature of about 12 mm. For example, a device with extent (e.g. diameter) of 2-8 mm, in some embodiments, has a maximum space of 10-190 microns, for example, about 50 microns.

| Device extent | 2 mm | 3 mm | 4 mm | 5 mm | 6 mm | 7 mm | 8 mm |
|---|---|---|---|---|---|---|---|
| maximal space between posterior surface and eye surface | 10 microns | 20 microns | 40 microns | 70 microns | 100 microns | 140 microns | 190 microns |

In some embodiments, the extent of the device is a diameter of a device with a circular shaped footprint. Where footprint, in some embodiments, is defined, when the device is placed upon a surface (e.g. a flat surface e.g. an eye surface) by a shape of an edge of portions of the device contacting the surface.

In some embodiments, flattening of the device decreases a thickness, a thickness 424, 425 of the device. For example, in some embodiments, thickness 424>thickness 425.

In some embodiments, the device flattens without breaking. The device being, in some embodiments, one or more of flexible, elastic, and ductile.

In some embodiments, device elongation at break under wet conditions (e.g. hydrated and/or partially hydrated device) is between about 10% to about 400% elongation.

In some embodiments, portion/s of the eye are deformed in depth (e.g. by the device), for example at edges of the device (and/or at region/s adjacent to protrusions and/or cavities of the device e.g. as described elsewhere in this document e.g. with respect to FIGS. 30A-C) by 50 microns to 500 microns, or lower or higher or intermediate dimensions or ranges.

In some embodiments, deformation of the eye is local, for example, over at most 3 $mm^2$, or 1 $mm^2$ of a surface area of the eye.

In some embodiments, a central region of device 400, 401 deforms upon and/or during application of the device to the eye. For example, a central 50-95% volume and/or area of one or surface. In some embodiments, deformation of the central region of the device, is by change in curvature of one or more surface, for example, including one or more feature as described regarding change in curvature of surfaces from device 400 to device 401.

Where deforming of radius of curvature of a central region of the device, in some embodiments, of the posterior and/or anterior surfaces changes by 0.5-3 mm, or lower or higher or intermediate ranges or amounts.

In some embodiments, tissue local to edges of the device deforms, for example, a region of tissue at most 0.5 mm, or 1 mm or lower or higher or intermediate widths of tissue at a device edge.

In some embodiments, a maximal space 498, 499, between device 400, 401, and eye surface depends on one or more of a size and/or curvature of a proximal surface of the In some embodiments, the space between the posterior surface and eye surface is reduced e.g. in transition between device 400 and 401, for example, by 10-90%, or lower or higher or intermediate ranges or percentages.

In some embodiments, radius of curvature of a surface (and/or edge and/or corner) is defined as a radius of a circle (e.g. as illustrated by dashed circles in FIG. 4) which matches curvature of at least 60%, or 80% or 90% of the surface (and/or edge and/or corner). In some embodiments, a device has different radii of curvature for different cross sections of the device. Where, in some embodiments, although a device has different curvature for different cross sections, a relation as described herein describes one or more or all of the curvatures. For example where a posterior surface has different radii of curvature for different cross sections, each of the radii has a ratio to the radius of curvature of the sclera, of greater than 0.8. In some other embodiments, the device has a volume of between about 1 nanoliter to about 20 microliters. In some embodiments, the device has a volume of about 1, or about 2, or about 3, or about 4, or about 5, or about 6, or about 7, or about 8, or about 9, or about 10, or about 11, or about 12, or about 13, or about 14, or about 15, or about 20, or about 30, or about 40, or about 50, or about 60, or about 70, or about 80, or about 90, or about 100, or about 200, or about 300, or about 400, or about 500, or about 600, or about 700, or about 800, or about 900 nanoliter or of about 1, or about 2, or about 3, or about 4, or about 5, or about 6, or about 7, or about 8, or about 9, or about 10, or about 12, or about 14, or about 16, or about 18, or about 20 microliter.

In some embodiments, the device has a mass of between about 1 microgram to about 20 milligrams. In some embodiments, the device has a mass of about 1 nanogram, or about 2 nanograms, or about 3 nanograms, or about 4 nanograms, or about 5 nanograms, or about 6 nanograms, or about 7 nanograms, or about 8 nanograms, or about 9 nanograms, or about 10 nanograms, or about 11 nanograms, or about 12 nanograms, or about 13 nanograms, or about 14 nanograms, or about 15 nanograms, or about 20 nanograms, or about 30 nanograms, or about 40 nanograms, or about 50 nanograms, or about 60 nanograms, or about 70 nanograms, or about 80 nanograms, or about 90 nanograms, or about 100 nanograms, or about 200 nanograms, or about 300 nanograms, or about 400 nanograms, or about 500 nanograms, or about 600 nanograms, or about 700 nanograms, or about 800 nanograms, or about 900 nanograms or of about 1 milligram, or about 2 milligrams, or about 3 milligrams, or about 4 milligrams, or about 5 milligrams, or about 6 milligrams, or about 7 milligrams, or about 8 milligrams, or about 9 milligrams, or about 10 milligrams, or about 12 milligrams, or about 14 milligrams, or about 16 milligrams, or about 18 milligrams, or about 20 milligrams or about 40 milligrams, or about 100 milligrams.

Exemplary Ophthalmic Device Shape

FIG. 5A is a simplified schematic top view of an ophthalmic device 500, according to some embodiments of the invention.

FIG. 5B is a simplified schematic side view of an ophthalmic device 500, according to some embodiments of the invention.

FIG. 5C is a simplified schematic sectional view of an ophthalmic device 500, according to some embodiments of the invention.

FIG. 5D is a simplified schematic of an ophthalmic device 500, according to some embodiments of the invention.

In some embodiments, device 500 includes one or more feature as illustrated in and/or described regarding device 100 FIGS. 1A-D and/or device/s 400, 401 FIG. 4.

In some embodiments, device 500 includes an anterior surface 518 and a posterior surface 516. In some embodiments, a thickness 542 of device 500 is higher a central region of device 500 than at edge region/s of device 500. Where, in some embodiments, thickness tapers from a maximal dimension at an inner (e.g. central) point and/or region of the device. Where, thickness 542 illustrated in FIG. 5C, in some embodiments, is a maximum thickness of device 500. In some embodiments, thicknesses of device 500 are rotationally symmetrical. For example, where cross section illustrated in FIG. 5C is illustrative of all cross sections of the device. Alternatively, in some embodiments, thickness profiles vary across the device.

Referring back to FIG. 5A, in some embodiments, an extent 526 of device 500 is a diameter of a device circular footprint. In some embodiments, extent includes one or more feature as described regarding extents in other portion/s of this document. In an exemplary embodiment, extent 526 is 2-8 mm, or 3-8 mm, or lower or higher or intermediate ranges or extents.

In some embodiments, an extent 526 of device 500 is much smaller, for example, 0.1-1 mm, or 1-3 mm, or lower or higher or intermediate extents or ranges.

FIG. 6 is a simplified schematic cross section of an edge portion 644 of an ophthalmic device, according to some embodiments of the invention.

FIG. 7 is a simplified schematic cross section of an edge portion 744 of an ophthalmic device, according to some embodiments of the invention.

Where, in some embodiments, an edge region 644, 744 of a device is an edge 1-20% of a device body 600, 700 and/or an edge 0.1-1 mm of device body 600, 700.

In some embodiments, device body 600, 700, (e.g. as described elsewhere) tapers towards device edge region 644, 744. Tapering, for example, associated with curvature of the posterior 616, 716, and/or anterior surfaces 618, 718 of the device.

Referring now to FIG. 6, in some embodiments, edge region 644 forms a "chisel" shape. In some embodiments, at least a region of an edge of a device includes two edge surfaces. A first edge surface 644 and a second edge surface 646. Where, in some embodiments first edge surface 644 is inclined away, e.g. in a posterior direction away, from device anterior surface 618. In some embodiments, second edge surface 646 is inclined away from device posterior surface 616 e.g. in an anterior direction. In some embodiments first edge surface 644 and second edge surface 646 meet at a corner 645. In some embodiments, one or both of the edge surfaces 644, 646 are planar and/or have lower radius of curvature than anterior and/or posterior surfaces 618, 616. In some embodiments, corner 645 is a sharp corner e.g. with radius of curvature of less than 500 microns, or less than 1 mm, or less than 100 microns or lower or higher or intermediate radii. Where, in some embodiments, sharp corner 645, recesses and/or indents into an eye surface when the device is in situ on the eye surface.

Referring now to FIG. 7, in some embodiments, moving towards an edge 746 of the device along edge region 744, device body 700 continues to taper to edge 746 (e.g. curvature of posterior 716 and/or anterior 718 surfaces remaining about the same curvature in the edge portion/s as in other portion/s of device 700). For example, to form a "knife" edge with e.g. radius of curvature of less than 0.5 mm or less than 500 microns, or less than 1 mm, or less than 100 microns or lower or higher or intermediate radii.

In some embodiments, for example, associated with curvatures of anterior 718 and/or posterior surface 716 tapering of device 700 towards edge/s of the device is a single sided taper. For example, as illustrated in FIG. 7 where, tapering is associated with curvature of anterior surface 718. Alternatively, in some embodiments, a knife edged device has a double tapered edge. In some embodiments, tapering is alternatively or additionally associated with curvature of posterior surface.

The device, in some embodiments, has a polygonal 3-dimensional shape (e.g. footprint shape), for example, a shape of a; disc, ring, oval, elongated oval, curved oval, curved elongated oval, rod, octet, triangle, square, pentagon, hexagon.

FIGS. 8-17 are simplified schematic top views of ophthalmic devices, according to some embodiments of the invention.

In some embodiments, one or more of FIGS. 8-17 illustrated device footprints (footprint e.g. as defined above).

In some embodiments, ophthalmic devices of FIG. 8-17 include films which are thin with respect to dimension/s of the device when viewed in top view and/or footprint/s of the device e.g. as illustrated in FIG. 8-17. Where, in some embodiments, top view device extent in one or more dimension is 20-100 times, 2-50 times, 5-20 times, or 10-20 times, or 10-15 times, or lower or higher or intermediate ranges or multiples of the device maximal thickness.

Referring now to FIG. 8 and FIG. 16, in some embodiments, an ophthalmic device 800, 1600 includes one or more hole 822. For example, in some embodiments, the body of the device, which delineates hole 822, 1622, has a closed shape (at least when viewed in top view as illustrated in FIG. 8 and FIG. 16) defined by a ribbon of material, where, in some embodiments, the shape is a ring-shape (e.g. in top view) e.g. an elongated ring shape as illustrated in FIG. 8 e.g. a circular shape as illustrated in FIG. 16.

Referring now to FIG. 9 and FIG. 10, in some embodiments, an ophthalmic device 900, 1000 has an irregular shape.

In some embodiments, device shape facilitates removal e.g. by pinching (e.g. manually and/or using a removal implement). Where, for example, in some embodiments, a portion configured to fold which is optionally in a central region (in one or more dimension) of the device (e.g. fold region; 948 FIG. 9, 1048 FIG. 10) is thinner and/or has a smaller footprint extent facilitates folding after applying pinching force at one or both of larger extent regions on either side of the smaller footprint portion.

Referring now to FIG. 11, FIG. 12, and FIG. 13 in some embodiments, an ophthalmic device 1100, 1200, 1300 has an elongate shaped top view.

Where, in some embodiments, the elongate shape is rectangular 1100, 1200. Where, in some embodiments, corners of a rectangular shaped device 1100, 1200 are rounded and/or blunt, (e.g. with radius of curvature of corners of less than 1 mm) potentially preventing damage to the surface of the eye.

In some embodiments, the elongate shape 1300 is oval.

In some embodiments, elongation of device 1100, 1200, 1300 facilitates removal by pinching where pinch force, for example, is provided at outer region/s along an axis of elongation of the device.

Referring now to FIGS. 14-16, in some embodiments, a device shape e.g. device footprint is selected for anatomical fit. For example, in some embodiments, device 1400, 1500, 1600 is shaped to position the device in contact with a portion of patient anatomy. For example, in some embodiments, an elongated device is curved (e.g. including one or more feature of device 1400 FIG. 14, and/or device 1500 FIG. 15) and/or describes a curved shape (e.g. device 1600 FIG. 16) to be in contact with and/or cover a portion of the conjunctiva e.g. at least a portion of the limbus (e.g. device 1600 in some embodiments, covers the entire limbus). In some embodiments, ophthalmic device 1400, 1500 includes a curved shape top view and/or footprint. Where, for example, a central longitudinal axis 1528 of the curved shape is 1-40 mm long, or 5-20 mm, long or lower or higher or intermediate ranges or lengths.

In some embodiments, and/or devices with extent of more 5-40 mm, or 5-20 mm, or 10-20 mm, and/or devices with curved shapes are positioned under an upper eyelid. For example, as there is generally more room under the upper eyelid than under the lower eyelid.

In some embodiments, a top view shape and/or footprint of a device is rotationally symmetrical e.g. device 1600 FIG. 16, device 1700 FIG. 17.

FIG. 17, in some embodiments, a device has one or more corner e.g. three for device 1700. In some embodiments, corners of device 1700 (and/or elongation e.g. FIGS. 11-15) facilitate removal of the device by pinching, for example providing the same potential distance (e.g. associated with extent) over which to apply pinch force than a circular device, but with reduced device footprint area.

FIG. 18A is a simplified schematic top view of an ophthalmic device 1800, according to some embodiments of the invention.

FIG. 18B is a simplified schematic of an ophthalmic device 1800, according to some embodiments of the invention.

FIG. 18C is a simplified schematic cross sectional view of an ophthalmic device 1800 on an eye surface 1804, according to some embodiments of the invention.

In some embodiments, device body 1800 has a posterior surface 1816 and an anterior surface 1818; body 1800 and/or one or more of the surfaces including one or more feature as illustrated and/or described regarding device 100 FIGS. 1A-D and/or device 400 FIG. 4 (and/or one or more other device as described and/or illustrated in this document).

In some embodiments, device body 1800 includes one or more cavity 1830, 1832. Where, in some embodiments, cavity/ies 1830, 1832 are located on posterior surface 1818 of device e.g. proximal to eye surface 1804.

In some embodiments, device 1800 includes 1-50 cavities, or 1-10 cavities, or lower or higher or intermediate numbers of cavities. In some embodiments, device 1800 has four cavities 1830 e.g. as illustrated in FIGS. 18A-B.

One or more cavities, in some embodiments are connected and/or linked.

One or more cavities, in some embodiments, are separated e.g. all of the cavities are separated from each other e.g. as illustrated in FIGS. 18A-B.

Exemplary cavity shapes, include, for example, ball, dome, cylinder, pyramid, rectangular, triangular, circle, oval, elongated, rounded, annular, partially annular, radial, circumferential and any other shape.

In some embodiments, a cavity has one or more sharp edges at a cavity opening. In some embodiments, a cavity has one or more or blunt and/or rounded edge at the cavity opening.

In some embodiments, a device including a plurality of cavities has one or more cavities with different characteristic/s from one or more other cavity.

In some embodiments, one or more cavity 1830 is open through to the anterior surface, for example, providing hole/s through the device. In some embodiments one or more cavities 1830, in some embodiments, have an erodible and/or biodegradable and/or bioerodible covering.

In some embodiments, cavities 1830 are located on an outer and/or edge portion of the device. For example, a portion of the device proximal to a device outer edge e.g. forming 5-50% of a device area (e.g. top view and/or footprint and/or area of one or both of anterior surface 1818 and posterior surface 1816).

In some embodiments, cavities 1830 are symmetrically disposed on device 1800 e.g. rotationally symmetrically e.g. as illustrated in FIGS. 18A-B.

FIG. 19 is a simplified schematic cross sectional view of an ophthalmic device 1900, according to some embodiments of the invention.

In some embodiments, device 1900 includes a body having a posterior 1916 and an anterior 1918 surface. In some embodiments, device includes one or more cavity 1930. In some embodiments, a device includes both cavity/ies 1930 and protrusion/s 1934. In some embodiments, device 1900 includes one or more protrusion 1934. Where, in some embodiments, protrusion/s 1934 are located on posterior surface 1918 of device e.g. proximal to an eye surface when the device has been applied to an eye.

In some embodiments, protrusion/s 1934, include and/or are formed from biocompatible material.

In some embodiments, device 1900 includes 1-50 protrusions, or 1-10 protrusions, or lower or higher or intermediate numbers of protrusions.

One or more protrusions, in some embodiments are connected and/or linked.

One or more protrusions, in some embodiments, are separated e.g. all of the protrusions are separated from each other e.g. as illustrated in FIGS. 18A-B.

Exemplary protrusion shapes, include, for example, ball, dome, cylinder, pyramid, rectangular, triangular, circle, oval, elongated, rounded, annular, partially annular, radial, circumferential and any other shape.

In some embodiments, a protrusion has one or more sharp edges and/or corners. In some embodiments, a protrusion has one or more or blunt and/or rounded edge and/or corner.

In some embodiments, a device including a plurality of protrusions has one or more protrusions with different characteristic/s from one or more other protrusion.

The location of the protrusions, in some embodiments is anywhere on the posterior surface and/or the anterior surface. In some embodiments, a distance of protrusion 1952 of protrusion 1934 from a surface 1916 of the device is between about 0.005 mm and about 20 mm. In some embodiments, a size 1950 of protrusion 1934 (e.g. maximum and/or average) in one or more dimension perpendicular to a direction of protrusion of the protrusion from a surface 1916 of the device is between about 0.005 mm and about 20 mm.

One or more protrusions, in some embodiments, is erodible.

In some embodiments, a cavity and/or protrusion, in some embodiments, is used for the insertion and/or removal of the device. For example, in some embodiments, a finger and/or device is pressed into a cavity or protrusion to release suction and/or elevate a portion of the device (e.g. edge) and/or flip the device.

In some embodiments, a cavity and/or protrusion is used to increase adherence of the device. For example, pressure applied to the cavity or protrusion acting to increase suction between the device and the eye surface.

In some embodiments, a cavity facilitates flipping of the device, for example, upon insertion e.g. from convex to concave.

In some embodiments, one or more protrusion prove handles. For example, to facilitate application of pinch force e.g. in a removal process. For example, to facilitate application of pressure to position and/or stabilize the device e.g. upon application to the sclera.

FIGS. 20-28 are simplified schematic base views of ophthalmic devices, according to some embodiments of the invention.

In some embodiments, FIGS. 20-28 illustrate device posterior surfaces.

In some embodiments, a device has a single protrusion and/or a single cavity. For example, device 2100 FIG. 21 and/or device 2400 FIG. 24 which include, in some embodiments, a single cavity 2130, 2430, which includes in some embodiments, a single protrusion 2130, 2430.

In some embodiments, a device includes a plurality of cavities and/or protrusions. For example, FIGS. 21, 22, 23, 25-28.

For example, FIG. 20 in some embodiments, includes a plurality of protrusions only 2030 and in some embodiments, includes a plurality of cavities only 2030.

In some embodiments, cavity/ies and/or protrusion/s are disposed radially e.g. symmetrically radially on a device surface e.g. FIG. 20, FIG. 26, FIG. 28.

In some embodiments, cavity/ies and/or protrusion/s are disposed irregularly on a device surface. In some embodiments, cavity/ies and/or protrusion/s have different size and/or shape e.g. FIG. 23, FIG. 25, FIG. 27. In some embodiments, a cavity and/or protrusion is disposed in a central region of a surface, for example, cavity and/or protrusion 2734 FIG. 27, 2834 FIG. 28.

In some embodiments, one or more cavity and/or protrusion is elongate. For example, as illustrated in FIG. 22, FIG. 23, FIG. 27.

Referring to FIG. 21, in some embodiments, a protrusion and/or cavity 2130 describes a closed shape on a surface of the device. For example, a ring shape 2130.

In some embodiments, arrangement of protrusion/s and/or cavities is asymmetrical and/or irregular, for example, as illustrated by one or more of FIG. 24, FIG. 25, FIG. 27.

Referring now to FIG. 26, in some embodiments, protrusions 2634 and cavities 2630 alternate along a contour of a device. For example, in some embodiments, both protrusions 2634 and cavities 2630 are radially disposed, optionally, at about the same distance from a center and/or edge of the device. Where, in some embodiments, protrusions 2634 and cavities 2630 alternate along the contour.

Referring now to FIG. 28, in some embodiments, a cavity/ies 2934 occupies a central region of a surface of the device and protrusions 2030 are disposed at a radial distance (e.g. with rotational symmetry) from the central region. In some embodiments, elements 2934, 2030 are reversed, device having protrusion/s 2934 and cavity/ies 2030.

FIG. 29A is a simplified schematic cross sectional view of a portion of an eye surface, according to some embodiments of the invention.

FIG. 29B is a simplified schematic cross section view of an ophthalmic device 2900 on an eye surface, according to some embodiments of the invention.

FIG. 29C is a simplified schematic cross section view of an ophthalmic device 2900 on an eye surface, according to some embodiments of the invention.

In some embodiments, above a stroma 2960 is an eye epithelial layer 2958 over which resides an aqueous tear film layer 2956, above which resides a lipid layer 2954.

In some embodiments, FIG. 29A illustrates a cross section of eye anatomy, for example prior to application of device 2900 on the eye.

In some embodiments, FIG. 29B illustrates device 2900 and eye anatomy immediately and/or soon after application of device 2900.

In some embodiments, FIG. 29C illustrates device 2900 and eye anatomy a time period after application of device where, in some embodiments, the time period is about 1 minute to 1 hour after application.

Referring now to FIG. 29B. In some embodiments, device body 2900 includes a posterior surface 2916 and an anterior surface 2918. In some embodiments, body 2900 tapers in thickness towards edges of the body.

In some embodiments, device 2900 includes cavities 2930, 2932 which, in some embodiments, are disposed on posterior surface 2916.

In some embodiments, after application of the device tear fluid fills cavities 2932, 2934 and epithelial 2958 is as before application of the device. In some embodiments, tear fluid e.g. an aqueous and/or a lipid covers the device (not illustrated).

Referring now to FIG. 29C, in some embodiments, after a time period, in eye tissue conforms to a shape of device 2900. For example, epithelial tissue 2960 locally protrudes 2960 towards cavities 2932 e.g. under suction at the cavity entrances. Potentially epithelial protrusion/s 2960 anchor device 2900 in position e.g. reducing likelihood of movement and/or expelling of the device.

FIGS. 30A-C are simplified schematic cross sectional views of a portion of a device 3000 on an eye surface 3058, according to some embodiments of the invention.

In some embodiments, FIG. 30A illustrates device 3000 and eye anatomy 3058 immediately and/or soon after application of device 3000.

In some embodiments, FIG. 30B illustrates device 3000 and eye anatomy 3058 a first time period after application of device. Where, in some embodiments, a first time period is 1 minute to 1 hour.

In some embodiments, FIG. 30C illustrates device 3000 and eye anatomy 3058 a second time period after the cross section illustrated in FIG. 30B, for example, a further 1 minute to 1 hour after illustration of device 3000 and eye anatomy 3058 in FIG. 30B.

Referring now to FIG. 30A. In some embodiments, device body 3000 includes a posterior surface 3016 which includes a cavity 3030 and a protrusion 3034.

In some embodiments, after application of the device tear fluid fills cavities 3032, 3034 and epithelial 3058 is as before application of the device.

Referring now to FIG. 30B, in some embodiments, after a first time period, in eye tissue conforms to a shape of device 3000. For example, epithelial tissue 2058 locally protrudes 3060 towards cavity 3030 and/or recesses to form a recession 3062 in pliable epithelia tissue at a region adjacent to protrusion 3034. Where recessed material, in come embodiments, potentially anchors device 3000, potentially reducing likelihood of movement and/or expelling of device 3000.

Referring now to FIG. 30C, in some embodiments, biodegrading and/or bioerosion and/or has mechanically erosion of device 3000 has occurred. Where, in some embodiments, protrusion 3034 has reduced in size (e.g. in one or more dimension) and/or corner's of protrusion 3034 have rounded. Where, in some embodiments, cavity 3030 corners have been rounded. In some embodiments, (not illustrated) the cavity becomes broader in one or more dimension and/or changes depth e.g. becomes shallower or deeper.

In some embodiments, proximal surface 3016 of FIG. 30C illustrates exemplary proximal surface shape, for example, including protrusion/s 3034 and/or cavity/ies 3030.

FIG. 31A is a simplified schematic cross section view of an ophthalmic device 3100 on an eye surface 3104, according to some embodiments of the invention.

FIG. 31B is a simplified schematic view of an ophthalmic device 3100, according to some embodiments of the invention.

FIG. 31C is a simplified schematic to view of an ophthalmic device 3100, according to some embodiments of the invention.

In some embodiments, device 3100 includes a posterior surface 3116 and an anterior surface 3118.

In some embodiments, device 3100 includes a plurality of layers 3110, 3112. Where, in some embodiments, layers generally follow surfaces of the device.

In some embodiments, a first layer 3110 is adjacent to and/or in contact with eye surface 3104 and/or forms at least a part of posterior surface 3116. In some embodiments, first layer 3110 includes mucoadhesive material.

In some embodiments, a second layer 3112 contacts, at least periodically, an inner surface of an eyelid, and/or forms at least part of anterior surface 3114. In some embodiments, second layer has a smooth outer surface and/or includes lubricious material. In some embodiments, one or both of first and second layers 3110, 3112, include and/or elute therapeutic material/s.

FIG. 31B, in some embodiments, illustrates determining of an extent of device 3100. Where, extent is, one or more dimension and/or average of two or more dimensions of a bounding box 3164 which is a smallest cuboid shape into which device 3100 fits.

In some embodiments, device 3100 includes one or more additional layer (e.g. as described elsewhere in this document.

In some embodiments, the ophthalmic device has a thickness 3128 (e.g. a maximum thickness and/or average thickness of a central 50% of the device) of less than 100 microns. In some embodiments, the ophthalmic device has a thickness of between about 1 to about 200 microns. In some embodiments, the device has a thickness of about 1, or about 2, or about 3, or about 4, or about 5, or about 6, or about 7, or about 8, or about 9, or about 10, or about 15, or about 20, or about 25, or about 30, or about 35, or about 40, or about 45, or about 50, or about 55, or about 60, or about 70, or about 80, or about 90, or about 100, or about 110, or about 120, or about 130, or about 140, or about 150, or about 160, or about 170, or about 180, or about 190, or about 200 microns. In some embodiments, the device has a thickness of between about 10 to about 100 microns.

In some embodiments, a first (e.g. mucoadhesive) layer 3166 and/or a second (e.g. lubricous) layer 3164 and/or an optional additional intermediate layer or layers (e.g. as described elsewhere in this document) has a thickness (e.g. a maximum thickness and/or average thickness at a central 50% of the device) of less than 100 microns. In further embodiments, one or more layer has a thickness of between about 1 to about 200 microns. In some embodiments, lubricious layer and/or a mucoadhesive layer and/or an intermediate layer has a thickness of about 1 microns, 2 microns, 3 microns, 4 microns, 5 microns, 6 microns, 7 microns, 8 microns, 9 microns, 10 microns, 15 microns, 20 microns, 25 microns, 30 microns, 35 microns, 40 microns, 45 microns, 50 microns, 55 microns, 60 microns, 70 microns, 80 microns, 90 microns, 100 microns, 110 microns, 120 microns, 130 microns, 140 microns, 150 microns, 160 microns, 170 microns, 180 microns, 190 microns, 200 microns. In some embodiments, one or more layer has a thickness of between about 1 to about 10 microns.

In some embodiments, one or more layer has about the same thickness as one or more other layer. In some embodiments, one or more layer has a different thickness than one or more other layer. In some embodiments, one or more layer has non-uniform thickness. For example, thinning from a central region of the device outward towards edge region/s of the device. For example, a layer having cavities and/or holes and/or protrusion/s.

FIGS. 32-37 are simplified schematic cross section views of portions of ophthalmic devices, according to some embodiments of the invention.

In some embodiments, in FIGS. 32-37, shaded areas indicate presence of therapeutic ingredient/s.

Referring now to FIG. 32 and FIG. 35, in some embodiments, a second layer 3212, 3512 (e.g. including one or more feature as described regarding second layer 3112 FIGS. 31A-C) comprises therapeutic ingredient/s. For example, dispersed within second layer 3112 and/or located within one or more region 3514 of second layer 3512.

Referring now to FIG. 33 and FIG. 36, in some embodiments, a first layer 3310, 3610 (e.g. including one or more feature as described regarding first layer 3110 FIGS. 31A-C) comprises therapeutic ingredient/s. For example, dispersed within second layer 3110 and/or located within one or more region 3614 of second layer 3610.

Referring now to FIG. 34 and FIG. 37, in some embodiments, both a first layer 3410, 3710 (e.g. including one or more feature as described regarding first layer 3110 FIGS. 31A-C) and a second layer 3412, 3712 (e.g. including one or more feature as described regarding second layer 3112 FIGS. 31A-C) comprises therapeutic ingredient/s. For example, dispersed within first layer 3410 and/or second layer 3412 and/or located within one or more region 3714 of second layer 3712 and/or first layer 3710. Where, in some embodiments, (not illustrated) one of the layers hosts a portion which has therapeutic material and the other layer has therapeutic material dispersed within it. In some embodiments, discrete region/s including therapeutic material include different therapeutic material than those layers which have therapeutic material dispersed within them. In some embodiments, discrete region/s are encapsulated by other material, the material for example, in some embodiments, eroding before the therapeutic material starts to elute into the eye.

FIGS. 38-44 are simplified schematic cross sectional views of devices 3800, 3900, 4000, 4100, 4200, 4300, 4400, according to some embodiments of the invention.

Figure 38:
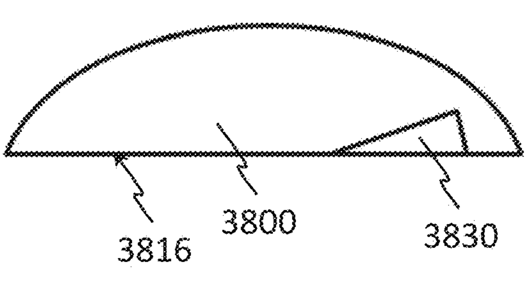
Figure 39:
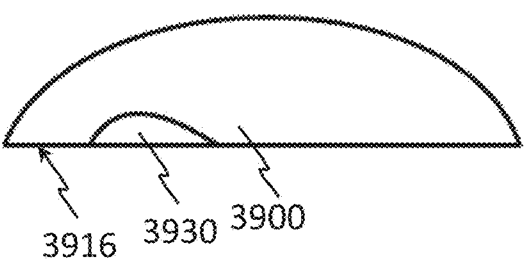
Figure 40:
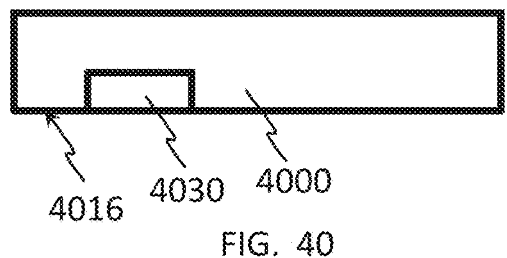
Figure 41:
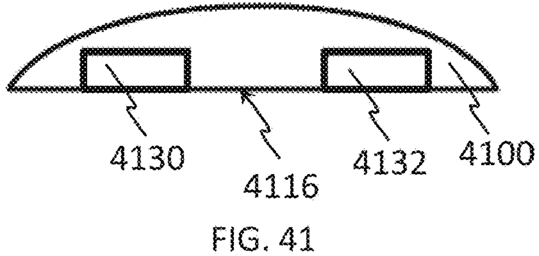

In some embodiments, a device has a posterior surface which is flat or high radius of curvature e.g. posterior surface 3816 of device 3800 FIG. 38, e.g. posterior surface 3916 of device 39 FIG. 39, e.g. posterior surface 3406 of device 4000 FIG. 40, e.g. posterior surface 4116 of device 4100 FIG. 41. Where, in some embodiments, a high radius of curvature is more than 5 mm, or more than 10 mm, or more than 9.6 mm or 8-12 mm, or 9-11 mm, or lower or higher or intermediate radii of curvature or ranges.

In some embodiments, a device has a posterior surface which is concave, e.g. posterior surface 4216 of device 4200, e.g. posterior surface 4316 of device 4300, e.g. posterior surface 4416 of device 4400. Where, in some embodiments, concave posterior surface 4216, 4316, 4416, includes one or more feature as illustrated in and/or described regarding concave and/or curved posterior/s elsewhere in this document.

In some embodiments, a device and/or a cross section of a device includes a single cavity e.g. where, in some embodiments, element 3830, 3930, 4030 of FIG. 38-40 respectively is a cavity. Where, in some embodiments, the cavity 3830, 3930, 4030 is disposed on a posterior surface 3816, 3916, 4016, of the device.

In some embodiments, a device and/or a cross section of a device includes a single portion with different material, for example, mucoadhesive material e.g. where, in some embodiments, element 3830, 3930, 4030 of FIG. 38-40 respectively is a cavity. Where, in some embodiments, the mucoadhesive portion 3830, 3930, 4030 is disposed on a posterior surface 3816, 3916, 4016, respectively of the device.

Figure 42:
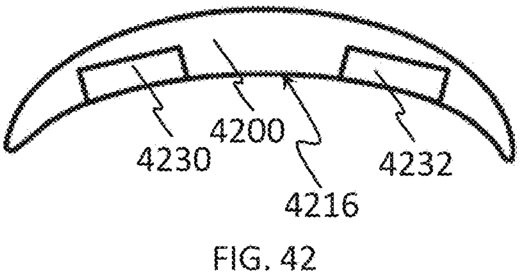

Referring now to FIG. 41 and FIG. 42. In some embodiments, a device and/or a cross section of a device has a single portion with different material 4130, 4230 e.g. mucoadhesive material and has a single cavity 4132, 4232. Where, in some embodiments, cavity 4130, 4230 and different material portion 4132, 4232 are disposed on a posterior surface 4116, 4216 of device 4100, 4200 respective.

In some embodiments, a device and/or a cross section of a device has two portions of different material/s where portions 4130, 4132, of device 4100 and/or portions 4230, 4232 of device 4200 have the same material or different materials.

In some embodiments, a device 4100, 4200 and/or a cross section of the device has two cavities 4130, 4132, and 4230, 4232 respectively.

Figure 43:
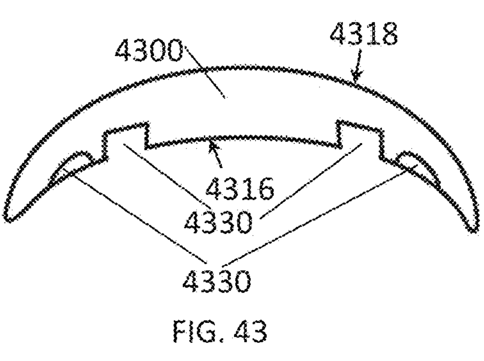
Figure 44:
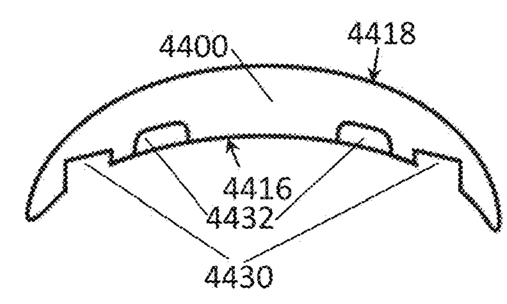

Referring now to FIG. 43 and FIG. 44, in some embodiments, a device 4300, 4400, has both more than one concavity 4330, 4432 and more than one different material portion 4332, 4432 all of which, in some embodiments, are disposed on posterior surfaces 4316, 4416 of device 4300, 4400 respectively. In some embodiments, one or more of the cavities and/or one or more of the different material portions are located within a body of the device and/or on a different device surface, for example, an anterior surface 4318, 4418 of the device.

Referring now to FIG. 43, in some embodiments, cavity/ies 4330 are disposed on posterior surface 4316 more centrally with respect to surface 4316 and/or device body 4300 than different material (e.g. mucoadhesive) portion/s 4332.

Referring now to FIG. 44, in some embodiments, different material (e.g. mucoadhesive) portion/s 4432 are disposed on posterior surface 4416 more centrally with respect to surface 4416 and/or device body 4400 than cavity/ies 4430.

FIGS. 45-50 are simplified schematic cross sectional views of double layer devices 4500, 4600, 4700, 4800, 4900, 5000, according to some embodiments of the invention.

In some embodiments, device 4500, 4600, 4700, 4800, 4900, 5000 has a posterior surface 4516, 4616, 4716, 4816, 4916, 5016 respectively and an anterior surface 4518, 4618, 4718, 4818, 4918, 5018 respectively.

In some embodiments, device 4500, 4600, 4700, 4800, 4900, 5000 includes a first layer 4510, 4610, 4710, 4810, 4910, 5010, and a second layer 4512, 4612, 4712, 4812, 4912, 5012. Where, in some embodiments, first layer has one or more feature as described regarding and/or illustrated regarding first layer 3110 FIGS. 31A-C and/or one or more of first layer 3210, 3210, 3310, 3410, 3510, 3610, 3710, FIGS. 32-37 respectively. Where, in some embodiments, second layer has one or more feature as described regarding and/or illustrated regarding second layer 3112 FIGS. 31A-C and/or one or more of second layer 3212, 3212, 3312, 3412, 3512, 3612, 3712, FIGS. 32-37 respectively.

In some embodiments, a device has a posterior surface which is flat or has low curvature (e.g. as defined elsewhere in this document) in dry and/or hydrated form. For example, posterior surface 4516 FIG. 45, posterior surface 4616 FIG. 46, posterior surface 4716 FIG. 47, posterior surface 4916 FIG. 49.

Figure 45:
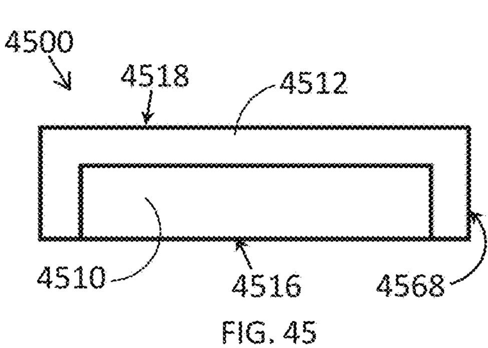
Figure 47:
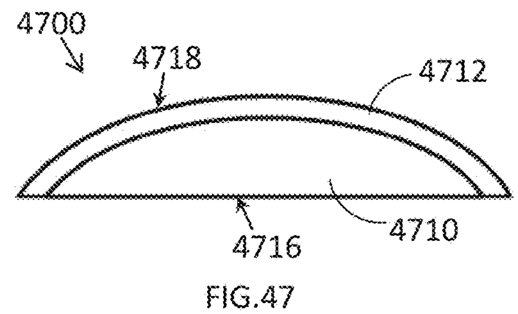

Referring now to FIG. 45 and FIG. 47, in some embodiments, a second layer 4512, 4712 (e.g. containing lubricous material) extends around a body of the device, for example, covering edge/s 4568 of the device and/or forming a part/s (e.g. at edge/s) of a proximal surface of the device 4516, 4716.

Figure 46:
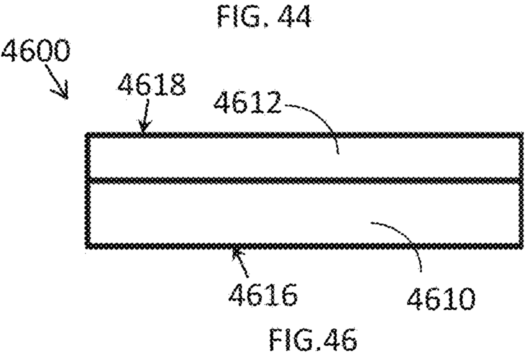

Referring now to FIGS. 45-47, in some embodiments, a first and/or second layer has about uniform thickness across an area of a device and/or along one or more cross section of the device. For example, layers 4510, 4512 FIG. 45, layers 4610, 4612, layer 4712 FIG. 47.

Referring now to FIGS. 47-50. In some embodiments, one or more layer has one or more of a maximal thickness at a center and/or central region of the device and reducing thickness moving towards edge/s of the device from the central region. For example, layer 4710 FIG. 47, layers 4810, 4812 FIG. 48, layers 4910, 4912 FIG. 49, layer 5012 FIG. 50.

FIG. 45, in some embodiments, illustrates a device 4500 with flat and/or low curvature posterior 4516 and anterior surfaces 4518, where second layer 4512 extends around edges of device 4500 to form a portion of anterior surface 4518. Where the layers are individually of about uniform thickness.

FIG. 46, in some embodiments, illustrates a device with flat and/or low curvature posterior 4616 and anterior surfaces 4618 and where the layers are individually of about uniform thickness.

FIG. 47, in some embodiments, illustrates a device 4700 with flat and/or lower curvature posterior surface 4716 and a convex anterior surface 4718 and where second layer 4712 extends around edges of device 4700 to form a portion of anterior surface 4718. In some embodiments, second layer 4712 is about uniform thickness. In some embodiments, first layer 4710 has a maximal thickness at a center and/or central region of the device and reducing thickness moving towards edge/s of device 4700 from the central region.

Figure 48:
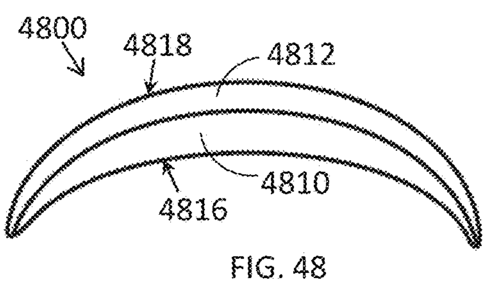

FIG. 48, in some embodiments, illustrates a device 4800 with both a concave posterior surface 4816 and a convex anterior surface 4818. Where, in some embodiments, both first layer 4810 and second layer 4812, have a maximal thickness at a center and/or central region of the device and reducing thickness moving towards edge/s of device 4800 from the central region.

Figure 49:
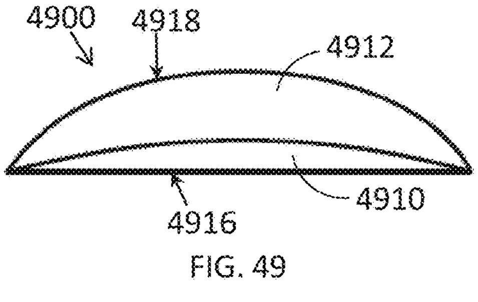

FIG. 49, in some embodiments, illustrates a device 4900 where posterior surface 4916 is flat or has low curvature and where anterior surface 4918 is convex. Where, in some embodiments, both first layer 4910 and second layer 4912, have a maximal thickness at a center and/or central region of the device and reducing thickness moving towards edge/s of device 4900 from the central region.

Figure 50:
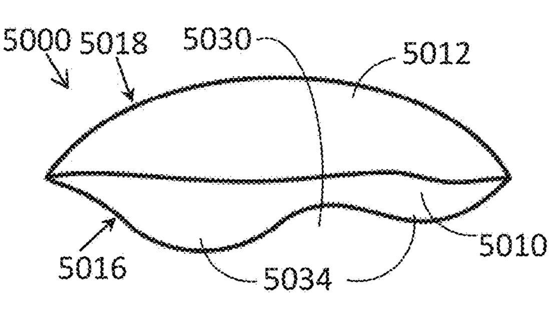

FIG. 50, in some embodiments, illustrates a device 5000 where, in some embodiments, posterior surface has a bounding plane which is convex. In some embodiments, posterior has one or more protrusion 5034 and/or one or more cavity 5030. For example, a cross section with two protrusions 5034 defining between them a cavity 5030. In some embodiments, thickness of one or both layers is irregular. In some embodiments, posterior surface 5016 has an irregular shape.

FIGS. 51-58 are simplified schematic cross sectional views of multi-layer devices 5100, 5200, 5300, 5400, 5500, 5600, 5700, 5800 according to some embodiments of the invention.

In some embodiments, device 5100, 5200, 5300, 5400, 5500, 5600, 5700, 5800 has a posterior surface 5116, 5216, 5316, 5416, 5516, 5616, 5716, 5816 respectively and an anterior surface 5118, 5218, 5318, 5418, 5518, 5618, 5718, 5818 respectively.

In some embodiments, device 5100, 5200, 5300, 5400, 5500, 5600, 5700, 5800 includes a first (e.g. mucoadhesive) layer 5110, 5210, 5310, 5410, 5510, 5610, 5710, 5810, and a second (e.g. lubricous) layer 5112, 5212, 5312, 5412, 5512, 5612, 5712, 5812. Where, in some embodiments, the first layer has one or more feature as described regarding and/or illustrated regarding first layer 3110 FIGS. 31A-C and/or one or more of first layer 3210, 3210, 3310, 3410, 3510, 3610, 3710, FIGS. 32-37 respectively. Where, in some embodiments, the second layer has one or more feature as described regarding and/or illustrated regarding second layer 3112 FIGS. 31A-C and/or one or more of second layer 3212, 3212, 3312, 3412, 3512, 3612, 3712, FIGS. 32-37 respectively.

In some embodiments, device 5100, 5200, 5300, 5400, 5500, 5600, 5700, 5800 includes an intermediate layer 5136, 5236, 5336, 5436, 5536, 5636, 5736, 5836 respectively. In some embodiments, the intermediate layer is disposed between the first and second layers. Where, in some embodiments, the intermediate layer is covered by other layers e.g. as illustrated in FIGS. 51-55 and FIGS. 57-58. In some embodiments, the intermediate layer includes therapeutic material (e.g. dispersed within the layer and/or in portion/s of the layer).

Figure 51:
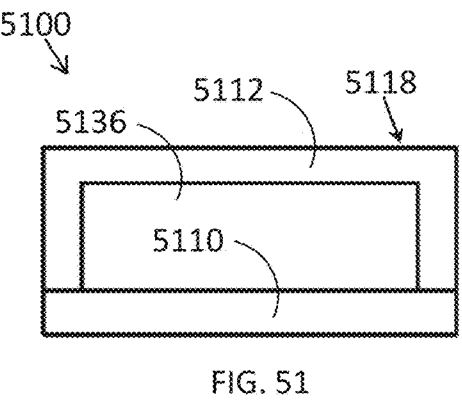

FIG. 51, in some embodiments, illustrates a device 5100 having flat and/or low curvature posterior 5116 and anterior 5118 surfaces. Where, in some embodiments, second surface extends to cover edges of device 5100 e.g. to enclose sides of intermediate surface 5136. In some embodiments, one or more (e.g. all) of first 5110, second 5112 and third layers 5136 have about uniform thickness. In some embodiments, a thickness of intermediate layer 5136 is thicker than one or more of the other layers, for example, 1.5-10 times thicker or lower or higher or intermediate multiples or ranges.

Figure 52:
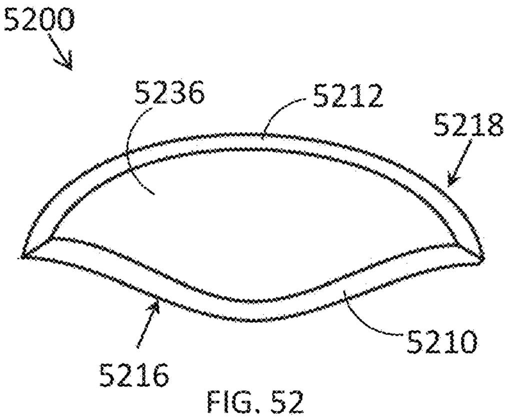

FIG. 52, in some embodiments, illustrates a device 5200 where a posterior surface 5216 is convex. In some embodiments, thicknesses of a first 5210 and second layer 5212 are about the same and, in some embodiments about uniform. In some embodiments, an intermediate layer 5236 has a thicker central region, reducing in thickness towards edges of device 5200. In some embodiments, an average and/or maximal thickness of intermediate layer 5236 is at 1.5-10 times thicker than thickness of one or both of the first 5210 and second 5212 layers.

Figure 53:
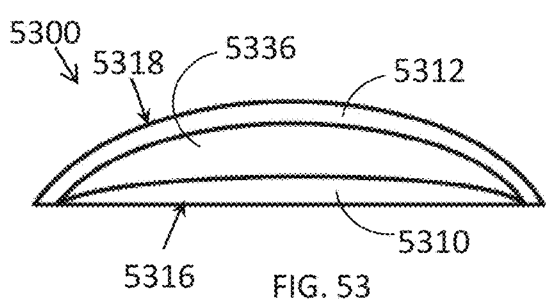

FIG. 53 in some embodiments, illustrates a device 5300 where each of a first layer 5310, an intermediate layer 5336, and a second layer 5312 have a thicker central region, the layers reducing in thickness towards edges of device 5300. In some embodiments, second layer 5312 is disposed around device 5300 to form part of posterior surface 5316. In some embodiments, posterior surface 5316 has higher radius of curvature than anterior surface 5318 (e.g. radius of curvatures including one or more feature as described elsewhere in this document e.g. in the overview section).

Figure 54:
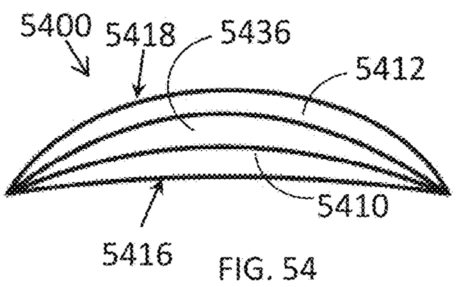

FIG. 54, in some embodiments, illustrates a device 5400 where each of a first layer 5410, an intermediate layer 5436, and a second layer 5412 have a thicker central region, the layers reducing in thickness towards edges of device 5400. In some embodiments, thicknesses of the layers are about the same at a central region of the device and/or throughout one or more cross section of the device.

Figure 55:
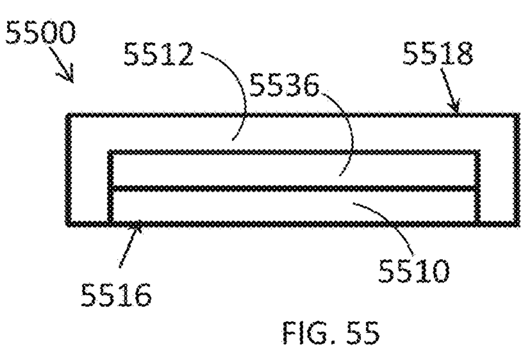

In some embodiments, device 5500 of FIG. 55 has the same features as device 5100 of FIG. 51 except intermediate layer 5536 is, in some embodiments, about the same thickness as one or both of a first layer 5510 and a second layer 5512.

Figure 56:
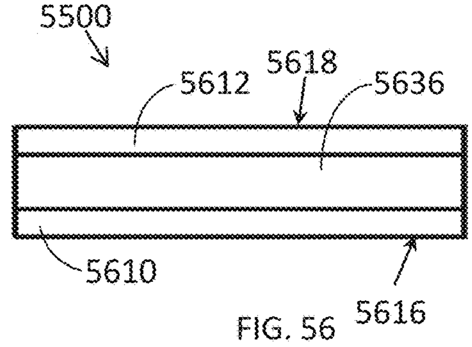

FIG. 56, in some embodiments, illustrates a device 5600 where each layer 5610, 5612, 5636 have constant thickness along the illustrated cross section. In some embodiments, intermediate layer 5636 includes therapeutic material. In some embodiments, intermediate layer 5636 is thicker than one or both of the other layers 5612, 5610. For example, a thickness of 1.5-10 times that of the mucoadhesive 5610 and/or lubricious 5612 layers. In some embodiments, intermediate layer 5636 includes a plurality of layers.

Figure 57:
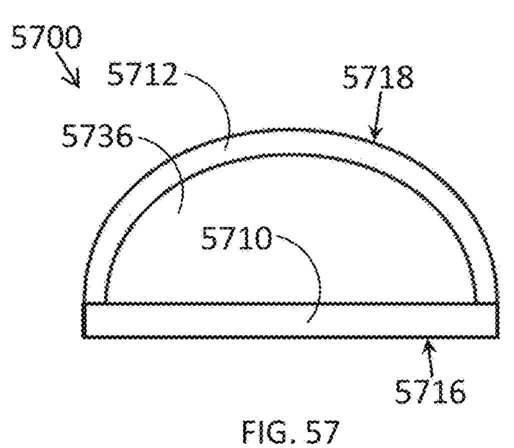

FIG. 57, in some embodiments, illustrates a device 5700 which has a convex anterior surface 5718, and a flat or low curvature posterior surface 5716. In some embodiments, mucoadhesive layer 5716 has uniform thickness across one or more cross section of the device. In some embodiments, lubricous layer 5712 has uniform thickness on its path around a circumference of intermediate layer 5736. In some embodiments, intermediate layer 5736 is thicker in a central region of one or more cross section of device 5700 and, in some embodiments, has reducing thickness towards edge/s of the device. In some embodiments, lubricous layer 5712 does not form part of posterior surface 5716.

Figure 58:
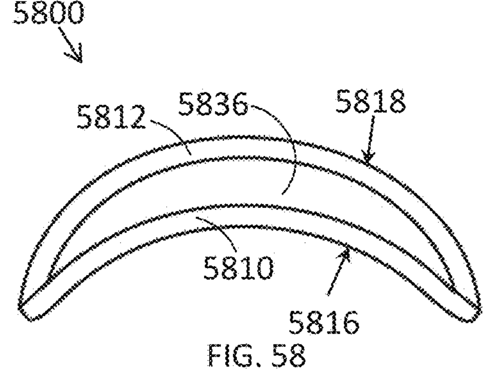

FIG. 58, in some embodiments, illustrates a device 5800 which has a convex anterior surface 5818, and a concave posterior surface 5816. In some embodiments, mucoadhesive layer 5816 has uniform thickness across one or more cross section of the device. In some embodiments, lubricous layer 5812 has uniform thickness on its path around a circumference of intermediate layer 5836. In some embodiments, intermediate layer 5836 is thicker in a central region of one or more cross section of device 5800 and, in some embodiments, has reducing thickness towards edge/s of the device. In some embodiments, lubricous layer 5812 does not form part of posterior surface 5816.

FIGS. 59-61 are simplified schematic cross sectional views of multi-layer devices 5900, 6000, 6100, according to some embodiments of the invention.

FIGS. 59-61, in some embodiments, illustrate therapeutic ingredient elution as illustrated in the figures by arrows.

Referring now to FIG. 59, in some embodiments, an intermediate layer 5936 includes therapeutic material and is not covered by other layer/s at edges of device 5900. The layer, in some embodiments, eluting therapeutic ingredient/s through edges e.g. as illustrated by arrows.

Referring now to FIG. 60, in some embodiments, (e.g. alternatively or additionally to eluting through edges of the device) an intermediate layer 6036 includes therapeutic material and is not fully covered by a second lubricous layer 6012, therapeutic ingredient/s eluting through the second layer. For example, through channel/s and/or holes 6030 in the layer 6012 e.g. as illustrated by arrows on FIG. 60. In some embodiments, alternatively or additionally to having channel/s and/or holes, second layer 6012 includes material which allows diffusion through the material of therapeutic ingredient/s.

Referring now to FIG. 61, in some embodiments, (e.g. alternatively or additionally to eluting through edges and/or through a second lubricious surface 6112 of the device) an intermediate layer 6136 includes therapeutic material and is not fully covered by a first mucoadhesive layer 6010, therapeutic ingredient/s eluting through the first layer. For example, through channel/s and/or holes 6130 in the layer 6110 e.g. as illustrated by arrows on FIG. 61. In some embodiments, alternatively or additionally to having channel/s and/or holes, first layer 6110 includes material which allows diffusion through the material of therapeutic ingredient/s.

Exemplary Disintegration of Exemplary Ophthalmic Devices

FIGS. 62A-F are simplified schematic cross sections of a portion of a device as residence time of the device progresses, according to some embodiments of the invention.

FIG. 63 is a flowchart of a disintegration progression of a device, according to some embodiments of the invention.

FIG. 62A, in some embodiments, illustrates the device layer structure before the device is placed on an eye surface. The device including a first mucoadhesive layer 6210, an intermediate layer 6236 and a second lubricous layer 6212.

At 6300, in some embodiments, device 6200 is positioned on an eye surface 6258.

At 6302, in some embodiments, mucoadhesive layer 6210 degrades and/or dissolves and/or erodes, for example, transitioning device 6200 from the configuration illustrated in FIG. 62B to that illustrated in FIG. 62C.

At 6304, in some embodiments, intermediate layer 6236 partially degrades and/or dissolves and/or erodes, for example, transitioning device 6200 from the configuration illustrated in FIG. 62C to that illustrated in FIG. 62D and then to that illustrated in FIG. 62E.

At 6306, in some embodiments, lubricious layer 6212 dissolves, and/or degrades and/or erodes, for example, transitioning the eye from the configuration illustrated in FIG. 62E to that illustrated in FIG. 62F.

FIGS. 64A-C are simplified schematic cross sections of a device 6400 as residence time of the device progresses, according to some embodiments of the invention.

In some embodiments, FIGS. 64A-C illustrate a portion of a device (e.g. a central portion, where edges are not illustrated).

In FIGS. 64A-C, in some embodiments, like shading indicates portions with the same material characteristics (e.g. lubricious, mucoadhesive, containing therapeutic material). In some embodiments, device 6400 includes a posterior surface 6416 and an anterior surface 6418, where one or both of surfaces 6416, 6418 have one or more feature (e.g. curvature, thickness) as illustrated and/or described elsewhere in this document.

In some embodiments, device 6400 includes a first mucoadhesive layer 6410, and a second lubricious layer 6412.

Where, in some embodiments, mucoadhesive layer 6410 covers most (e.g. over 55-99%, or 60-90% or lower or higher or intermediate ranges or percentages) or all of posterior surface 6416. A potential benefit of a mucoadhesive layer with a large surface are is increased stability, for example, associated with increased adhesion to the eye surface.

Where, in some embodiments, lubricious layer 6412 covers a portion of anterior surface 6418 e.g. edge region/s.

In some embodiments, device 6400 includes a third layer 6470. Where, in some embodiments, third layer 6470 includes rapidly dissolving and/or degrading and/or abrading material. Where, in some embodiments, the third layer disintegrates more rapidly than other layer/s of the device 6400. For example, as illustrated in transition between FIG. 64A and FIG. 64B where third layer 6470 has reduced in thickness.

In some embodiments, mucoadhesive layer 6410 is also more readily eroded (e.g. associated with proximity to the eye surface which is not illustrated and/or associated with material characteristics of the layer) and/or dissolved and/or degraded (e.g. associated with material characteristics) than one or more other layer of the device. For example, as illustrated in transition between FIG. 64A and FIG. 64B where mucoadhesive layer 6410 has reduced in thickness.

In some embodiments, intermediate layer 6436 includes therapeutic material, where upon being revealed by disappearance of third layer 6470, intermediate layer 6436 begins to dissolve and/or degrade and/or erode, e.g. eluting medication. In some embodiments, intermediate layer is more readily dissolved and/or degraded and/or eroded than one other layer e.g. lubricious layer 6412 and/or mucoadhesive layer 6416 e.g. as illustrated by cavities 6430 having formed in intermediate layer 6436.

FIGS. 65A-D are simplified schematic cross sections of a device as residence time of the device progresses, according to some embodiments of the invention.

In some embodiments, FIGS. 65A-C illustrate a portion of a device (e.g. a central portion, where edges are not illustrated).

In FIGS. 65A-C, in some embodiments, like shading indicates portions with the same material characteristics (e.g. lubricious, mucoadhesive, containing therapeutic material).

In some embodiments, device 6500 has a posterior surface 6516 and an anterior surface 6518, where one or both of surfaces 6516, 6518 have one or more feature (e.g. curvature, thickness) as illustrated and/or described elsewhere in this document.

In some embodiments, device 6500 includes a first mucoadhesive layer 6510, and a second lubricious layer 6512. In some embodiments, device 6500 includes an intermediate therapeutic material 6536 layer.

Where, in some embodiments, one or more than one of (e.g. all of) lubricious layer 6512, mucoadhesive layer 6516, are disposed at edge region/s of device 6500, for example, not being present in a central region of device 6500.

In some embodiments, device 6500 includes a third layer 6570. Where, in some embodiments, third layer 6570 includes rapidly dissolving and/or degrading and/or abrading material. Where, in some embodiments, the third layer disintegrates more rapidly than other layer/s of the device 6500. For example, as illustrated in progression from FIG. 65A, to FIG. 65B, to FIG. 65C where third layer 6570 reduces in thickness and then in transition between FIG. 65C to FIG. 65 D where third layer 6570 disappears. In some embodiments, e.g. illustrated in transition between FIG. 65A to FIG. 65B, mucoadhesive layer 6510 disappears first, e.g. exposing intermediate therapeutic material layer 6536. In some embodiments, third layer 6570 disappears leaving one or more remaining layer/s at edges of device e.g. as illustrated in FIG. 65D. In some embodiments, device 6500 is placed over a region of the eye e.g. covering a cornea, where disappearance of third layer 6570 creates a hole in the device e.g. to position device 6500 on sclera surrounding cornea.

FIG. 66 is a simplified schematic cross section of a device 600, according to some embodiments of the invention.

In some embodiments, FIG. 66 illustrates a portion of a device (e.g. a central portion, where edges are not illustrated).

In FIG. 66, in some embodiments, like shading indicates portions with the same material characteristics (e.g. lubricious, mucoadhesive, containing therapeutic material).

In some embodiments, device 6600 has a posterior surface 6616 and an anterior surface 6618, where one or both of surfaces 6616, 6618 have one or more feature (e.g. curvature, thickness) as illustrated and/or described elsewhere in this document.

In some embodiments, device 6600 includes a first mucoadhesive layer 6610, and a second lubricious layer 6612. In some embodiments, device 6600 includes an intermediate therapeutic material 6636 layer. In some embodiment, mucoadhesive layer 6610 covers most or all of device posterior surface 6616.

Where, in some embodiments, one or more than one of lubricious layer 6612, and intermediate therapeutic material layer 6636, are disposed at edge region/s of device 6600, for example, not being present in a central region of device 6600.

In some embodiments, device 6600 includes a third layer 6670. Where, in some embodiments, third layer 6670 includes rapidly dissolving and/or degrading and/or abrading material. Where, in some embodiments, the third layer disintegrates more rapidly than other layer/s of the device 6600.

In some embodiments, device 6600 includes a degradable layer 6672, which, in some embodiments, degrades more rapidly than one or more of mucoadhesive layer 6610, lubricious layer 6612 and therapeutic layer 6636. Where, in some embodiments, degradable layer 6672 degrades and/or dissolves and/or erodes less rapidly than third layer 6670.

Where, in some embodiments, third layer 6670 is first to disappear, for example, revealing portion/s of therapeutic layer 6636 to initiate and/or increase therapeutic material elution. Where, in some embodiments, degrading layer 6672 then erodes e.g. to further reveal the therapeutic material layer and/or to disintegrate the device.

FIG. 67 is a simplified schematic cross section of a device 6700, according to some embodiments of the invention.

In some embodiments, device 6700 has a posterior surface 6716 and an anterior surface 6718, where one or both of surfaces 6716, 6718 have one or more feature (e.g. curvature, thickness) as illustrated and/or described elsewhere in this document.

In some embodiments, anterior surface 6718 includes a low curvature (or flat) region disposed at a central region of device 6700. In some embodiments, curves towards posterior surface 6716.

In some embodiments, device 6700 includes a first mucoadhesive layer 6710, and a second lubricious layer 6712. In some embodiments, device 6700 includes an intermediate therapeutic material 6736 layer. In some embodiments, second surface 6712 curves around edge/s of device 6700, for example, in some embodiments, forming an edge portion of posterior surface 6716.

In some embodiment, mucoadhesive layer 6710 occupies edge regions of device 6700 and/or posterior surface 6716.

A potential advantage mucoadhesive being disposed locally at edges of device 6700 e.g. as recessions in intermediate therapeutic material 6736 layer is adhesive advantages of mucoadhesive material while maintaining more of a volume of the device for therapeutic material. In some embodiments, intermediate therapeutic material layer 6736 forms at least a part of posterior surface 6716. A potential benefit being ingredient elution rapidly after attachment of device 6700 to an eye surface.

Exemplary Materials

In some embodiments, one or more portion of an ophthalmic device includes one or more of; film forming agent/s, plasticizer/s, binder/s, and excipient/s.

In some embodiments the device contains one or more of anti-infective and anti-inflammatory pharmacotherapies (including: Glucocorticoids, NTHEs, and biological agents or combination of them) and other technologies and means, such as: silver, gold, zinc oxide, titanium dioxide, selenium, copper, polyammonium salts, signaling inhibiting and antimicrobial peptides, cytokines, enzymes.

In some embodiments, the device comprises Thermosensitive and/or PH-sensitive and/or Ion sensitive compounds.

Without being bound by theory, the molecular weight of the compounds and/or a degree of cross-linking within materials of the device contribute to device consistency (e.g. hardness and/or rigidity) and/or contribute to the device rheological properties (e.g. viscosity). Where, in some embodiments, molecular weight and/or cross-linking and/or consistency and/or rheological properties define the device residence time and/or therapeutic agent release rate.

In some embodiments the device composition comprises at least one charged compound. In some embodiments the device composition comprises at least one charged compound and at least one compound having an opposite charge, constructing a PEC (Poly Electrolyte Complex) formation upon liquid adsorption.

Non-limiting exemplary material/s for:

a lubricious portion (e.g. a lubricious layer and/or film) and/or a mucoadhesive portion (e.g. a mucoadhesive layer and/or film) and/or other portion/s of the ophthalmic device include one or more of (and/or similar compound/s and/or material/s and/or polymer/s and/or combinations thereof) are herein listed:

Polyethylene-Phthalate polymer film; e.g. purchased as film (MYLAR-A®; DuPont, USA).

Polyvinyl Alcohol 4-88; e.g. purchased as powder (Merck, Germany).

Methocel LV-50; e.g. purchased as powder (DOW, USA).

Poly-Vinyl-Alcohol; e.g. purchased as powder (Merck, Germany).

Poly-Vinyl-Alcohol[PVA]:Poly-Ethylene-Glycol[PEG] graft-copolymer; e.g. e.g. purchased as powder (Kollicoat-IR®; BASF, Germany).

Hydroxy-Propyl-Cellulose polymer; e.g. purchased as powder (Klucel-LF®; Ashland, USA) Povidone (Kollidone 25; BASF, Germany).

Carbomer, Carbopol, Carbopol 971, Carbopol 974, Carbopol 934, Carbopol 2020.

Cross-linked Poly-Acrylic-Acid; e.g. purchased as powder (Carbopol 974; Lubrizol, USA).

Cross-linked Sodium Polyacrylic-Acid; e.g. purchased as powder (FavorPac®; Evonik, Germany).

Cross-linked Sodium Polyacrylic-Acid; e.g. purchased as powder (Luquasorb®; BASF, USA).

CMC Sodium, Polycarbophil, Tragacanth, Poly acrylic acid polymers, Sodium alginate, (Poly) Hydroxy Ethyl Cellulose, HPMC, Gum Karaya, Gelatin, Guar Gum, Starch, Modified starch, Pectin, *Psyllium*, Amberlite-Resin, Hydroxy Propyl cellulose.

Chitosan; e.g. purchased as powder (KiOnutrime-CsG; kitozyme, Belgium).

Chitosan; e.g. purchased as powder (Chitoclear; Premix, Iceland or 90/200/A1; Kraeber, Germany or Protasan UP CL 114, 113, 213, 214; Novamatrix, Norway).

Alginate, Gellan gum, Eudragit.

Polyethylene oxide, Carboxymethyl cellulose (CMC), Poly(methyl vinyl ether), Poly(methyl vinyl ether) co maleic anhydride, Hydroxy Propyl methyl cellulose, Methyl Ethyl cellulose, poly hydroxyethyl methacrylate.

Methylcellulose or hypromellose or Povidone (Kollidone 25; BASF, Germany), or polyvinyl pyrrolidone (PVP).

Cross-linked Poly Glutamic-Acid; e.g. purchased as powder (PGA; hayashibira, Japan).

Cross-linked Dextrane gel; e.g. purchased as powder (Sephadex G-100; GE Medical).

Lactose monohydrate; e.g. purchased as powder (Pharmatose 200, Fonterra, New Zealand).

Cellulose acetate, Ethyl cellulose, Methyl cellulose, Modified cellulose.

Silicone, Acrylates, Polyethylenes (including ultra high molecular weight, Polyethylene terephthalate), Polyester.

Polypropylene, Polytetrafluoroethylene (PTFE, ePTFE), Polyether ether ketone (PEEK), Nylon.

Biocompatible metal alloy.

Polymer foam.

Polymethyl methacrylate (PMMA), polyhydroxyethylmethacrylate (pHEMA).

Cellulose acetate butyrate, Siloxane acrylates, t-Butyl Styrene, Fluoro siloxane acrylates, perfluroethers.

Silicone Hydrogel, Lotrafilcon A, Lotrafilcon B, Galyfilcon A, Senofilcon A, Senofilcon C, Sifilcon A, Comfilcon A, Enfilcon A, Balafilcon A, Delefilcon A, Narafilcon B, Narafilcon A, Stenfilcon A, Somofilcon A, Fanfilcon A, Samfilcon A, Elastofilcon.

Tefilcon, Tetrafilcon A, Crofilcon, Helfilcon A/B, Mafilcon, Polymacon, Hioxifilcon B.

Surfilcon A, Lidofilcon A, Lidofilcon B, Netrafilcon A, Hefilcon B, Alphafilcon A, mafilcon A, Omafilcon B, Vasurfilcon A, Hioxifilcon A, Hioxifilcon D, Nelfilcon A, Hilafilcon A, Hilafilcon B, Acofilcon A, Nesofilcon A.

Bufilcon A, Deltafilcon A, Phemfilcon.

Bufilcon A, Perfilcon A, Etafilcon A, Focofilcon A, Ocufilcon B, Ocufilcon C, Ocufilcon D, Ocufilcon E, Ocufilcon F, Phemfilcon A, Methafilcon A, Methafilcon B, Vilfilcon A.

Lotrafilcon A, Balafilcon A, Senofilcon A, Galyfilcon A, Samfilcon A, Comfilcon A, Enfilcon A and similar.

PHEMA (polyhydroxyethilmethacrylate), MA (methacrylic acid), MMA (methyl methacrylate), GMA (glyceryl methacrylate), DAA (diacetone acrylamide, PVOH (polyvinyl alcohol), PVA (Poly-Vinyl-Acetate).

Silicone rubber, Acrylic resins, Polyurethane, Polypropylene, and Polymethylmethacrylate, Polycarbonate urethane, Polyimides.

polyglycolide, polylactide, polyhydroxobutyrate, hyaluronic acid, and hydrogels, poly(2-hydroxyethyl-methacrylate).

polylactic acid (PLA), Polyglycolic acid (PGA), poly (lactic-co-glycolic) acid (PLGA), and poly(caprolactone).

polyglycolide, poly-L-lactide, poly-D-lactide, poly (amino acids), polydioxanone, polycaprolactone, polygluconate, polylactic acid-polyethylene oxide copolymers, polyorthoesters, polyhydroxybutyrate, polyanhydride, polyphosphoester, poly(alpha-hydroxy acid).

polycaprolactone (PCL), polyesteramide (PEA).

Protein, Fatty acids, Amino acids, Carbohydrates, collagen.

Poloxamer, Synperonics, Pluronics, Kolliphor, Pluronic F127 (BASF), Synperonic PE/F 127 (Croda), poloxamer 188 (Pluronic® F-68), poloxamer 407 (Pluronic® F-127), polypropylene glycol, polyoxyethylene, poly(propylene oxide), carboxylated polystyrene, PEGylated polystyrene, dendrimers, Poly (amidoamine) (PAMAM).

Poly-Ethylene-Glycol (Sigma, USA).

Triethyl citrate [TEC] and Acetyl tributyl citrate [ATBC]; e.g. purchased as liquids (Merck, Germany).

Tris(hydroxymethyl)aminomethane.

DEP [Diethyl-Phthalate]; e.g. purchased as liquid (Spectrum, USA).

Glycerol Monostearate [GMS]; e.g. purchased as liquid (Cognis, Germany).

Ethanol, Methanol, Isopropyl Alcohol [IPA], Ethyl Acetate, Acetic-acid, and Acetone (BioLab, Israel) are organic solvents used for the polymers dissolving.

Hypromellose Phthalate [HP-55] and Hypromellose Acetate Succinate [AQOAT AS-LF]; e.g. purchased as powders (Shin-Etsu, Korea) CAP [Cellulose-Acetate-Phthalate] and CA [Cellulose-Acetate]; e.g. purchased as powders (Eastman, USA).

Polysaccharides (β-cyclodextrin, dextrans, inulin, etc.), sugars (glucose, lactose, leucrose, maltose, raffinose, sucrose, trehalose, etc.), Polyol (maltitol, mannitol, sorbitol, xylitol, etc.), oligosaccharides, carbohydrates.

Thermosensitive or PH-sensitive or Ion sensitive pressure sensitive deflection sensitive compounds.

Excipients, including: Antiadherents, Binders and Adhesives (including mucoadhesives), Coatings, Colors, Disintegrants, Flavors, Glidants, Lubricants, Preservatives, Sorbents, Sweeteners, Vehicles.

One or more solvent, for example, one or more of ethanol, methanol, isopropanol, methylene chloride, ethyl acetate, acetone, water, ethanol, polyols (such as glycerol, propylene glycol, polyethylene glycol).

Exemplary Lubricant Layer

In some embodiments, a lubricant portion (e.g. a lubricant layer) includes one or more of; Cellulose Acetate, Ethyl cellulose, PVA (Poly-Vinyl-Alcohol) Poly-Vinyl-Alcohol [PVA]:Poly-Ethylene-Glycol[PEG] graft-copolymer or PVA (Poly-Vinyl-Acetate) or PVA (Poly-Vinyl-Acetate) or Methyl cellulose.

Exemplary Mucoadhesive Layer

In some embodiments, the term “mucoadhesive” encompasses any compound that is capable of adhering to biological tissue. In some embodiments the mucoadhesive is a polymer. In some embodiments the mucoadhesive, in some embodiments, is charged or neutral.

In some embodiments, a mucoadhesive portion (e.g. a mucoadhesive layer) includes one or more ingredient configured to provide mucoadhesive properties.

In some embodiments, a mucoadhesive portion (e.g. a mucoadhesive layer) includes one or more, of: Poly-Vinyl-Alcohol (also called PVA or PVOH), hydroxypropylcellulose (Klucel), Polyvinyl alcohol-polyethylene glycol graft-copolymer (Kollicoat-IR), methylcellulose, hypromellose methylcellulose, hydroxypropyl methylcellulose (Methocel), Povidone (polyvinylpyrrolidone).

Exemplary Therapeutic Agents

In some embodiments, a therapeutic material portion or layer of a device according to embodiments described in this document, contains one or more therapeutic agents, for example, one or more drug and/or natural compound or synthetic compound.

In some embodiments, one or more therapeutics agents is in one or more of solid form, powder, ointment, liquid, bids (e.g. polymer bids), dispersion, solution, pellets, microparticles, microspheres, and microcapsules.

In some embodiments, therapeutic material contains one or more therapeutic agents as microparticles in the 1-1000 μm size range.

In some embodiments, therapeutic material contains active pharmaceutical ingredients (API) and/or excipients and/or combinations thereof.

In some embodiments, an ophthalmic device (e.g. according to one or more embodiment as described in this document) contains a dose of one or more therapeutic agent within a range from about 1 μg to about 10,000 μg, or above 10,000 μg, or between 0 and 1 μg, or between 1 μg and 5 μg, or between 5 μg and 10 μg, or between 10 μg and 50 μg, or between 50 μg and 100 μg, or between 100 μg and 500 μg, or between 500 μg and 1000 μg, or between 1000 μg and 5000 μg, or between 5000 μg and 10000 μg, or between 10000 μg and 30000 μg.

In some other embodiments, an ophthalmic device (e.g. according to one or more embodiment as described in this document) contains a mass of therapeutic agent of between about 1 microgram to about 20 milligrams. In some embodiments, a mass of therapeutic agent is about 1 nanogram, or about 2 nanograms, or about 3 nanograms, or about 4 nanograms, or about 5 nanograms, or about 6 nanograms, or about 7 nanograms, or about 8 nanograms, or about 9 nanograms, or about 10 nanograms, or about 11 nanograms, or about 12 nanograms, or about 13 nanograms, or about 14 nanograms, or about 15 nanograms, or about 20 nanograms, or about 30 nanograms, or about 40 nanograms, or about 50 nanograms, or about 60 nanograms, or about 70 nanograms, or about 80 nanograms, or about 90 nanograms, or about 100 nanograms, or about 200 nanograms, or about 300 nanograms, or about 400 nanograms, or about 500 nanograms, or about 600 nanograms, or about 700 nanograms, or about 800 nanograms, or about 900 nanograms or of about 1 milligram, or about 2 milligrams, or about 3 milligrams, or about 4 milligrams, or about 5 milligrams, or about 6 milligrams, or about 7 milligrams, or about 8 milligrams, or about 9 milligrams, or about 10 milligrams, or about 12 milligrams, or about 14 milligrams, or about 16 milligrams, or about 18 milligrams, or about 20 milligrams.

In some embodiments, the device is about 0.1% to about 99.5%, or about 0.5% to about 90%, drug release material e.g. in combination with pharmaceutically acceptable carrier material/s.

In some embodiments, the device has a concentration of therapeutic agent less than 0.01%, or between 0.01% and 0.1%, or between 0.1% and 1%, or between 1% and 5%, or between 5% and 10%, or between 10% and 30%, or between 30% an 60%, or between 60% and 90%, or between 90% and 100%.

In some embodiments, the ophthalmic device (e.g. a therapeutic material layer and/or region) includes one or more of the following therapeutic agents (also herein termed "therapeutic ingredients"):

Aflibercept, Atropine, Bevacizumab, Brimonidine/timolol, Ciclosporin, Ciprofloxacin, Cyclopentolate, Diisopropyl fluorophosphate, Diquafosol, Dorzolamide/timolol, chothiophate, Latanoprost/timolol, Latanoprostene bunod, Lifitegrast, Loteprednol, fluocinolone, fluorometholone, difluprednate, prednisolone, triamcinolone, rimexolone, Mydriatics and cycloplegics, Nandrolone sulfate, Naphazoline/pheniramine, Nedocromil, Netarsudil, Ofloxacin, Pegaptanib, Pilocarpine, Pirenoxine, Ranibizumab, Ripasudil, Tauroursodeoxycholic acid, Tavilermide, Tropicamide/hydroxyamfetamine, Verteporfin, Acthar, Bevacizumab, Cefazolin, Ceftazidime, Cocaine, EDTA, Gatifloxacin, Gentamicin, Idoxuridine, Iluvien®, Indocyanine Green, Infliximab, Interferon, Intravitreal Injections, Iohexol, Iopamidol, Iopamidol-M, Lissamine Green, Membrane Blue, Mitomycin, Moxifloxacin, Rituximab, Serum eye drops, Single-Use Povidone, Subconjunctival Injections, Tetracaine PF, Tobramycin, TPA, Vancomycin, Cyclopentolate, Phenylephrine, Proparacaine, Steroids, Tropicamide, Amikacin, Amphotericin-B, Dexamethasone, Mitomycin, Small molecules, Biological drugs, autoimmune drugs, anti-cancer drugsand/oragents, anti-inflammatory agents, anti-infection agents, antibiotics, cannaboids, Synthetic compounds Natural compounds Drug, in some embodiments is hydrophilic or hydrophobic Drug formulation, in some embodiments is hydrophilic or hydrophobic Excipients, including: Antiadherents, Binders, Coatings, Colors, Disintegrants, Flavors, Glidants, Lubricants, Preservatives, Sorbents, Sweeteners, Vehicles.

In some embodiments, a therapeutic material includes enhancer materials for example: for penetration enhancement and/or for membrane pore openers.

In some embodiments, a therapeutic material includes materials for improved solubility in human fluids (including serum and/or blood).

In some embodiments, a therapeutic material includes materials that activate and/or inhibits processes in the body.

In some embodiments, a therapeutic material includes prodrug form of another drug.

In some embodiments, a therapeutic material includes a biosimilar form of another drug. The therapeutics agent, in some embodiments is at any dosage form including modified release dosage form such as: immediate-release dosage, delayed-release dosage, extended-release dosage, sustained-release dosage, stimuli inducing release and/or targeted-release dosage.

Techniques for modified release dosage, in some embodiments is using any of the following release approaches: Diffusion, Dissolution, Osmotic, Ion-exchange resin, Floating, Bio-adhesive, Matrix, etc.

Processes for modified release form include: microencapsulation, molecularly imprinted polymer (MIP), 3D drug printing The therapeutics agent, in some embodiments is at any formulation contains any excipient and other compound available.

Exemplary Nanoparticle and/or Microparticle Therapeutic Agent/s

In some embodiments, a therapeutic material portion or layer of a device (e.g. according to one or more embodiment described in this document) contains one or more therapeutic agent in the form of nanoparticles and/or microparticles. In some embodiments, nanoparticle and/or microparticle therapeutic agent/s are covered and/or contain mucoadhesive compounds and/or polymer/s. Where, in some embodiments, covering of the particles/s increases residence time and/or duration of drug elution of the particle/s.

For example, Atropine microparticles.

For example, atropine sulfate in albumin-chitosan microparticles e.g. including one or more feature as described in "Formulation and characterization of atropine sulfate in albumin-chitosan microparticles for in vivo ocular drug delivery" by Richard T Addo et al, J Pharm Sci. 2015 May; 104(5):1677-90, which is herein incorporated by reference in its entirety.

Where, in some embodiments, microparticles have a mean size of about 2 microns, atropine concentration of 10% and a release time of about 50 hours. Such particles, in some embodiments are over coated with additional polymer/s with one or more different properties to achieve, in some embodiments, an accumulated extended release pattern over 7 days or longer.

For example, microparticles including one or more feature as described in "Development of Water-Compatible Molecularly Imprinted Polymers Based on Functionalized β-Cyclodextrin for Controlled Release of Atropine" by Yahui He et al, Polymers 2020, 12(1), 130, which is herein incorporated by reference in its entirety.

For example, Timolol nanoparticles.

For example, particles including one or more feature as described in "Chitosan nanoparticles for prolonged delivery of timolol maleate" by Sunil A Agnihotri 1, Tejraj M Aminabhavi, Drug Dev Ind Pharm. 2007 November; 33(11): 1254-62, which is herein incorporated by reference in its entirety.

In some embodiments, the particles have a mean particle size ranged between 118 and 203 nm, while, in some embodiments, zeta potential ranges between +17 and +22 mV. In some embodiments, entrapment efficiency of the nanoparticles ranges between 47.6 and 63.0%. In some embodiments, e.g. based on results in-vitro release studies performed in phosphate buffer saline of pH 7.4, release of timolol maleate is slow, e.g. by up to 24 hours. The particles, in some embodiments are over coated with additional polymer/s e.g. with different properties to arrive at an accumulated extended release pattern over 7 days or longer.

For example, timolol microparticles including one or more feature as described in "Sustained delivery of timolol maleate from poly(lactic-co-glycolic acid)/poly(lactic acid) microspheres for over 3 months" by James P Bertram 1, Sandeep S Saluja, Jodi McKain, Erin B Lavik, J Microencapsul. 2009 February; 26(1):26, which is herein incorporated by reference in its entirety.

In some embodiments, microspheres are fabricated using a 50:50 blend of PLGA 502H and PLA. In some embodiments, the microspheres deliver timolol maleate over 50-200 days, or 50-150 days, or 90-120 days, or about 107 days.

FIGS. 68A-B are simplified schematic cross sectional views of a device 6800 on an eye surface 6804, according to some embodiments of the invention.

For simplicity, device 6800 is illustrated as having a rectangular cross section, however device 6800, in some embodiments, has a shape (shape e.g. including curvature of a posterior and/or anterior surface of the device) having one or more feature of device/s described elsewhere within this document.

In some embodiments, device 6800 includes a layer 6812 which includes therapeutic material particles 6836. Where material particles 6836, in some embodiments, include one or more feature of microparticles and/or nanoparticles e.g. as described elsewhere in this document. Where, in some embodiments, other material of layer 6812 is rapidly dissolvable and/or degradable and/or erodible. Erosion, in some embodiments, revealing and allowing dispersion of particles 6836, for example, as shown in transition between FIG. 68A to FIG. 68B.

In some embodiments, particles 6836 include therapeutic material. Optionally, in some embodiments particles 6836 include mucoadhesive material. Potentially, once a particle is released from layer 6812 if it contacts eye surface 6804 (e.g. under movement/s of one or more of the eyelid, eyeball, and tear fluid) it adheres to the eye surface. In some embodiments, particles adhere to one or more mucosal surface e.g. including the eyeball and/or eyelid. In some embodiments, the particles then degrade (e.g. over about 10 minutes or about 1 hour, or about 12 hours, or about 1 day, or about 3 days, or lower or higher or intermediate time durations) to release therapeutic material to eye tissue.

Optionally, in some embodiments, device includes one or more additional layer (e.g. than layer 6812). For example, in some embodiments device 6800 includes a mucoadhesive layer 6810.

In some embodiments, therapeutic material layer 6812 including particles is incorporated into one or more of the device embodiments as described within this document. Including, for example, covering and/or access features to therapeutic material layer 6812.

Exemplary Manufacture of Exemplary Devices

In some embodiments, device manufacturing and/or film manufacturing processes include multi-layer casting and/or one or more other industrial processes such as: spraying, dipping, coating, brushing, extrusion, injection, electro-spinning, pressing, cutting, drilling, 3d printing, 3d engraving, laser cutting, heating, laser heating, chemical etching, chemical bonding, adhesive bonding.

In some embodiments, the device and/or portion/s of the device are formed by one or more of; gluing, blowing, casting, extrusion, coating, lamination, welding, pressing, spinning, chemical reaction, spraying, dipping, coating, brushing, extrusion, injection, electro-spinning, pressing, cutting, 3d printing, 3d engraving, laser cutting, heating, laser heating, chemical etching chemical bonding, adhesive bonding and any combination thereof.

FIG. 69 is a method of ophthalmic device manufacture, according to some embodiments of the invention.

At 6900, in some embodiments, a film is received. For example, a multi layered film. In some embodiments, the film is manufactured, e.g. according to one or more feature as illustrated in and/or described regarding FIG. 70 and/or according to one or more feature as described regarding Film Examples 1-55.

At 6902, in some embodiments, the film is shaped, e.g. using one or more method.

Where, when the film is in dry or wet form, it is, in some embodiments, manipulated to have a selected thickness profile and/or curvature and/or to add one or more features, such as: one or more protrusion, cavity, aperture, hole, slice. For example, in some embodiments, the device comprises at least one mechanically and/or chemically formed aperture.

In some embodiments, shaping includes one or more treatment. For example, treating by one or more of; application of mechanical force (e.g. pressing), heating and/or heat treatment, exposure to one or more chemical agent, treatment with one or more electrical process. Where a plurality of treatments, in some embodiments, are applied sequentially. Where a plurality of treatments, in some embodiments, are applied simultaneously (e.g. simultaneous heat and mechanical force treatment). In some embodiments, one or more type of treatment includes using a jig.

In some embodiments, the film is shaped by cutting, for example, by one or more of mechanical and chemical means. For example, by use of one or more of; cutting implements (e.g. scissors, knife), stamping, laser.

At 6904, optionally, in some embodiments, one or more additional material and/or layer is applied to the film.

At 6906, optionally, in some embodiments, the film is cut, to produce, in some embodiments, one or more individual ophthalmic device. For example, to provide a plurality of ophthalmic devices using a single portion of film. Where, in some embodiments, cutting is by one or more of mechanical and chemical means. For example, by use of one or more of; cutting implements (e.g. scissors, knife), stamping, laser.

At 6908, in some embodiments, the device is shaped. For example, according to one or more feature as described regarding step 6902.

At 6910, in some embodiments, optionally, in some embodiments, one or more additional material and/or layer is applied to the device and/or to a portion of the device e.g. in some embodiments, material is added to a circumference and/or edge region/s of the device.

At 6912, in some embodiments, optionally, the device is shaped. For example, according to one or more feature as described regarding step 6902.

At 6914, in some embodiments, the device is (and/or finished devices are) packaged. For example, into single-device and/or multi-device packages. In some embodiments, devices are packaged into kits. Where a kit, in some embodiments, includes one or more device, and one or more of insertion tool, additional medication/s, additional formulation/s for addition to the device and/or subject's eye.

The device, in some embodiments, is packaged attached to the insertion tool potentially increasing one or more of safety and eases of application to a subject's eye.

In some embodiments, the insertion tool has a cup shape (e.g. thimble shape) including a surface for the device e.g. where, in some embodiments, the device is placed at an opening of the cup shape. Where, in some embodiments, the cup shape is flexible and is squeezed to propel the device towards a surface to which it is desired that it adheres. The insertion tool, in some embodiments, is in a shape of elongated thimble with optional other portion/s.

In some embodiments, the device is kept wet at the end of the production process e.g. is packaged in a hydrated form. Alternatively, in some embodiments, the device is allowed to dry. In some embodiments, the device (e.g. after drying) packaged in a dry and/or semi-hydrated form.

At 6916, in some embodiments, the device is sterilized. For example, using one or more of; gamma radiation, ETO, steam.

In some embodiments, the order of steps 6914 and 6916 is reversed.

Device Manufacture Example 1

In some embodiments, a film (e.g. according to one or more features as described and/or illustrated regarding films elsewhere in this document) is cut into a desired shape (e.g. the shape including one or more feature of one or more of shapes as shown in any one of the figures). For example, using a punch. Where, in some embodiments, the film is cut into a disk shape.

In some embodiments, the shape (e.g. disk) is inserted into a mold and pressed to conform the disk anterior and/or posterior surfaces to desired curvatures e.g. including, in some embodiments, shaping edges of the device to a desired edge shape.

In some embodiments, excess material is removed (e.g. by laser cutting) and/or edge/s of the device are smoothed.

In some embodiments, the device is then packaged and/or sent to sterilization.

Device Manufacture Example 2

In some embodiments, a film (e.g. according to one or more features as described and/or illustrated regarding films elsewhere in this document) is shaped. For example, using a mold. Where, in some embodiments, pressure and/or heat are applied to the film to conform the film to the mold e.g. form the inner and outer curvature and/or a desired edge shape of the device.

In some embodiments, the shaped film is then laser cut e.g. into an oval shape.

In some embodiments, excess material is removed (e.g. by laser cutting) and/or edge/s of the device are smoothed.

In some embodiments, the device is then packaged and/or sent to sterilization.

Device Manufacture Example 3

The final device of "Device manufacture example 2" is taken and additional material is added to a circumference (e.g. an edge region) of the device e.g. to provide a desired edge characteristics e.g. shape and/or material composition.

In some embodiments, the device is then packaged and/or sent to sterilization.

Device Manufacture Example 4

In some embodiments, a film (e.g. according to one or more features as described and/or illustrated regarding films elsewhere in this document) is provided. In some embodiments, tunnel/s are cut and/or cavity/ies and/or pores are cut and/or created and/or drilled into the lubricious film layer.

In some embodiments, the film is then cut into a disk shape e.g. using punch.

In some embodiments, the film is shaped. For example, using a mold. Where, in some embodiments, pressure and/or heat are applied to the film to conform the film to the mold e.g. form the inner and outer curvature and/or the desired edge shape of the device on the film.

In some embodiments, excess material is removed (e.g. by laser cutting) and/or edge/s of the device are smoothed.

In some embodiments, the device is then packaged and/or sent to sterilization.

Device Manufacture Example 5

In some embodiments, a film (e.g. according to one or more features as described and/or illustrated regarding films elsewhere in this document) is provided. In some embodiments, tunnel/s are cut and/or cavity/ies and/or pores are cut and/or created and/or drilled into the mucoadhesive film layer.

In some embodiments, the film is then cut into a disk shape e.g. using punch.

In some embodiments, the film is shaped. For example, using a mold. Where, in some embodiments, pressure and/or heat are applied to the film to conform the film to the mold e.g.

form the inner and outer curvature and/or the a desired edge shape of the device on the film.

In some embodiments, excess material is removed (e.g. by laser cutting) and/or edge/s of the device are smoothed.

In some embodiments, the device is then packaged and/or sent to sterilization.

Device Manufacture Example 6

The manufacture of a device is based on the film that was prefabricated according to the above description, followed by additional processes performed:

In some embodiments, the film is cut into a disk shape e.g. using laser cutting.

In some embodiments, the disk shaped film portion is shaped. For example, using a mold. Where, in some embodiments, pressure and/or heat are applied to the film to conform the film to the mold e.g. form the inner and outer curvature and/or the a desired edge shape of the device on the film.

In some embodiments, the device is connected to a dispensing tool and/or to an insertion tool.

In some embodiments, the device is then packaged and/or sent to sterilization.

In some embodiments, one or more additional processes e.g. addition of layer/s and/or addition of therapeutic agent/s and/or addition of compounds is performed on one or more of the devices of Device manufacture examples 1-5 e.g. prior to packaging and/or sterilization.

FIG. 70 is a method of film manufacture, according to some embodiments of the invention.

At 7000, in some embodiments, a first solution is cast onto a support sheet.

In some embodiments, the first solution includes mucoadhesive material, where, for example, after casting, the mucoadhesive material forms a mucoadhesive first layer. Optionally, in some embodiments, the mucoadhesive solution (and/or layer) includes therapeutic agent/s. Alternatively or additionally, in some embodiments, after casting of the first solution, therapeutic agent/s are added to the casted surface (before and/or after drying of the surface).

In some embodiments, the first solution includes lubricious material where, for example, after casting, the lubricious material forms a lubricious first layer. Optionally, in some embodiments, the lubricious solution (and/or layer) includes therapeutic agent/s. Alternatively or additionally, in some embodiments, after casting of the first solution, therapeutic agent/s are added to the casted surface (before and/or after drying of the surface).

In some embodiments, the first solution includes neither lubricious material nor mucoadhesive material. In some embodiments, the first solution includes therapeutic material and/or therapeutic agent/s are added to the surface of the first layer formed by casting the first solution.

At 7002, optionally, in some embodiments, the first layer is treated.

For example, where the first layer has mucoadhesive properties, to give a surface of the first layer lubricious material characteristics. Where treatment includes, for example, one or more chemical process and/or material deposition.

For example, where the first layer has lubricious properties, to give a surface of the first layer mucoadhesive material characteristics. Where treatment includes, for example, one or more chemical process (e.g. plasma treatment) and/or material deposition (e.g. adding adhesive).

In some embodiments, the first layer is treated both to give it lubricious properties (e.g. on one side) and to give it mucoadhesive properties (e.g. on the other side). For example, when the first layer has neither mucoadhesive material nor lubricious material.

At 7004, optionally, in some embodiments, an additional material (e.g. a film) is applied to the first surface. For example, covering the first surface. For example, covering portions of the first surface e.g. in a pattern e.g. to provide portion/s of devices eventually produced from the multilayer film with additional material portion/s in specific place/s. In some embodiments, the additional is applied before the first layer dries fully. Alternatively, in some embodiments, it is applied to a dry first layer.

At 7006, optionally, in some embodiments, the additional is adhered to the first layer. For example, by adhesive and/or adhesive welding and/or by chemical and/or physical means.

At 7008, optionally, in some embodiments, the film is manipulate e.g. to shape the film. For example, including one or more feature of step 6902 FIG. 69.

At 7010, optionally, in some embodiments, a second solution is cast onto the film surface to form a second layer. Where, in some embodiments, if the first layer includes mucoadhesive material, the second layer includes intermediate layer feature/s and/or material/s (e.g. as described elsewhere in this document) and/or lubricious layer materials (e.g. as described elsewhere in this document).

At 7012, optionally, in some embodiments, the second layer is allowed to dry.

At 7014, optionally, in some embodiments, the film is manipulated e.g. to shape the film. For example, including one or more feature of step 6902 FIG. 69.

In some embodiments, additional layers are cast onto the film for example, following one or more of the steps of this method.

FIGS. 71A-D are simplified schematic cross sectional views of a film, according to some embodiments of the invention.

In some embodiments, FIGS. 71A-D illustrate cross sections views of a portion of a device.

In some embodiments, FIGS. 71A-D show different, portions, for example, sequential portions, of a manufacture process, according to some embodiments of the invention.

FIG. 72 is a method of manufacture, according to some embodiments of the invention.

Referring now to FIG. 71A, in some embodiments, a substrate 7174 is a film e.g. including one or more feature of films as described elsewhere in this document. For example, in some embodiments, the film includes a single layer. For example, in some embodiments, the film includes a plurality of layers e.g. each layer with different composition and/or material characteristics.

At step 300, and, for example, referring to FIG. 71B: In some embodiments, cavity/ies are made in substrate 7174. For example, by and/or using one or more of; Jigs, Press, Punch, Laser engraving, drilling, Molecularly imprinted polymer (MIP), 3D printing.

At step 302, and, for example, referring to FIG. 71C: In some embodiments, cavity/ies are filled e.g. with a different material 7178 to that of substrate 7174.

At step 304, and, for example, referring to FIG. 71D: In some embodiments, one or more additional layer 7180 is applied on top of the substrate layer 7174. In some embodiments, additional layer 7180 has different characteristics (e.g. different material characteristics) than other portion/s 7174, 7178.

In some embodiments, substrate 7174 includes mucoadhesive material, filling material 7178 includes therapeutic material, and additional layer 7180 includes lubricous material.

FIGS. 73A-E are simplified schematic cross sectional views of films, according to some embodiments of the invention.

FIGS. 73E-F are simplified schematic cross sectional views of devices, according to some embodiments of the invention.

In some embodiments, FIGS. 73A-F show different portions, for example, sequential portions moving in time from FIG. 73A through FIG. 73B through FIG. 73C through FIG. 73D through FIG. 73E through to FIG. 73F, of a manufacture process, according to some embodiments of the invention.

Referring to FIG. 73A, in some embodiments, a film 7374 is provided e.g. a film including one or more feature as described regarding films and/or layers (e.g. in some embodiments, film 7374 is a first layer of one or more exemplary film manufacture example).

In some embodiments, film 7374 is shaped to the configuration illustrated in FIG. 73B. Where, shaping, for example, includes one or more feature of step 6902 FIG. 69.

Referring to FIG. 73C, in some embodiments, additional material 7378 is added to the shaped film 7374 e.g. casted onto the shaped film e.g. including one or more feature as described regarding step 6904 FIG. 69.

Referring to FIG. 73D, in some embodiments, the film including two layers 7374, 7378 is shaped, where, shaping, for example, includes one or more feature of step 6902 FIG. 69.

Referring to FIG. 73D, in some embodiments, the film is cut into individual devices 7300 e.g. along dotted lines illustrated on FIG. 73D. In some embodiments, cutting includes one or more feature of step 6906 FIG. 69.

Referring to FIG. 73F, in some embodiments, device 7300 is shaped e.g. Additional features 7382 are formed on device 7300. For example, including one or more feature as described in step 6902 FIG. 69. For example, one or more cavity 7382. Where cavity/ies in some embodiments, are then filled with additional material (e.g. including one or more feature as illustrated in and/or described regarding FIGS. 71B-D)

FIGS. 74A-C are simplified schematic cross sectional views of a device 7400, according to some embodiments of the invention.

In some embodiments, device 7400 includes a first layer 7410 and a second layer 7412. In some embodiments, a device posterior surface 7416 is concave. In some embodiments, the concavity is filled with an additional material 7436. For example, during manufacture and/or by a user, for example just prior to use. Where, in some embodiments, additional material 7436 includes therapeutic ingredient/s. Where, in some embodiments, additional material 7436 includes mucoadhesive. Where, in some embodiments, device 7400 is used to extend residence time of a topical application in contact with the eye. For example, where device 7400 seals to an eye surface 7404 holding additional material 7437 in contact with the eye surface e.g. for a time period which is, in some embodiments, longer than residence time of eye drops and/or ointment for example. Where, in some embodiments, the time period is 10 minutes to 12 hours, or 10 minutes to 2 hours, or lower or higher or intermediate time durations or ranges.

In some embodiments, device 7400 includes lubricous material 7412 and/or mucoadhesive material 7410.

Exemplary Manufacture of an Exemplary Film

In some embodiments, a film is manufactured by casting two to three layers. For example, by applying a solution for each layer, successively, e.g. onto a support surface (e.g. support sheet). The support sheet, in some embodiments is flat or curved and/or includes pattern's e.g.

cavity/ies and/or bulge/s.

The support sheet, in some embodiments, is in a film and/or substrate. Where exemplary support sheet materials include; Teflon film, Teflon coated substrate, silicon film, silicon made and/or coated substrate, PET (polyethylene terephthalate) film, BoPET film, Melinex, MYLAR-A, Hostaphan, Kapton (polyimide) film, and combinations thereof. In some embodiments, the support sheet material is selected to enables casting of a first layer onto the support without lubricant and/or adhesive material.

In some embodiments, a first layer (e.g. lubricous layer) of a device is cast onto the support surface followed, optionally, by one or more intermediate layer. And, in some embodiments, followed by a mucoadhesive layer.

In some embodiments, one or more portion of separately manufactured (e.g. prefabricated) film is added e.g. to form a layer.

In some embodiments, layer casting order is reversed, for example, with a mucoadhesive layer being cast first followed, optionally, by intermediate layer/s and then, in some embodiments, a lubricous layer.

In some embodiment, e.g. alternatively to casting, one or more of the layers is added to previous layer/s and/or the support by one or more of extrusion, Injection, Injection molding, plating, deposition, Langmuir-Blodgett method, spin coating, dip coating.

In some embodiment, one or more prefabricated films or/or portion (e.g. particles e.g. microparticles and/or nanoparticles) parts, are incorporated in the device e.g. as part of casting solutions and/or formulations and/or between casted layers.

In some embodiments, one or more layer (e.g. each layer) is allowed to dry before a subsequent layer is cast.

Exemplary Solutions

In some embodiments, a CA:TEC solution includes Cellulose Acetate:TEC, TEC, acetone, and optionally dye/s and/or colorant/s.

In some embodiments, a CA:TEC solution is made by first dissolving Cellulose Acetate in acetone followed by adding TEC solution and optional dye/s and/or colorant/s.

In some embodiments, a Klucel solution includes Klucel, water, ethanol, and optionally dye/s and/or colorant/s.

In some embodiments, Klucel solution is made by dissolving Klucel powder in water and ethanol and then optionally adding dye/s and/or colorant/s.

In some embodiments, a Kollicoat solution includes Kollicoat and ethanol.

In some embodiments, Kollicoat solution is made by dissolving Kollicoat in ethanol.

In some embodiments, Klucel/974/Loteprednol solution includes Klucel, carbomer 974, Loteprednol, and ethanol.

In some embodiments, Klucel/974/Loteprednol solution is made by dissolving Klucel powder in ethanol, then adding carbomer 974 to the solution, then adding Loteprednol to the solution.

In some embodiments, Klucel/diclofenac solution includes Klucel, diclofenac, and ethanol.

In some embodiments, Klucel/diclofenac solution is made by dissolving Klucel powder in ethanol, then adding diclofenac to the solution.

In some embodiments, Ethyl cellulose:PEG solution includes Ethyl cellulose, Acetone/Ethanol and PEG solution.

In some embodiments, Ethyl cellulose:PEG solution is made by dissolving Ethyl cellulose in Acetone/Ethanol, followed by adding PEG solution.

The materials in the above examples may be replaced by any of the other materials that are mentioned elsewhere in this document.

In some embodiments the materials used e.g. in device manufacture are biocompatible and/or become biocompatible upon drying and/or treatment.

In some embodiments the materials used e.g. in the device are selected from:

Hydroxy Propyl Cellulose (HPC);

Hydroxy Propyl Methyl Cellulose (HPMC);

Carboxymethyl cellulose (CMC);

PolyVinyl Alcohol (PVOH);

PolyEthylene Glycol (PEG);

Cellulose Acetate (CA);

Polyvinyl alcohol-polyethylene glycol graft-copolymer (Kollicoat);

Poly Acrylic Acid (Carbopol or Carbomer for example)

Poly Acrylic Acid (Carbopol or Carbomer for example)

Hyaluronic Acid

Ethyl cellulose (EC)

Tri Ethyl Citrate (TEC)

Glycerol

Dextran; and combinations thereof.

In some embodiments, a device is constructed from a single material e.g. of the previous list. Where, in some embodiments, different layers and/or different material characteristics are producing using grades of the material and/or by treating the material in one or more way e.g. chemically and/or mechanically, and/or by heating and/or cooling.

Other examples of solutions are: PVOH:PEG:Glycerol or PVOH:PEG:HPMC or PVOH:HPC or PVOH:Kollicoat: Glycerol or PVOH:Kollicoat:Glycerol:CMC In some embodiments materials include any form, structure, formulation, derivatives, combination and/or alteration and/or salts of listed material/s.

In some embodiments additional materials are be used to adjust and/or change property/ies of materials used and/or to arrive at a device with selected properties (e.g. as described in this document.

Exemplary Therapeutic Agent/s

In some embodiments, therapeutic agent/s are added to a solution and/or put onto a dry layer. Where the therapeutic agent, in some embodiments, is in a form of: one or more solid (flat sheet, curved sheet, round sheet, oval sheet, ring, sphere, rod, bar), powder, ointment, liquid, bids, dispersion, solution, pellets, microparticles, nanoparticles, microspheres, and microcapsules, liposome, lysosomes, micelles and reverse micelles.

Film Example 1

CA:TEC solution is casted onto a support sheet as a first layer and allowed to dry.

Klucel solution is casted as a second layer onto the dry CA:TEC first layer, and is then allowed to dry.

Film Example 2

CA:TEC solution is casted onto a support sheet as a first layer and allowed to dry.

Therapeutic agent is added to a Klucel solution. The resulting Klucel solution is casted onto the dry CA:TEC first layer film to form a second layer and is then allowed to dry.

Film Example 3

One or more therapeutic agent, is added to a CA:TEC solution. The resulting solution is cast onto a support sheet as a first layer and allowed to dry.

Therapeutic agent, is added to a Klucel solution. The resulting solution is casted onto the dry CA:TEC first layer film to form a second layer, and allowed to dry.

Film Example 4

CA:TEC solution is casted onto a support sheet as a first layer and allowed to dry.

Therapeutic agent, in some embodiments, is added to the dried layer.

The therapeutic agent, in some embodiments, adhered to the layer by adhesive by adhesive welding and/or by chemical and/or physical means.

In some embodiments, the film is shaped to host the therapeutic agent. For example, one or more cavities and/or protrusions. The cavity/ies and/or protrusion/s, in some embodiments are created by one or more of; Jigs, Press, Punch, Laser engraving, drilling, Molecularly imprinted polymer (MIP), 3D printing.

One or more therapeutic agent, is added to Klucel solution.

The Klucel solution is casted as the second layer upon the dry CA:TEC (first layer) film and allowed to dry.

Film Example 5

One or more therapeutic agent, is added to a CA:TEC solution. The resulting solution is cast onto a support sheet as a first layer and allowed to dry.

One or more therapeutic agent, is added to a Klucel solution. The resulting solution is cast onto a the dry CA:TEC layer as a second layer and is then allowed to dry.

Optionally, the two layer film is then shaped e.g. with one or more cavity and/or protrusion. Jigs, Press, Punch, Laser engraving, drilling, Molecularly imprinted polymer (MIP), 3D printing One or more therapeutic agent, is applied to the dried Klucel layer. Where shape of the film, (e.g. provided by shaping previously performed) configures the film to host the therapeutic agent. For example, in some embodiments, cavity/ies hold therapeutic agent.

Optionally, the therapeutic agent is adhered e.g. chemical and/or physical (e.g. welding) adhesion method/s.

Klucel solution is then casted to form a third layer, and is then allowed to dry.

Film Example 6

Kollicoat solution is casted onto a support sheet as a first layer and allowed to dry.

CA:TEC solution is casted as a second layer onto the dry Kollicoat first layer, and is then allowed to dry.

Klucel solution is casted as a second layer onto the dry CA:TEC second layer, and is then allowed to dry.

Film Example 7

CA:TEC solution is casted onto a support sheet as a first layer and allowed to dry.

In some embodiments, the resulting CA:TEC film is shaped e.g. to configure the selected thickness profile and/or curvature and/or other features, such as: protrusions, cavities, apertures, holes, slices.

Klucel solution is casted as a second layer onto the dry, CA:TEC first layer, and is then allowed to dry.

In some embodiments, film shape is manipulated for example, to a selected thickness profile and/or curvature and/or to introduce feature/s, such as: one or more protrusion/s, cavity/ies, aperture/s, hole/s, slice/s.

Film Example 8

CA:TEC solution is casted onto a support sheet as a first layer.

In some embodiments, a layer of prefabricated film and/or portions of the first layer are added to region/s (e.g. in a pattern) of the first layer, before and/or after drying of the first layer.

In some embodiments, the film is subjected to one or more procedure to adhere the film to the CA:TEC first layer. For example, one or more of gluing, heating, and pressing.

Klucel solution is then casted onto the film, and is then allowed to dry.

Film Example 9

The support sheet surface and/or parts of it are covered with a prefabricated film or parts of film (e.g. in a specific pattern).

Optionally, in some embodiments, the surface is then treated to adhere the prefabricated film e.g. using one or more of gluing, heating, pressing.

CA:TEC solution is casted onto the support sheet+prefabricated film layer, and allowed to dry.

Optionally, in some embodiments, the surface is then treated to adhere the prefabricated film e.g. using one or more of gluing, heating, pressing.

Klucel solution is then casted onto the dry CA:TEC (first layer) film and allowed to dry.

Film Example 10

The manufacture of a film is based on solutions preparation followed by two casting processes performed:

CA:TEC Solution is casted as a first layer upon the support sheet and allowed to dry.

Klucel/974/Loteprednol solution is casted as the second layer upon the dry CA:TEC (first layer) film and allowed to dry.

Film Example 11

The manufacture of a film is based on solutions preparation followed by two casting processes performed:

CA:TEC solution is casted as the first layer upon the support sheet and allowed to dry.

Ciprofloxacin dissolved in acetic acid is added to a Klucel/974/Ciprofloxacin solution.

The Klucel/974/Ciprofloxacin solution is casted as the second layer upon the dry CA:TEC (first layer) film and allowed to dry.

Film Example 12

CA:TEC solution is casted as the first layer upon the support sheet and allowed to dry.

Klucel/diclofenac solution is casted as the second layer upon the dry CA:TEC (first layer) film and allowed to dry.

Film Example 13

Ethyl cellulose:PEG solution is casted as the first layer upon the support sheet and allowed to dry.

Klucel solution is casted as the second layer upon the dry Ethyl cellulose:PEG (first layer) film and allowed to dry.

Film Example 14

Ethyl cellulose:PEG/Ibuprofen Solution—Ethyl cellulose (EC) are dissolved in Acetone/Ethanol, followed by the addition of PEG solution and then addition of Ibuprofen.

EC:PEG/Ibuprofen Casting—The EC:PEG/Ibuprofen solution is casted as the first layer upon the support sheet and allowed to dry.

Klucel solution is casted as the second layer upon the dry EC:PEG/Ibuprofen (first layer) film and allowed to dry.

Film Example 15

CA:TEC solution is casted as the first layer upon the support sheet and allowed to dry. Carboxymethyl cellulose (CMC) solution—CMC powder is dissolved in Water, and optionally dye and/or colorant are added.

The CMC solution is casted as the second layer upon the dry CA:TEC (first layer) film and allowed to dry.

Additional CMC layers, in some embodiments, are casted on top of dried CMC layer.

General

It is expected that during the life of a patent maturing from this application many relevant ophthalmic treatments and/or ophthalmic devices and/or therapeutic ingredients will be developed and the scope of the terms ophthalmic treatment and/or ophthalmic device and/or therapeutic ingredients is intended to include all such new technologies a priori.

As used herein the term "about" refers to ±20%

The terms "comprises", "comprising", "includes", "including", "having" and their conjugates mean "including but not limited to".

The term "consisting of" means "including and limited to".

The term "consisting essentially of" means that the composition, method or structure include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" include a plurality of compounds, including mixtures thereof.

Throughout this application, various embodiments of this invention, in some embodiments, is presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, also be provided in combination in a single embodiment. Conversely, various features of the invention, which are, for brevity, described in the context of a single embodiment, also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. An ophthalmic device comprising:

a body having:

a posterior surface;

an anterior surface;

wherein a size of the body, a shape of the posterior surface, and a shape of the anterior surface configures the device to reside on a bulbar conjunctiva of an eye;

wherein the device is flexible and has a Young modulus of from 0.3 to 1.5 MPa;

wherein the body of the ophthalmic device is configured to reside on the bulbar conjunctiva of the eye for a period of less than 24 hours from administration.

2. The device of claim 1, wherein, when in residence on the bulbar conjunctiva, the posterior surface is adjacent to the bulbar conjunctiva and the anterior surface is adjacent to an inner eyelid surface, at least periodically.

3. The device according to claim 1, wherein the body comprises therapeutic material and is configured to elute the therapeutic material into the eye when residing on the bulbar conjunctiva.

4. The device according to claim 1, wherein an extent of the body is 2-8 mm.

5. The device according to claim 1, having a mass of from 5 mg to 40 mg.

6. The device of claim 1, wherein the posterior surface comprises material which disintegrates within an eye.

7. The device of claim 1, wherein the posterior surface comprises one or both of biodegradable and bioerodible material.

8. The device of claim 1, wherein the device comprises one or more electronic elements.

9. The device of claim 1, wherein the device is supplied in dry or semi-hydrated form.

10. The device of claim 1, wherein the device is configured to hydrate on the bulbar conjunctiva and thereby expand by no less than 10% and no more than 50% along one dimension.

11. The device of claim 1, wherein the body comprises more than one layer with different material characteristics.

12. The device of claim 1, wherein the body comprises one or more of:

PolyVinyl Alcohol (PVOH); PolyEthylene Glycol (PEG); Glycerol; Dextran; and combinations thereof.

13. The device of claim 1, where the body comprises one or more of hyaluronic acid, gelatin, and methyl cellulose.

14. A method of treating a patient suffering from an ophthalmic condition, the method comprising:

covering a portion of a bulbar conjunctiva under the lower eyelid with an ophthalmic device according to claim 1, causing the ophthalmic device to adhere to the bulbar conjunctiva through suction provided by surface tension forces generated by a difference in curvature between a posterior surface of the ophthalmic device and the bulbar conjunctiva; and allowing the device to elute a therapeutic material into the patient's eye to treat the ophthalmic condition.

15. The method of claim 14, wherein causing the ophthalmic device to adhere to the bulbar conjunctiva comprises deforming a central region of the device.

16. The method of claim 14, wherein the device is retrieved from dry storage and not hydrated before the portion of the bulbar conjunctiva under the lower eyelid is covered by the device.

17. A method comprising:

applying the device of claim 1 to a portion of the bulbar conjunctiva between the cornea and the conjunctiva of a lower fornix of a patient with the posterior surface facing the patient's eye, with the anterior surface facing the patient's lower eyelid; and allowing the device to reside on the bulbar conjunctiva for at least 15 minutes and for no longer than 24 hours.

18. The method of claim 17, wherein the residence time is from 2 hours to 8 hours.

19. The method of claim 17, wherein the device is retrieved from dry storage and not hydrated before being applied to the portion of the bulbar conjunctiva.

20. An ophthalmic device comprising:

a body having:

a posterior surface; and an anterior surface;

wherein the body comprises therapeutic material and is configured to elute the therapeutic material into the eye, wherein a size of the body, a shape of the posterior surface, and a shape of the anterior surface configure the device to reside on a bulbar conjunctiva of an eye, between the cornea and the conjunctiva of a lower fornix, wherein an entirety of the device, prior to use in the eye, is flexible and has a Young's modulus of from 0.3 to 1.5 MPa;

wherein the body of the device is configured to reside on the bulbar conjunctiva of the eye and elute the therapeutic material into the eye for a period of less than about 24 hours from administration.

21. A method of treating a patient suffering from an ophthalmic condition, the method comprising:

applying an ophthalmic device, without pre-hydrating the device, to a bulbar conjunctiva of the patient's eye in such a way as to allow the ophthalmic device to reside on the bulbar conjunctiva for a residence time of at least 15 minutes, with no portion of the device residing above the patient's lower eyelid, the device comprising a body having a posterior surface and an anterior surface, the body comprising therapeutic material which is eluted into the patient's eye to treat the ophthalmic condition, the device undergoing hydration in situ by the patient's tear fluid, wherein the hydration causes the device to expand by at least 10% but no more than 50% along one dimension;

wherein the residence time is no more than 24 hours; and wherein the device is flexible and has a Young modulus of from 0.3 to 1.5 MPa.

22. A method of treating a patient suffering from an ophthalmic condition, the method comprising:

applying an ophthalmic device to a bulbar conjunctiva of the patient's eye in such a way as to allow the ophthalmic device to reside in the eye of the patient for a residence time of up to 24 hours, the device comprising a body having a posterior surface and an anterior surface, the body comprising therapeutic material which is eluted into the patient's eye to treat the ophthalmic condition; and at the conclusion of the residence time, expelling or removing the device from the bulbar conjunctiva;

wherein the device is flexible and has a Young modulus of from 0.3 to 1.5 MPa.

23. The method of claim 22, comprising, after expelling or removing the device from the bulbar conjunctiva, repeating all steps of claim 22 with a second ophthalmic device that is essentially identical in shape and composition to the device of claim 1.

24. A method of treating a patient suffering from an ophthalmic condition, the method comprising:

covering a portion of a bulbar conjunctiva with an ophthalmic device, causing the ophthalmic device to adhere to the bulbar conjunctiva through suction provided by surface tension forces generated by a difference in curvature between a posterior surface of the ophthalmic device and the bulbar conjunctiva;

leaving the ophthalmic device on the bulbar conjunctiva for a residence time period; and degrading the device during the residence time period by exposing the device to tear fluid and movement of the patient's eyeball and lower eyelid;

wherein the degrading reduces adherence of the device to the bulbar conjunctiva;

wherein the residence time is no more than 24 hours;

wherein the device is flexible and has a Young modulus of from 0.3 to 1.5 MPa.

25. A method of treating a patient suffering from an ophthalmic condition, the method comprising:

covering a portion of a bulbar conjunctiva under the lower eyelid with an ophthalmic device, causing the ophthalmic device to adhere to the bulbar conjunctiva through suction provided by surface tension forces generated by a difference in curvature between a posterior surface of the ophthalmic device and the bulbar conjunctiva; and allowing the device to elute a therapeutic material into the patient's eye to treat the ophthalmic condition;

wherein the device is allowed to reside in the patient's eye for a time period of not more than 24 hours; and wherein the device is flexible and has a Young modulus of from 0.3 to 1.5 MPa.

26. The method of claim 25, wherein causing the ophthalmic device to adhere to the bulbar conjunctiva comprises deforming a central region of the device.

27. The method of claim 25, wherein the device is retrieved from dry storage and not hydrated before the portion of the bulbar conjunctiva under the lower eyelid is covered by the device.

* * * * *